(12) United States Patent
Robinson et al.

(10) Patent No.: US 8,026,236 B2
(45) Date of Patent: Sep. 27, 2011

(54) 6-PHENYL-1H-IMIDAZO[4,5-C]PYRIDINE-4-CARBONITRILE DERIVATIVES

(75) Inventors: John Stephen Robinson, Newhouse (GB); Philip Stephen Jones, Newhouse (GB); Jiaqiang Cai, Newhouse (GB); David Jonathan Bennett, Newhouse (GB)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 12/686,692

(22) Filed: Jan. 13, 2010

(65) Prior Publication Data

US 2010/0184761 A1 Jul. 22, 2010

Related U.S. Application Data

(60) Provisional application No. 61/145,231, filed on Jan. 16, 2009.

(51) Int. Cl.
| | |
|---|---|
| A61K 37/5377 | (2006.01) |
| A61K 31/437 | (2006.01) |
| C07D 471/02 | (2006.01) |
| C07D 413/14 | (2006.01) |
| A61P 19/02 | (2006.01) |
| A61P 17/06 | (2006.01) |

(52) U.S. Cl. ............ 514/234.2; 514/303; 546/118; 544/127

(58) Field of Classification Search ........... 514/234.2, 514/303; 546/118; 544/127
See application file for complete search history.

(56) References Cited

U.S. PATENT DOCUMENTS

| 7,687,515 B2 | 3/2010 | Cai et al. | |
|---|---|---|---|
| 2007/0197510 A1 | 8/2007 | Ohmoto et al. | |
| 2009/0099172 A1* | 4/2009 | Cai et al. | 514/234.2 |

FOREIGN PATENT DOCUMENTS

| EP | 1724264 | 11/2006 |
|---|---|---|
| WO | WO 03/020278 | 3/2003 |
| WO | WO 03/020287 | 3/2003 |
| WO | WO 03/020721 | 3/2003 |
| WO | WO 04/000819 | 12/2003 |
| WO | WO 04/000843 | 12/2003 |
| WO | WO 2005/085210 | 9/2005 |
| WO | WO 2007/080191 A | 7/2007 |
| WO | WO 2009/010491 A | 1/2009 |

OTHER PUBLICATIONS

International Search Report (PCT/US 2007/050356) for 2006.940US mail date Mar. 16, 2007, 2 pages.
Written Opinion of the International Searching Authority for PCT/US2007/050356-2006.940US, 5 pages.
International Search Report (PCT/EP2010/050418) for 2009.096US mail date Mar. 1, 2010, 2 pages.
International Search Report (PCT/EP2008.059172) for 2007.017US mail date Oct. 17, 2008, 3 pages.
Written Opinion of the International Searching Authority for PCT/EP2008.059172)-2007.017US, 5 pages.

* cited by examiner

*Primary Examiner* — D M Seaman
*Assistant Examiner* — Niloofar Rahmani
(74) *Attorney, Agent, or Firm* — Susan L. Hess; Gerard M. Devlin

(57) ABSTRACT

The present invention relates to 6-phenyl-1H-imidazo[4,5-c]pyridine-4-carbonitrile derivatives having the general Formula I

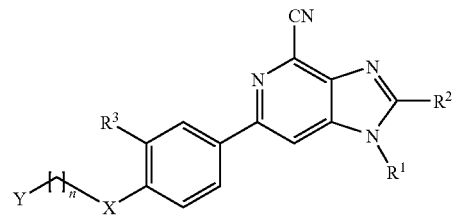

Formula I to pharmaceutical compositions comprising the same as well as to the use of these derivatives for the preparation of a medicament for the treatment of cathepsin S related diseases such as atherosclerosis, obesity, inflammation and immune disorders, such as rheumatoid arthritis, psoriasis, cancer, and chronic pain, such as neuropathic pain.

8 Claims, No Drawings

6-PHENYL-1H-IMIDAZO[4,5-C]PYRIDINE-4-CARBONITRILE DERIVATIVES

This application is a non-provisional application that claims priority under 35 U.S.C.§119(e) of provisional application U.S. Ser. No. 61/145,231 filed Jan. 16, 2009, the contents of which are hereby incorporated by reference in its entirety.

The invention relates to 6-phenyl-1H-imidazo[4,5-c]pyridine-4-carbonitrile derivatives, to pharmaceutical compositions comprising the same, as well as to the use of these derivatives for the preparation of a medicament for the treatment of cathepsin S and/or cathepsin K related diseases such as osteoporosis, atherosclerosis, obesity, inflammation and immune disorders, such as rheumatoid arthritis, psoriasis, lupus, asthma and chronic pain, such as neuropathic pain.

Cysteine proteases represent a class of peptidases characterised by the presence of a cysteine residue in the catalytic site of the enzyme, and these proteases are associated with the normal degradation and processing of proteins. Many pathological disorders or diseases are the results of abnormal activity of cysteine proteases such as over expression or enhanced activation. The cysteine cathepsins, e.g. cathepsin B, K, L, S, V, F, are a class of lysosomal enzymes which are implicated in various disorders including inflammation, autoimmune diseases, e.g. rheumatoid arthritis, psoriasis, asthma, osteoarthritis, osteoporosis, tumors, coronary disease, atherosclerosis, and infectious diseases.

Cathepsin S is highly expressed in antigen presenting cells of lymphatic tissues, primarily in lysosomes (Bromme et al., Science, 5, 789, 1996; Riese, et al., Immunity, 4, 357, 1996). In the antigen presenting cells cathepsin S plays a major role in antigen presentation by degradation of invariant chain that is associated with the major histocompatibility class II complex. Cathepsin S is also believed to be involved in the antigen processing as well. Cathepsin S deficient mice are healthy and normal in most respects but exhibit defects in immune functions and showed marked resistance to the development of collagen-induced arthritis (Nakagawa et al., Immunity, 10, 207, 1999; Shi et al, Immunity, 10, 197, 1999; Yang et al., 174, 1729, 2005). Cathepsin S inhibitors are effective in an asthma model (Riese et al., J. Clin. Invest. 101, 2351, 1998). Blocking invariant chain degradation should decrease antigen presentation to CD4 cells specifically and as such reduces unwanted side effects of other immunosuppressive drugs such as steroids. A recent patent publication (Johnson & Johnson, US 2007/0117785) has revealed that inhibitors of cathepsin S block the presentation of several crude allergen extracts in a human ex vivo assay, thereby supporting the use of cathpsin S inhibitors for the treatment of certain allergic conditions, such as rheumatoid arthritis, psoriasis. Different from most other lysosomal proteases that are only active under acidic conditions, the activity of cathepsin S exhibits a broad pH optimum that extents to alkaline pH. This feature enables that cathepsin S to function both inside and outside lysosomes (Broemme et al., Febs Lett., 286, 189, 1991). The broad pH feature and the high elastase activity of extracellular cathepsin S could also contribute to extensive remodeling of extracellular matrix architecture. As a result, cathepsin S has been shown to degrade all of the major components of the extracellular matrix and has been implicated in the pathogenic response that leads to atherosclerosis, obesity, emphysema and chronic obstructive pulmonary disease and cancer (Shi, et al., Atherosclerosis, 186, 411, 2006; Clement et al., Clin Chem Lab Med., 45(3), 328, 2007; Chang et al., J Cancer Mol., 3(1), 5, 2007; Shi et al., Immunity, 10, 197, 1999; Zheng et al., J Clin. Invest., 106, 1081, 2000; Libby et al., J Clin Invest 102, 576, 1998; Sukhova et al, ibid, 111, 897, 2003). It was reported that serum cathepsin S level is significantly increased in both atherosclerosis and diabetes patients and modulating cathepsin S activity may have therapeutic application in the treatment of patients with these common illnesses (Shi, et al., Atherosclerosis, 186, 411, 2006; Clement et al., Clin Chem Lab Med., 45(3), 328, 2007). Cathepsin S has been indicated for pain (WO 2003020278; Clark et al., PNAS, 104, 10655, 2007), cancer process, e.g. angiogenesis, metastasis, growth and cell proliferation (Johnston et al., Am J Path., 163, 175, 2003; Kos et al., Brit J Cancer, 85, 1193, 2001). Recent publication has also indicated that cathepsin S inhibitor alone or in combination with proteasome inhibition can have therapeutic usage against inflammation-induced neurodegenerative disease, such as multiple sclerosis (Weissert, et al., Eur. J. Immunol., 38, 2401, 2008).

Other cysteine cathepsins, e.g cathepsin K has strong collagenolytic, elastase and gelatinase activities (Bromme et al., J. Biol, Chem, 271, 2126-2132, 1996) and is predominantly expressed in osteoclasts (Bromme and Okamoto, Biol. Chem. Hopp-Seyler, 376, 379-384, 1995). It cleaves key bone matrix proteins, including type I and II collagen (Kaffienah et al., Biochem. J. 331, 727-732, 1998), gelatine, osteopontin and osteonectin, and as such is involved in extracellular matrix metabolism necessary for normal bone growth and remodelling (Bossard et al., J. Biol. Chem. 271, 12517-12524, 1996). Inhibition of cathepsin K should result in the diminution of osteoclast mediated bone resorption. Cathepsin K inhibitors may therefore represent new therapeutic agents for the treatment of disease states in man such as osteoporosis, cancer, osteoarthritis. Recent publication also suggest that cathepsin K plays a critical role in the immune system and may serve as a valid therapeutic target in autoimmune diseases (Takayanagi, et al., Science, 319, 624, 2008). Sukhova et al (J. Clin. Invest. 102, 576-583, 1998) have demonstrated that cells (macrophages) that migrate into and accumulate within developing human atherosclerotic plaques also synthesize the potent elastases Cathepsin K and S. Matrix degradation, particularly in the fibrous cap of such plaques, is a crucial process in atherosclerotic lesion destabilization. Thus, the metabolism of the extracellular matrix components collagen and elastin, which confer structural integrity upon the lesion's fibrous cap, can critically influence the clinical manifestations of atherosclerosis, such as coronary artery thrombosis as a result of rupture of an atherosclerotic plaque. Inhibition of cathepsins K and S at sites of plaques prone to rupture may thus represent an effective way of preventing such events.

4-Amino-pyrimidine-2-carbonitrile derivatives have been disclosed as inhibitors of cathepsins K and/or S in the International Patent Application WO 03/020278 (Novartis Pharma GMBH), while structurally related 4-amino-pyrimidine-2 carbonitrile derivatives were recently disclosed in WO04/000819 (ASTRAZENECA AB) as cathepsin S inhibitors. Pyrrolo-pyrimidines have likewise been disclosed as cathepsin K and/or S inhibitors in WO 03/020721 (Novartis Pharma GMBH) and WO 04/000843 (ASTRAZENECA AB). Recently, carbonitrile substituted bicyclic nitrogen containing aromatic systems were disclosed in the International Patent Application WO 05/085210 (Ono Pharmaceutical Co.) as cysteine protease inhibitors useful in the treatment of osteoporosis. More recently 6-phenyl-1H-imidazo[4,5-c]pyridine-4-carbonitrile derivatives have been disclosed in the International Patent Application WO 2007/080191 (AKZO NOBEL N.V.) as inhibitors of Cathepsins S and K.

There remains a need for further cathepsin inhibitors, especially for compounds having a preferential inhibitory activity for cathepsin S and having improved cellular invariant chain degradation functional activity with reduced or no activity against hERG (human-ether-a-go-go) channel.

To that aim the present invention provides 6-phenyl-1H-imidazo[4,5-c]pyridine-4-carbonitrile derivatives having the general Formula I

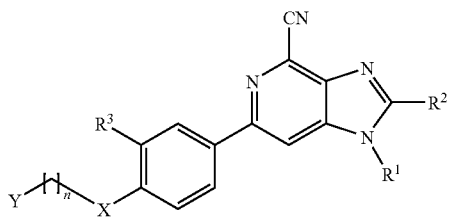

Formula I wherein
$R_1$ is H or $(C_{1-3})$alkyl;
$R_2$ is H or $(C_{1-3})$alkyl;
$R_3$ is halogen or $(C_{1-4})$alkyl, optionally substituted with one or more halogens;
X is $CH_2$, O or S;
n is 1-3;
Y is selected from
  $NR_4COR_5$,
  $NR_4SO_2R_5$,

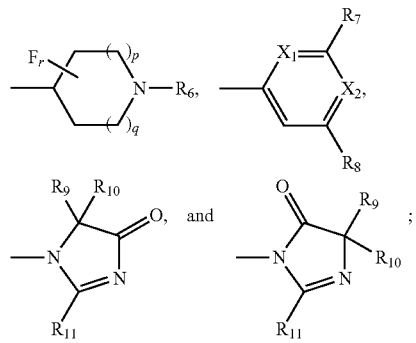

$R_4$ is H, $(C_{1-3})$alkyl or $(C_{3-5})$cycloalkyl;
$R_5$ is H, $(C_{1-6})$alkyl, $(C_{3-5})$cycloalkyl, $NR_{12}R_{13}$, $CR_{16}R_{17}NR_{12}R_{13}$, Het or a saturated 4-6-membered $NR_{11}$ containing ring;
$R_6$ is H, $(C_{1-4})$alkyl, $(C_{3-5})$cycloalkyl, halo$(C_{1-6})$alkyl, $(C_{1-3})$alkyloxy$(C_{1-3})$alkyl, $(CH_2)_mCONR_{12}R_{13}$, $CO(C_{1-6})$alkyl, $COCR_{16}R_{17}NR_{12}R_{13}$, $SO_2(C_{1-6})$alkyl, Het, COHet or $CH_2$Het;
r=0-3; p=0-2; q=0-2;
$X_1$ and $X_2$ are independently CH or N; one of $R_7$ and $R_8$ is selected from halogen, $(C_{1-3})$alkyloxy, $NR_{14}R_{15}$, $CONR_{14}R_{15}$, $NR_{14}COR_{15}$, $COO(C_{1-3})$alkyl and phenyl; the other is H or halogen;
$R_9$ and $R_{10}$ are independently H, $(C_{1-3})$alkyl; or
$R_9$ an $R_{10}$ form together with the carbon to which they are bonded a 3-5 membered saturated ring;
$R_{11}$ is H or $(C_{1-3})$alkyl;
m is 0 or 1;
Het is a 5- or 6-membered heteroaryl ring comprising 1-3 heteroatoms selected from O, S and N, optionally substituted with $(C_{1-3})$alkyl;

$R_{12}$ and $R_{13}$ are independently H, $(C_{1-6})$alkyl, or $(C_{1-3})$alkyloxy$(C_{1-3})$alkyl; or
$R_{12}$ and $R_{13}$ form together with the N to which they are bonded a 5-10 membered saturated heterocyclic ring, optionally comprising a further heteroatom selected form O and S;
$R_{14}$ and $R_{15}$ are independently H or $(C_{1-6})$alkyl; or
$R_{14}$ and $R_{15}$ form together with the N to which they are bonded a 5-7 membered saturated heterocyclic ring;
$R_{16}$ and $R_{17}$ are independently H or $(C_{1-3})$alkyl; or
$R_{16}$ and $R_{17}$ form together with the carbon atom to which they are bonded a cyclopropyl ring;
with the proviso that when r is 0, $R_6$ is not H or $(C_{1-4})$alkyl, or a pharmaceutically acceptable salt thereof.

The 6-phenyl-1H-imidazo[4,5-c]pyridine-4-carbonitrile derivatives of the invention are inhibitors of cathepsin S and cathepsin K and can therefor be used for the preparation of a medicament for the treatment of osteoporosis, atherosclerosis, inflammation and immune disorders, such as rheumatoid arthritis, psoriasis, asthma, and chronic pain, such as neuropathic pain.

The compounds of general Formula I exhibit a much improved cell based cathepsin S inhibitory activity on cleavage of MHC class II invariant chain which is measured by lip10 accumulation, as compared to the compounds disclosed in WO 2007/080191. In most cases, compounds of general Formula I are greater than 10 fold more active in this cell based activity than the compounds of WO 2007/080191. In some cases, these cell based activities are up to 100 fold greater than previously disclosed compounds in WO 2007/080191.

Furthermore, the 6-phenyl-1H-imidazo[4,5-c]pyridine-4-carbonitrile derivatives of the invention have at least 10 fold lower affinities to hERG (human ether-a-go-go) channel as compared to the 6-phenyl-1H-imidazo[4,5-c]pyridine-4-carbonitrile derivatives disclosed in WO 2007/080191. The hERG binding affinities for the best compounds of the current invention are even too low to be properly determined in many cases.

The term $(C_{1-6})$alkyl, as used in the definition of formula I, means a branched or unbranched alkyl group having 1-6 carbon atoms, like hexyl, pentyl, 3-methyl-butyl, butyl, isobutyl, tertiary butyl, propyl, isopropyl, ethyl and methyl.

The term $(C_{1-4})$alkyl means a branched or unbranched alkyl group having 1-4 carbon atoms, like butyl, isobutyl, tertiary butyl, propyl, isopropyl, ethyl and methyl.

The term $(C_{1-3})$alkyl means a branched or unbranched alkyl group having 1-3 carbon atoms, like propyl, isopropyl, ethyl and methyl. In the terms $(C_{1-3})$alkylcarbonyl and $(C_{1-3})$alkyloxy$(C_{1-3})$alkyl each occurrence of $(C_{1-3})$alkyl has the meaning as previously given.

The term halo$(C_{1-6})$alkyl means a $(C_{1-6})$alkyl group, as previously defined, substituted by one or more halogens, preferably one or more fluoro.

The term $(C_{3-5})$cycloalkyl means a cycloalkyl group having 3-5 carbon atoms, such as cyclopentyl, cyclobutyl and cyclopropyl.

In the definition of formula I Het means a 5- or 6-membered heteroaryl ring comprising 1-3 heteroatoms selected from O, S and N. These heteroaryl rings may be substituted with $(C_{1-3})$alkyl, $(C_{1-3})$alkyloxy or halogen. Examples of such heteroaryl rings, which are attached through a carbon atom, are imidazolyl, pyrazolyl, thiazolyl, isothiazolyl, oxazolyl, isoxazolyl, thienyl, oxadiazolyl, pyridinyl, pyrimidinyl and the like. Preferred 5-membered rings are 1,3-thiazol-2-yl, 1,3-oxazol-2-yl, 1,2-oxazol-3-yl, 1,2,4-oxadiazol- 3-yl, 1,2,4-oxadiazol-5-yl, 5-methyl-isoxazol-3-yl and 3-methyl-isoxazol-5-yl. A preferred 6-membered ring is pyridin-2-yl.

In the definition of formula I $R_5$ can be a saturated 4-6-membered $NR_{11}$ containing ring, wherein $R_{11}$ is H or $(C_{1-3})$ alkyl, such as N-methylazetidin-3-yl, N-methylpyrrolidin-2-yl and N-methylpiperidin-2-yl and the like.

In the definition of formula I $R_{12}$ and $R_{13}$, or $R_{14}$ and $R_{15}$, can form together with the nitrogen to which they are bound a 5-10 membered saturated heterocyclic ring, such as a pyrrolidine, a piperidine, or a 1H-azepine ring. Such rings may contain a further heteroatom selected from O and S, to form rings such as morpholine and thiomorpholine. Also included in the definition of these rings are bi- or tri-cyclic saturated heterocyclic ring systems, such as 2-azabicyclo[2.2.1]heptan-2-yl, 7-zabicyclo[2.2.1]heptan-7yl, as well as spiro-ring systems such as 6-azaspiro[3,4]-octan-6-yl, 1-oxo-2,8-diaza-spiro[4,5]-dec-8-yl, 2,4-dioxo-1,3,8-triaza-spiro[4,5]dec-8-yl, 2,4-dioxo-1,3,8-triaza-spiro[4,5]dec-3-yl, 6,9-diaza-spiro[4,5]dec-9-yl and the like. The term halogen means F, Cl, Br, or I. When halogen is a substituent at an alkyl group, F is preferred. A preferred halogen substituted alkyl group is trifluoromethyl.

In one embodiment the present invention provides 6-phenyl-1H-imidazo[4,5-c]pyridine-4-carbonitrile derivatives having the general Formula I

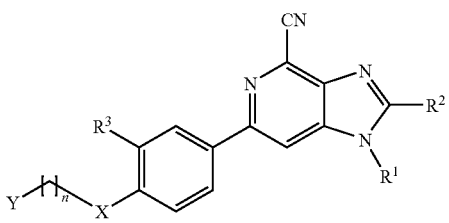

Formula I wherein
$R_1$ is H or $(C_{1-3})$alkyl;
$R_2$ is H or $(C_{1-3})$alkyl;
$R_3$ is halogen or $(C_{1-4})$alkyl, optionally substituted with one or more halogens;
X is $CH_2$, O or S;
n is 1-3;
Y is selected from
$NR_4COR_5$,
$NR_4SO_2R_5$,

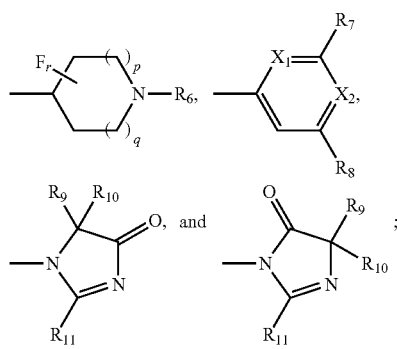

$R_4$ is H, $(C_{1-3})$alkyl or $(C_{3-5})$cycloalkyl;
$R_5$ is H, $(C_{1-6})$alkyl, $(C_{3-5})$cycloalkyl or $NR_{12}, R_{13}$;

$R_6$ is H, $(C_{1-4})$alkyl, $(C_{3-5})$cycloalkyl, halo$(C_{1-6})$alkyl, $(C_{1-3})$alkyloxy$(C_{1-3})$alkyl, $(CH_2)_m CONR_{12}R_{13}$, $CO(C_{1-6})$alkyl, $SO_2(C_{1-6})$alkyl, COHet or $CH_2$Het;
r=0-3; p=0-2; q=0-2;
$X_1$ and $X_2$ are independently CH or N; one of $R_7$ and $R_8$ is selected from halogen, $(C_{1-3})$alkyloxy, $NR_{14}R_{15}$, $CONR_{14}R_{15}$, $NR_{14}COR_{15}$, $COO(C_{1-3})$alkyl and phenyl; the other is H or halogen;
$R_9$ and $R_{10}$ are independently H, $(C_{1-3})$alkyl; or
$R_9$ an $R_{10}$ form together with the carbon to which they are bonded a 3-5 membered saturated ring;
$R_{11}$ is H or $(C_{1-3})$alkyl;
m is 0 or 1;
Het is a 5-membered heteroaryl ring comprising 1-3 heteroatoms selected from O, S and N, optionally substituted with $(C_{1-3})$alkyl;
$R_{12}$ and $R_{13}$ are independently H or $(C_{1-6})$alkyl; or
$R_{12}$ and $R_{13}$ form together with the N to which they are bonded a 5-7 membered saturated heterocyclic ring, optionally comprising a further heteroatom selected form O and S;
$R_{14}$ and $R_{15}$ are independently H or $(C_{1-6})$alkyl; or
$R_{14}$ and $R_{15}$ form together with the N to which they are bonded a 5-7 membered saturated heterocyclic ring; with the proviso that when r is 0, $R_6$ is not H or $(C_{1-4})$alkyl,
or a pharmaceutically acceptable salt thereof.

Preferred in the invention are those compounds according to Formula I wherein $R_1$ is methyl. Further preferred are compounds of formula I wherein $R_3$ is $CF_3$.

Also preferred are compounds of the invention wherein X is O and n is 1 or 2 or 3. Especially preferred are compounds of the invention wherein Y is $NR_4COR_5$.

Specifically preferred 6-phenyl-1H-imidazo[4,5-c]pyridine-4-carbonitrile derivatives of the invention are:
N-(3-(4-(4-cyano-1-methyl-1H-imidazo[4,5-c]pyridin-6-yl)-2-(trifluoromethyl)phenoxy)propyl)methanesulfonamide;
6-[4-(3-acetylaminopropoxy)-3-(trifluoromethyl)-phenyl]-1-methyl-1H-imidazo[4,5-c]pyridine-4-carbonitrile;
6-{4-[3-(N-acetyl-N-methylamino)propoxy]-3-(trifluoromethyl)-phenyl}-1-methyl-1H-imidazo[4,5-c]pyridine-4-carbonitrile;
1-methyl-6-(4-(2-(N-acetyl-N-methylamino)ethoxy)-3-(trifluoromethyl)phenyl)-1H-imidazo[4,5-c]pyridine-4-carbonitrile;
1-methyl-6-{4-[(2-(N-ethyl-N-methylamino)-pyridin-4-yl)-methoxy]-3-(trifluoro-methyl)-phenyl}-1H-imidazo[4,5-c]pyridine-4-carbonitrile hydrochloride;
1-methyl-6-(4-(2-(1-(oxazol-2-ylmethyl)piperidin-4-yl)ethoxy)-3-(trifluoro-methyl)phenyl)-1H-imidazo[4,5-c]pyridine-4-carbonitrile hydrochloride;
1-methyl-6-(4-(2-(1-((5-methylisoxazol-3-yl)methyl)piperidin-4-yl)ethoxy)-3-(trifluoromethyl)phenyl)-1H-imidazo[4,5-c]pyridine-4-carbonitrile;
6-(4-(2-(1-((3,5-dimethylisoxazol-4-yl)methyl)piperidin-4-yl)ethoxy)-3-(trifluoromethyl)phenyl)-1-methyl-1H-imidazo[4,5-c]pyridine-4-carbonitrile;
6-(4-(2-(1-(2-dimethylamino-2-oxo-ethyl)piperidin-4-yl)ethoxy)-3-(trifluoromethyl)phenyl)-1-methyl-1H-imidazo[4,5-c]pyridine-4-carbonitrile;
6-(4-(2-(1-(2-fluoroethyl)piperidin-4-yl)ethoxy)-3-(trifluoromethyl)phenyl)-1-methyl-1H-imidazo[4,5-c]pyridine-4-carbonitrile;
6-(4-(2-(1-(2-methoxyethyl)piperidin-4-yl)ethoxy)-3-(trifluoromethyl)phenyl)-1-methyl-1H-imidazo[4,5-c]pyridine-4-carbonitrile;

1-methyl-6-(4-(2-(1-(thiazol-2-ylmethyl)piperidin-4-yl)ethoxy)-3-(trifluoromethyl)phenyl)-1H-imidazo[4,5-c]pyridine-4-carbonitrile;
1-methyl-6-(4-(2-(1-((5-methyl-1,2,4-oxadiazol-3-yl)methyl)piperidin-4-yl)ethoxy)-3-(trifluoromethyl)phenyl)-1H-imidazo[4,5-c]pyridine-4-carbonitrile;
1-methyl-6-(4-(2-(1-((3-methyl-1,2,4-oxadiazol-5-methyl)piperidin-4-yl)ethoxy)-3-(trifluoromethyl)phenyl)-1H-imidazo[4,5-c]pyridine-4-carbonitrile;
1-methyl-6-(4-(2-(1-((5-methyl-1,3,4-oxadiazol-2-methyl)piperidin-4-yl)ethoxy)-3-(trifluoromethyl)phenyl)-1H-imidazo[4,5-c]pyridine-4-carbonitrile;
1-methyl-6-(4-(2-(1-((3-methylisoxazol-5-yl)methyl)piperidin-4-yl)ethoxy)-3-(trifluoromethyl)phenyl)-1H-imidazo[4,5-c]pyridine-4-carbonitrile;
6-(4-(3-acetylaminobenzoxy)-3-(trifluoromethyl)phenyl)-1H-imidazo[4,5-c]pyridine-4-carbonitrile;
6-(4-(2-(1-(2,2-dimethylamino-2-oxoethyl)-4-fluoropiperidin-4-yl)ethoxy)-3-(trifluoromethyl)phenyl)-1-methyl-1H-imidazo[4,5-c]pyridine-4-carbonitrile;
6-(4-(2-(4-fluoro-1-(2-methoxyethyl)piperidin-4-yl)ethoxy)-3-(trifluoromethyl)-phenyl)-1-methyl-1H-imidazo[4,5-c]pyridine-4-carbonitrile;
6-(4-(2-(1-ethyl-4-fluoro-piperidin-4-yl)ethoxy)-3-(trifluoromethyl)phenyl)-1-methyl-1H-imidazo[4,5-c]pyridine-4-carbonitrile;
6-(4-(2-(4-fluoro-1-(2-fluoroethyl)piperidin-4-yl)ethoxy)-3-(trifluoromethyl)phenyl)-1-methyl-1H-imidazo[4,5-c]pyridine-4-carbonitrile; and
6-(4-(2-(4-fluoro-1-methyl-piperidin-4-yl)ethoxy)-3-(trifluoromethyl)phenyl)-1-methyl-1H-imidazo[4,5-c]pyridine-4-carbonitrile;
1-methyl-6-(4-(2-(1-(pyridin-2-yl)piperidin-4-yl)ethoxy)-3-(trifluoromethyl)phenyl)-1H-imidazo[4,5-c]pyridine-4-carbonitrile;
1-methyl-6-(4-(2-(1-(6-methyl-pyridin-2-yl)piperidin-4-yl)ethoxy)-3-(trifluoromethyl)phenyl)-1H-imidazo[4,5-c]pyridine-4-carbonitrile;
N-(2-(4-(4-cyano-1-methyl-1H-imidazo[4,5-c]pyridin-6-yl)-2-(trifluoromethyl)phenoxy)ethyl)-2-(dimethylamino)-N-methylacetamide;
N-(2-(4-(4-cyano-1-methyl-1H-imidazo[4,5-c]pyridin-6-yl)-2-(trifluoromethyl)phenoxy)ethyl)-N-methyl-2-(pyrrolidin-1-yl)acetamide;
(S)—N-(2-(4-(4-cyano-1-methyl-1H-imidazo[4,5-c]pyridin-6-yl)-2-(trifluoromethyl)phenoxy)ethyl)-N,1-dimethylpyrrolidine-2-carboxamide;
2-((1S,4R)-2-azabicyclo[2.2.1]heptan-2-yl)-N-(2-(4-(4-cyano-1-methyl-1H-imidazo[4,5-c]pyridin-6-yl)-2-(trifluoromethyl)phenoxy)ethyl)-N-methylacetamide;
1-methyl-6-(4-(2-(1-(2-(pyrrolidin-1-yl)acetyl)piperidin-4-yl)ethoxy)-3-(trifluoromethyl)phenyl)-1H-imidazo[4,5-c]pyridine-4-carbonitrile; and
1-methyl-6-(4-(2-(1-(2-(dimethylamino)acetyl)piperidin-4-yl)ethoxy)-3-(trifluoromethyl)phenyl)-1H-imidazo[4,5-c]pyridine-4-carbonitrile;
or a pharmaceutically acceptable salt thereof.

The invention provides in a further aspect pharmaceutical compositions comprising a 6-phenyl-1H-imidazo[4,5-c]pyridine-4-carbonitrile derivative having general formula I, or a pharmaceutically acceptable salt thereof, in admixture with one or more pharmaceutically acceptable auxilliaries.

The 6-phenyl-1H-imidazo[4,5-c]pyridine-4-carbonitrile derivatives of general Formula I may be prepared by the methods as depicted in Schemes 1, 2 and 3. N-alkylation of 4-amino-6-chloro-2-cyano-3-nitropyridine (II) produces 4-N-alkylamino-6-chloro-2-cyano-3-nitropyridine (III), from which 4-alkylamino-3-amino-6-chloro-pyridine-2-carbonitrile (IV) is generated following reduction of the nitro group by either hydrogenation (using Pd/C—$H_2$) or by the use of $SnCl_2$ or Fe based reducing agents. Cyclisation of the 3,4-diaminopyridine derivative (IV) with an orthoester catalysed by a Lewis acid, such as ytterbium triflate or a protonic acid, such as acetic acid provides the required imidazopyridine intermediate (V), wherein $R_1$ and $R_2$ have the meaning as defined before.

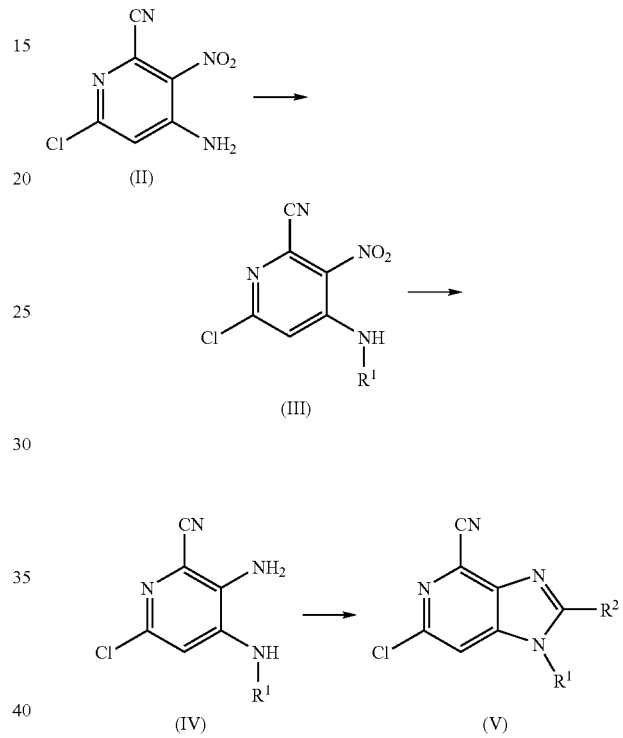

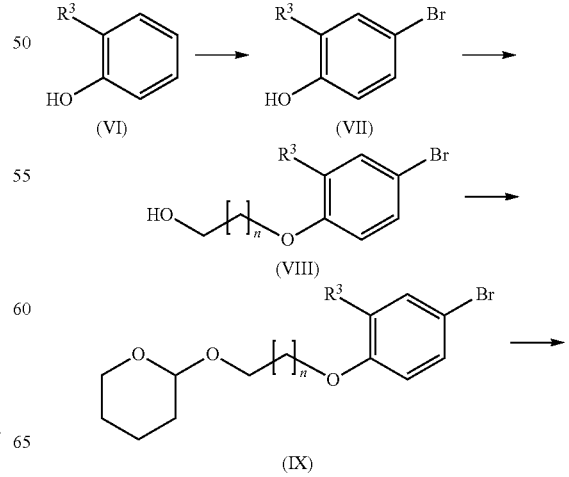

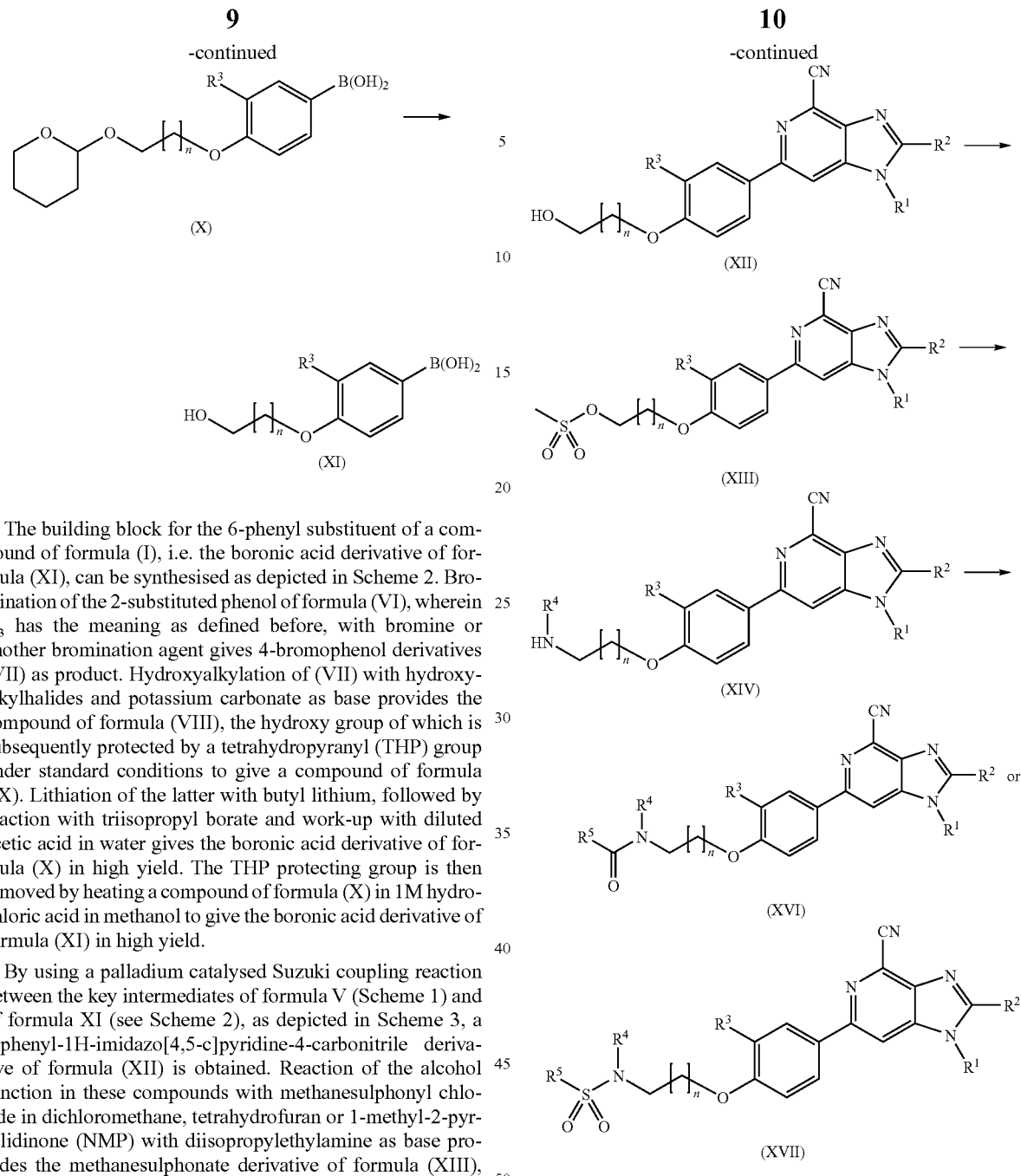

The building block for the 6-phenyl substituent of a compound of formula (I), i.e. the boronic acid derivative of formula (XI), can be synthesised as depicted in Scheme 2. Bromination of the 2-substituted phenol of formula (VI), wherein $R_3$ has the meaning as defined before, with bromine or another bromination agent gives 4-bromophenol derivatives (VII) as product. Hydroxyalkylation of (VII) with hydroxyalkylhalides and potassium carbonate as base provides the compound of formula (VIII), the hydroxy group of which is subsequently protected by a tetrahydropyranyl (THP) group under standard conditions to give a compound of formula (IX). Lithiation of the latter with butyl lithium, followed by reaction with triisopropyl borate and work-up with diluted acetic acid in water gives the boronic acid derivative of formula (X) in high yield. The THP protecting group is then removed by heating a compound of formula (X) in 1M hydrochloric acid in methanol to give the boronic acid derivative of formula (XI) in high yield.

By using a palladium catalysed Suzuki coupling reaction between the key intermediates of formula V (Scheme 1) and of formula XI (see Scheme 2), as depicted in Scheme 3, a 6-phenyl-1H-imidazo[4,5-c]pyridine-4-carbonitrile derivative of formula (XII) is obtained. Reaction of the alcohol function in these compounds with methanesulphonyl chloride in dichloromethane, tetrahydrofuran or 1-methyl-2-pyrrolidinone (NMP) with diisopropylethylamine as base provides the methanesulphonate derivative of formula (XIII), from which on reaction with ammonia or primary amine, a compound of formula (XIV) is obtained. Final compounds XVI and XVII can then be prepared by reacting compounds XIV with either an appropriate acyl chloride, an appropriate isocyanate or a sulphonyl chloride in the presence of a suitable base, such as triethyl amine or sodium bicarbonate.

Scheme 3

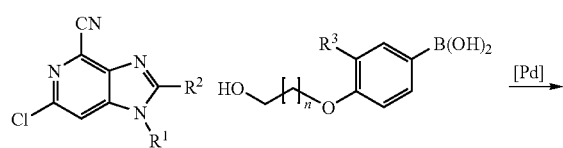

By using a palladium catalysed Suzuki coupling reaction between the key intermediates of formula V (Scheme 1) and of formula XI (see Scheme 2), as depicted in Scheme 3, a 6-phenyl-1H-imidazo[4,5-c]pyridine-4-carbonitrile derivative of formula (XII) is obtained. Reaction of the alcohol function in these compounds with methanesulphonyl chloride in dichloromethane, tetrahydrofuran or 1-methyl-2-pyrrolidinone (NMP) with diisopropylethylamine as base provides the methanesulphonate derivative of formula (XIII), from which on reaction with ammonia or primary amine, a compound of formula (XIV) is obtained. Final compounds XVI and XVII can then be prepared by reacting compounds XIV with either an appropriate acyl chloride, an appropriate isocyanate or a sulphonyl chloride in the presence of a suitable base, such as triethyl amine or sodium bicarbonate.

6-Phenyl-1H-imidazo[4,5-c]pyridine-4-carbonitrile derivatives of general Formula I of the invention can also be prepared via the intermediate phenol derivative of formula (XXI) as shown in Scheme 4. This intermediate is prepared starting from 4-bromo-2-trifluoromethylphenol (VII): following protection of the phenolic hydroxy group as a methoxyethoxymethoxy (MEMO) ether (XVIII), the compound is converted to the boronic acid derivative (formula (XIX)) by standard methodology. Subsequent Suzuki coupling with the compound of formula (V) gives the compound of formula (XX), from which the MEMO group is then removed using dilute aqueous hydrochloric acid. The resulting intermediate compound of formula (XXI) can be derivatised by either alkylation, a Mitsunobu reaction or using further methods known in the art, to prepare additional compounds of formula (XXII), wherein R represents Y—[CH$_2$}$_n$— or a precursor therefor.

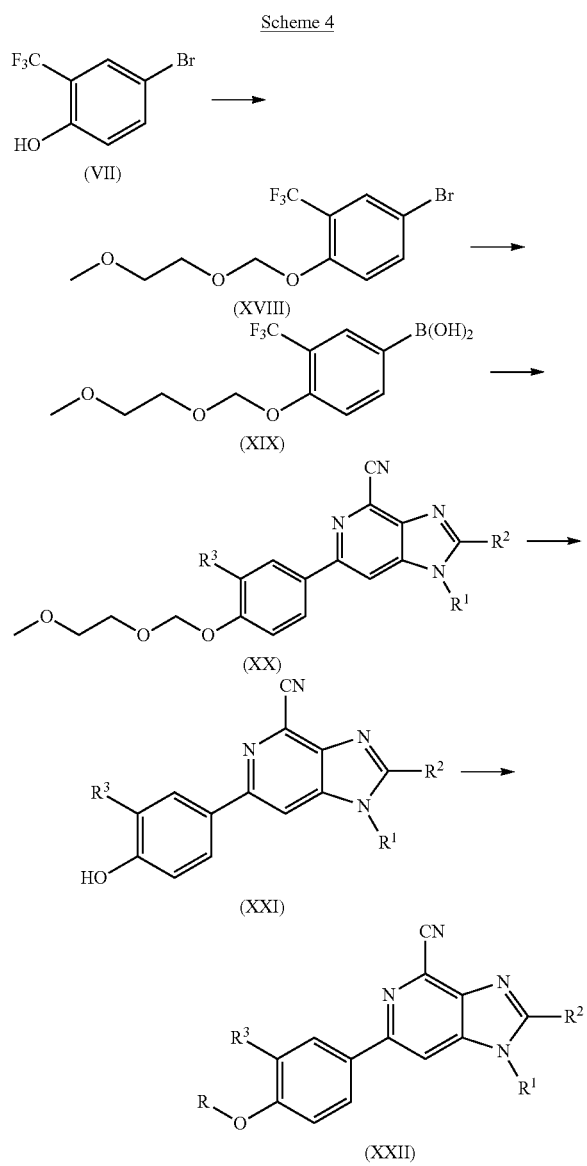

For compound of formula (XXII), wherein R contains a primary or secondary amine, an alcohol or a carboxylic acid, these functionalities may need to be temporarily protected, such as for example by the acid labile t-butyloxycarbonyl (Boc) protecting group. Suitable other protecting groups for functional groups which are to be temporarily protected during syntheses are known in the art, for example from Wuts, P. G. M. and Greene, T. W.: *Protective Groups in Organic Synthesis*, Third Edition, Wiley, New York, 1999.

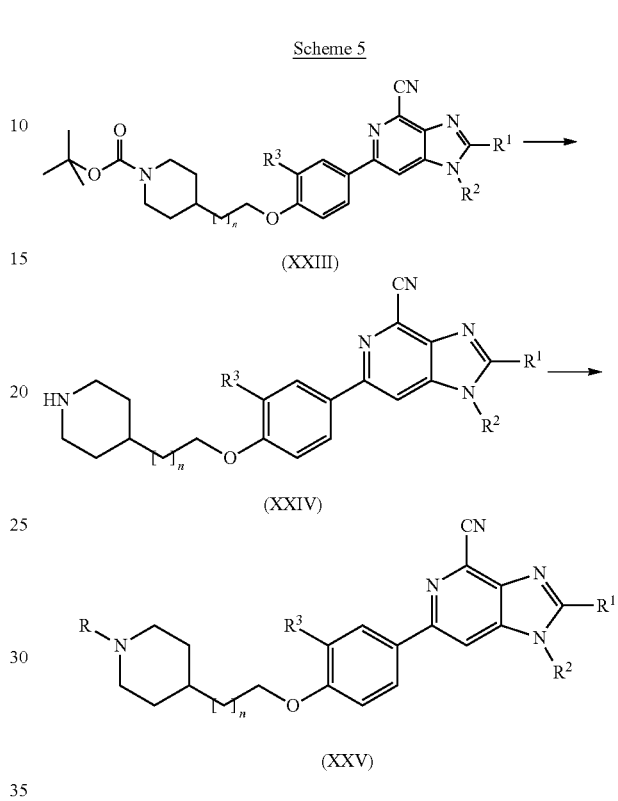

The resulting primary or secondary amine, alcohol or carboxylic acid can be then used for further derivatisation as shown by Scheme 5, such as alkylation or reductive alkylation, arylation, heteroarylation, acylation or sulphonation.

The 6-phenyl-1H-imidazo[4,5-c]pyridine-4-carbonitrile derivatives of the invention, which can be in the form of a free base, may be isolated from the reaction mixture in the form of a pharmaceutically acceptable salt. The pharmaceutically acceptable salts, such as acid addition salts, may further be obtained by treating the free base of Formula I with an organic or inorganic acid such as, but not limited to, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulphonic acid, fumaric acid, succinic acid, tartaric acid, citric acid, benzoic acid and ascorbic acid.

Suitable salts of 6-phenyl-1H-imidazo[4,5-c]pyridine-4-carbonitrile derivatives of Formula I in which a carboxylate group is present can be an alkali metal salts, such as sodium, potassium or lithium salt, or may be a salt obtained from the combination with an organic base, such as trimethylamine, triethylamine and the like.

Compounds of the invention may exist in solvated as well as in unsolvated forms, including hydrated forms. In general, the solvated forms are equivalent to unsolvated forms and are intended to be encompassed within the scope of the present invention. Compounds of the present invention may exist as amorphous forms, but also multiple crystalline forms may be possible. In general, all physical forms are equivalent for the uses contemplated by the present invention and are intended to be within the scope of this invention.

The 6-phenyl-1H-imidazo[4,5-c]pyridine-4-carbonitrile derivatives of the invention and their salts may contain a centre of chirality in one or more of the side chains and may therefore be obtained as a pure enantiomer, or as a mixture of enantiomers, or as a mixture containing diastereomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

The compounds of the invention were found to be inhibitors of human Cathepsin S and of Cathepsin K and can therefore in a further aspect of the invention be used in therapy, and especially for the preparation of a medicament for the treatment of autoimmune disease, chronic obstructive pulmonary disease, pain, cancer, obesity, osteoporosis, atherosclerosis and related Cathepsin S and K dependent disorders, such as rheumatoid arthritis, psoriasis, asthma and IBD.

The compounds of the invention may be administered enterally or parenterally, and for humans preferably in a daily dosage of 0.001-100 mg per kg body weight, preferably 0.01-10 mg per kg body weight. Mixed with pharmaceutically suitable auxilliaries, e.g. as described in the standard reference, Gennaro et al., Remington's Pharmaceutical Sciences, (20th ed., Lippincott Williams & Wilkins, 2000, see especially Part 5: Pharmaceutical Manufacturing) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

Methods
General Chemical Procedures.

All reagents were either purchased from common commercial sources or synthesised according to literature procedures using commercial sources. Proton NMR ($^1$H NMR) were obtained on a Bruker DPX 400 spectrometer and are referenced to internal tetramethylsilane (TMS). Mass spectra were recorded on a Shimadzu LC-8A (HPLC) PE Sciex API 150EX LCMS. Analytical reversed-phase LCMS analysis was carried out on LUNA C18 column (5 μm; 30×4.6 mm) under gradient conditions (90% water/0.1% formic acid to 90% acetonitrile/0.1% formic acid) at a flow rate of 4 ml/min.

Abbreviations

Dimethylformamide (DMF), N-methylpyrrolidinone (NMP), dichloromethane (DCM), dimethylsulfoxide (DMSO), tetrahydrofuran (THF), 1,2-dimethoxyethane (DME), high pressure liquid chromatography (HPLC), diisopropylethylamine (DIPEA), triethylamine (TEA), broad (br), singlet (s), doublet (d), triplet (t), trifluoroacetic acid (TFA), tert-butyloxycarbonyl (Boc), methanesulphonate (MsO), trifluoromethane-sulphonate (TfO), methoxyethoxymethoxy (MEMO), tetrahydropyran (THP), N-chlorosuccinimide (NCS), strong cation exchange resin (SCX), strong anion exchange resin (SAX), deuteriated DMSO (DMSO), deuteriated methanol (CD3OD), deuteriated chloroform (CDCl3), methyl (Me), ethyl (Et), isopropyl (iPr), diisopropyl azodicarboxylate (DIAD).

EXAMPLE 1a

N-(3-(4-(4-cyano-1-methyl-1H-imidazo[4,5-c]pyridin-6-yl)-2-(trifluoromethyl)phenoxy)propyl)methanesulfonamide

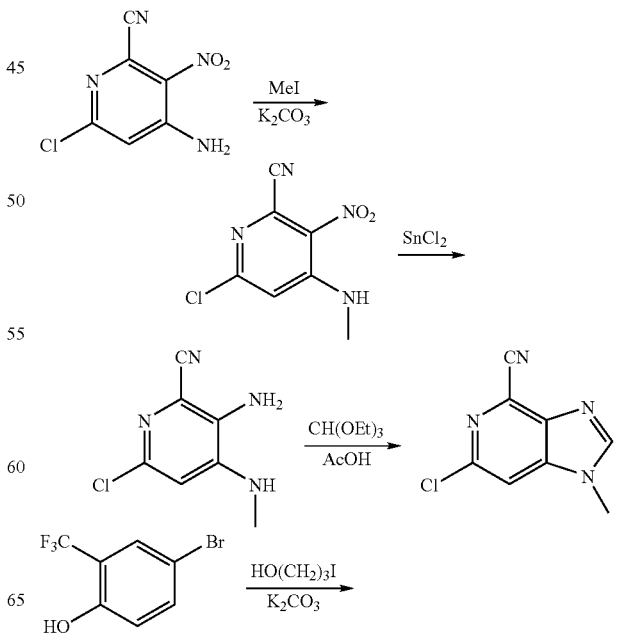

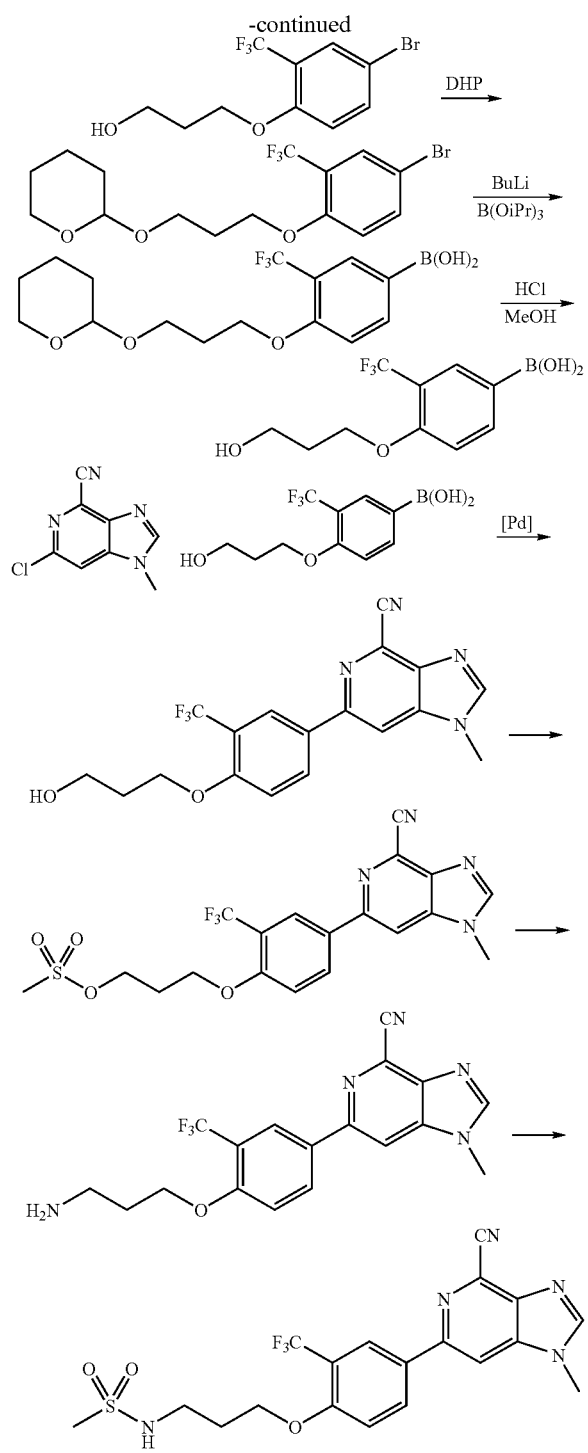

A: 6-Chloro-4-methylamino-3-nitro-pyridine-2-carbonitrile

A stirred mixture of 4-amino-6-chloro-3-nitro-pyridine-2-carbonitrile (12.5 g), potassium carbonate (17.4 g) and iodomethane (22.5 g) in acetonitrile (150 ml) was heated at 80° C. for 3 hours. At this point, another portion of iodomethane (22.5 g) was added; the mixture was heated with stirring for another 2 hours. The mixture was then diluted with ethyl acetate (500 ml) and washed with water (150 ml). The organic layer was then dried over sodium sulphate, solvent removed under reduced pressure to give expected product 4-methylamino-6-chloro-3-nitro-pyridine-2-carbonitrile (13 g).

$^1$H NMR (CD3OD) δ: 7.2 (s, 1H), 3.02 (s, 3H). MS m/z 213 (M+H).

B: 3-Amino-6-chloro-4-methylamino-pyridine-2-carbonitrile

Tin(II) chloride dihydrate (21 g) was added to a suspension of 6-chloro-4-methylamino-3-nitro-pyridine-2-carbonitrile (6.6 g) in ethanol (150 ml). The mixture was stirred at room temperature for 3 hours. To above red-brown coloured solution was then added ethyl acetate (1000 ml) and followed by 10% aqueous ammonium hydroxide (200 ml). The organic layer were seperated, the sticky solid pad was washed with ethyl acetate (5×200 ml). Combined organic layer was then washed with saturated sodium chloride aqueous solution (2×200 ml), dried over sodium sulphate, solvent removed to give a brown solid as expected product (5.7 g).

$^1$H NMR (CD3OD) δ: 6.45 (s, 1H), 2.89 (s, 3H).

C: 6-Chloro-1-methyl-1H-imidazo[4,5-c]pyridine-4-carbonitrile

The suspension of 3-amino-6-chloro-4-methylamino-pyridine-2-carbonitrile (1.8 g) in DCM (5 ml), acetic acid (1.5 ml) and triethyl orthoformate (10 ml) was heated in microwave at 150° C. for 30 minutes. The mixture was then diluted with ethyl acetate (200 ml), washed with 10% sodium carbonate (100 ml), dried over sodium sulphate, solvent removed under reduced pressure, DCM (5 ml) was then added to the residue, some product crashed out and collected by filtration (0.5 g), the rest was then columned on silica gel using ethyl acetate-heptane (55:45) as eluant to give another 0.8 g of expected product (a total of 1.3 g product). $^1$H NMR (CDCl3) δ: 8.1 (s, 1H), 7.6 (s, 1H), 3.93 (s, 3H). MS m/z 193 (M+H).

D: 3-(4-Bromo-2-(trifluoromethyl)-phenoxy)propan-1-ol

3-Iodopropanol (11.23 g) was added to a mixture of 4-bromo-2-(trifluoromethyl)-phenol (15 g) and potassium carbonate (172 g) in acetonitrile (150 ml). The above mixture was refluxed for 4 hours then diluted with ethyl acetate (500 ml) and water (300 ml). Organic layer was seperated, dried over magnesium sulphate, solvent removed under reduced pressure to give expected product clean enough for use at the next step (18.6 g). $^1$H NMR (CDCl3) δ: 7.67 (d, 1H), 7.58 (dd, 1H), 6.90 (dd, 1H), 4.18 (t, 2H), 3.87 (q, 2H), 2.07 (tt, 2H).

E: 2-[3-(4-Bromo-2-(trifluoromethyl)-phenoxy)-propoxy]-tetrahydro-2H-pyran

A mixture of 3-(4-bromo-2-(trifluoromethyl)-phenoxy)propan-1-ol (12 g), 3,4-dihydro-2H-puran (6.75 g) and p-toluenesulfonic acid hydrate (0.76 g) in THF (100 ml) was stirred at room temperature for 1 hour then diluted with 10% sodium carbonate (50 ml) and extracted with ethyl acetate (2×150 ml). Organic layer was then dried over sodium sulphate, solvent removed under reduced pressure to give expected product (15 g). $^1$H NMR (CDCl$_3$) δ: 7.67 (d, 1H), 7.56 (dd, 1H), 6.90 (dd, 1H), 4.56 (dd, 1H), 4.15 (t, 2H), 3.75-4.0 (m, 2H), 3.4-3.65 (m, 2H), 2.10 (m, 2H), 1.4-2.0 (m, 6H).

F: 4-(3-(Tetrahydro-2H-pyran-2-yloxy)-propoxy)-3-(trifluoromethyl)-phenylboronic acid BuLi (2.5M, 19.1 ml) was added dropwise to a solution of 2-(3-(4-bromo-2-(trifluoromethyl)phenoxy)propoxy)tetrahydro-2H-pyran (16.6 g) in THF at −78° C. under N2 during 3 minutes. After stirring at −78° C. for another 10 minutes, triisopropyl borate (11 ml) was then added dropwise during 3 minutes at −78° C. The mixture was stirred at −78° C. for further 20 minutes, then warmed up to room temperature slowly and stirred at room temperature for 30 minutes. The mixture was then quenched with acetic acid (10% in water, 20 ml), extracted with EtOAc (200 ml), washed with brine (100 ml×5), dried over sodium sulphate, solvent removed under reduced pressure, the residue was taken in to toluene and then solvent removed under vacuum to take out trace of acetic acid (repeat 3 times, until no acetic acid smell). The product, as shown by NMR, contains 3 sets of product peaks assumed to be monomer, dimer and trimer.
$^1$H NMR (CDCl3) δ: 7.8-8.4 (3xs and 3xd, 2H), 6.9-7.2 (3xd, 1H), 4.6 (m, 1H), 3.4-4.3 (m, 6H), 2.1-2.3 (m, 2H), 1.4-1.9 (m, 6H).

G: 4-(3-Hydroxypropoxy)-3-(trifluoromethyl)-phenylboronic acid 4-(3-(Tetrahydro-2H-pyran-2-yloxy)propoxy)-3-(trifluoromethyl)phenylboronic acid (30.6 g) was added to hydrochloric acid (1M in MeOH) and the mixture was heated at 50° C. for 40 minutes. Solvent and HCl were then removed under reduced pressure and residue (20.3 g) was used for next step without further purification. Proton NMR indicates 2 sets of product peaks assumed to be monomer and dimer or trimer.
$^1$H NMR (CDCl3 (0.7 ml)+CD3OD (0.2 ml)) δ: 7.7-8.0 (2xd and 2xs, 2H), 7.0 (2xd, 1H), 4.22 (t, 2H), 3.86 (t, 2H), 3.48 (tt, 2H).

H: 6-[4-(3-Hydroxypropoxy)-3-(trifluoromethyl)-phenyl]-1-methyl-1H-imidazo[4,5-c]pyridine-4-carbonitrile A mixture of 6-chloro-1-methyl-1H-imidazo[4,5-c]pyridine-4-carbonitrile (6 g), 4-(3-hydroxypropoxy)-3-(trifluoromethyl)phenylboronic acid (12.3 g), tris(dibenzylideneacetone)dipalladium (1.42 g), tricyclohexylphosphine (1.05 g) and tribasic potassium phosphate (13.2 g) in dioxane (60 ml) and water (24 ml) was heated at 100° C. under N2 for 4 hours. The mixture was then diluted with ethyl acetate (400 ml), organic layer seperated and solvent removed under reduced pressure, to the residue was then added methanol (50 ml), product crystalised out and collected by filtration (7.7 g). $^1$H NMR (DMSO) δ: 8.67 (s, 1H), 8.60 (s, 1H), 8.43 (d, 1H), 8.37 (s, 1H), 7.41 (d, 1H), 4.55 (t, 1H), 4.25 (t, 2H), 3.99 (s, 3H), 3.58 (q, 2H), 1.92 (tt, 2H). MS m/z 377 (M+H).

I: 3-[4-(4-Cyano-1-methyl-1H-imidazo[4,5-c]pyridin-6-yl)-2-(trifluoromethyl)phenoxy]propyl methanesulfonate Methanesulphonyl chloride (2.65 g) was added dropwise to a solution of 6-[4-(3-hydroxypropoxy)-3-(trifluoromethyl)-phenyl]-1-methyl-1H-imidazo[4,5-c]pyridine-4-carbonitrile (6.7 g) and diisopropylethylamine (9.7 ml) in NMP (40 ml). The mixture was stirred at room temperature for 3 hours. After adding ice (100 g), solid product was collected by filtration, washed with cold ethanol (20 ml) to give 3-[4-(4-cyano-1-methyl-1H-imidazo[4,5-c]pyridin-6-yl)-2-(trifluoromethyl)phenoxy]propyl methane-sulfonate (7.4 g). $^1$H NMR (DMSO) δ: 8.69 (s, 1H), 8.62 (s, 1H), 8.45 (d, 1H), 8.41 (s, 1H), 7.47 (d, 1H), 4.40 (t, 1H), 4.32 (t, 2H), 3.99 (s, 3H), 3.18 (s, 3H), 2.21 (tt, 2H).

J: 6-[4-(3-Aminopropoxy)-3-(trifluoromethyl)-phenyl]-1-methyl-1H-imidazo[4,5-c]pyridine-4-carbonitrile A mixture of 3-[4-(4-cyano-1-methyl-1H-imidazo[4,5-c]pyridin-6-yl)-2-(trifluoromethyl)phenoxy]propyl methane-sulfonate (500 mg), and ammonia in methanol (7M, 10 ml) was heated at 120° C. under microwave conditions for 20 minutes. After removal of solvent under vacuum, the expected product 6-[4-(3-aminopropoxy)-3-(trifluoromethyl)-phenyl]-1-methyl-1H-imidazo[4,5-c]pyridine-4-carbonitrile was obtained as methanesulphonic acid salt. $^1$H NMR (CD3OD) δ: 8.44 (s, 1H), 8.35-8.42 (m, 3H), 7.36 (d, 1H), 4.32 (t, 2H), 4.02 (s, 3H), 3.23 (t, 2H), 2.25 (m, 2H).

K: N-(3-(4-(4-cyano-1-methyl-1H-imidazo[4,5-c]pyridin-6-yl)-2-(trifluoromethyl)-phenoxy)propyl)methanesulfonamide Methanesulphonyl chloride (31 mg) was added to the solution of 6-[4-(3-Aminopropoxy)-3-(trifluoromethyl)-phenyl]-1-methyl-1H-imidazo[4,5-c]pyridine-4-carbonitrile (20 mg) in DCM (1 ml) containing DIPEA (44 uL). The mixture was stirred at rt for 1 hour, then solvent removed under vacuum and residue dissolved in NMP (1 ml) and purified by HPLC to give expected product, N-(3-(4-(4-cyano-1-methyl-1H-imidazo[4,5-c]pyridin-6-yl)-2-(trifluoromethyl)phenoxy)propyl)methanesulfonamide.
$^1$H NMR (DMSO) δ: 8.72 (s, 1H), 8.64 (s, 1H), 8.45 (d, 1H), 8.41 (s, 1H), 7.44 (d, 1H), 7.11 (t, 1H, NH), 4.26 (t, 2H), 3.99 (s, 3H), 3.14 (q, 2H), 2.89 (s, 3H), 1.97 (m, 2H), MS m/z 454 (M+H).

The procedure described in Example is was further applied, using the appropriate acylation agent, to prepare the following compounds:

1b: 6-[4-(3-acetylaminopropoxy)-3-(trifluoromethyl)-phenyl]-1-methyl-1H-imidazo[4,5-c]pyridine-4-carbonitrile

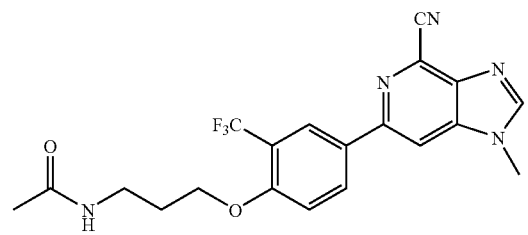

¹H NMR (CDCl₃) δ: 8.25-8.35 (m, 2H), 8.10 (s, 1H), 7.89 (s, 1H), 7.15 (d, 1H), 6.05 (b, 1H, NH), 4.24 (t, 2H), 4.00 (s, 3H), 3.53 (q, 2H), 2.11 (m, 2H), 2.00 (s, 3H). MS m/z 418 (M+H).

1c: 6-[4-(3-(dimethylaminocarbonylamino)propoxy)-3-(trifluoromethyl)-phenyl]-1-methyl-1H-imidazo[4,5-c]pyridine-4-carbonitrile

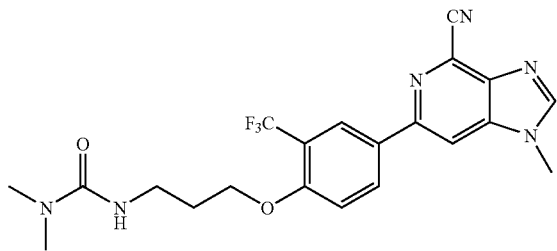

¹H NMR (CDCl3) δ: 8.20-8.23 (m, 2H), 8.10 (s, 1H), 7.86 (s, 1H), 7.15 (d, 1H), 4.9 (b, 1H, NH), 4.22 (t, 2H), 3.99 (s, 3H), 3.50 (q, 2H), 2.92 (s, 6H), 2.10 (m, 2H). MS m/z 447 (M+H).

1d: 6-[4-(3-(cyclopropylcarbonylamino)propoxy)-3-(trifluoromethyl)-phenyl]-1-methyl-1H-imidazo[4,5-c]pyridine-4-carbonitrile

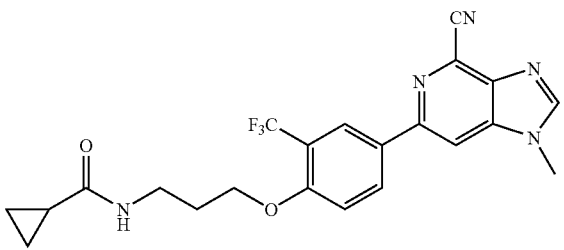

¹H NMR (CDCl3) δ: 8.26 (d, 1H), 8.24 (s, 1H), 8.09 (s, 1H), 7.87 (s, 1H), 7.14 (d, 1H), 6.25 (b, 1H, NH), 4.24 (t, 2H), 3.99 (s, 3H), 3.54 (q, 2H), 2.12 (m, 2H), 1.39 (m, 1H), 0.97 (m, 2H), 0.74 (m, 2H). MS m/z 444 (M+H).

EXAMPLE 2a

6-{4-[3-(N-acetyl-N-methylamino)propoxy]-3-(trifluoromethyl)-phenyl}-1-methyl-1H-imidazo[4,5-c]pyridine-4-carbonitrile

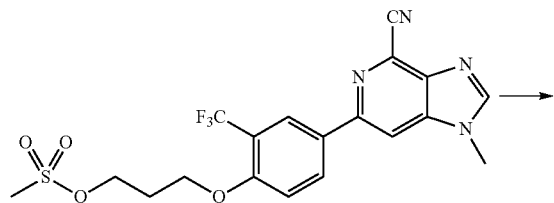

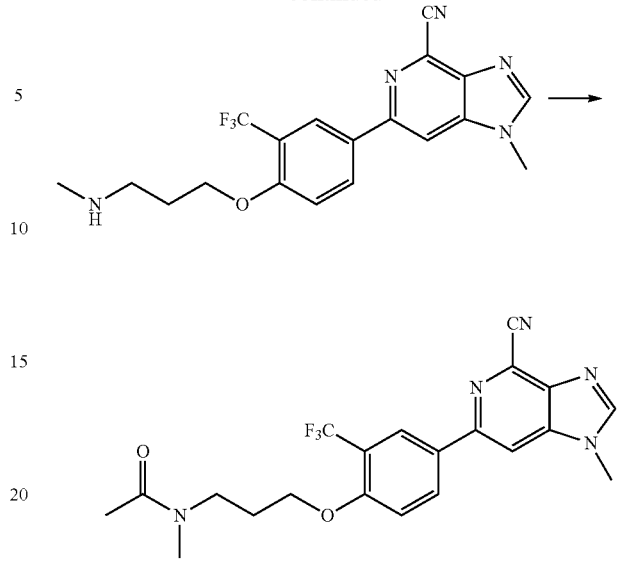

A: 1-methyl-6-(4-(3-(methylamino)propoxy)-3-(trifluoromethyl)phenyl)-1H-imidazo[4,5-c]pyridine-4-carbonitrile Methylamine (2M in THF, 0.825 ml) was added to 3-(4-(4-cyano-1-methyl-1H-imidazo[4,5-c]pyridin-6-yl)-2-(trifluoromethyl)phenoxy)propyl methanesulfonate (150 mg) dissolved in NMP (1 ml). The reaction mixture was heated at 100° C. under microwave conditions for 20 minutes. The reaction mixture was filtered and then purified by acidic prep HPLC to give 1-methyl-6-(4-(3-(methylamino)propoxy)-3-(trifluoromethyl)phenyl)-1H-imidazo[4,5-c]pyridine-4-carbonitrile as a TFA salt. The above TFA salt was then dissolved in MeOH (3 ml) and passed through a strong cation exchange (SCX) column. After washing with methanol to remove TFA residue, product was washed out with 2M ammonia in methanol. After removal of solvent, the free base of 1-methyl-6-(4-(3-(methylamino)propoxy)-3-(trifluoromethyl)phenyl)-1H-imidazo[4,5-c]pyridine-4-carbonitrile was obtained (80 mg).

¹H NMR (MeOD) δ: 8.45 (s, 1H), 8.34-8.30 (m, 2H), 7.30 (d, 1H), 4.25 (t, 2H), 4.01 (s, 3H), 2.81 (t, 2H), 2.42 (s, 3H), 2.05 (m, 2H). MS m/z 390.2 (M+H).

B: 6-{4-[3-(N-acetyl-N-methylamino)propoxy]-3-(trifluoromethyl)-phenyl}-1-methyl-1H-imidazo[4,5-c]pyridine-4-carbonitrile Acetyl chloride (0.011 ml) was added dropwise to a solution of 1-methyl-6-(4-(3-(methylamino)propoxy)-3-(trifluoromethyl)phenyl)-1H-imidazo[4,5-c]pyridine-4-carbonitrile (20 mg) and diisopropylethylamine (0.045 ml) in THF (2 ml). The reaction mixture was stirred at room temperature for 1 hour. The product was then purified by acidic prep HPLC to give 6-{-4-[3-(N-acetyl-N-methylamino)propoxy]-3-(trifluoromethyl)phenyl}-1-methyl-1H-imidazo[4,5-c]pyridine-4-carbonitrile (9.2 mg).

¹H NMR (MeOD) δ: 8.42 (s, 1H), 8.40-8.35 (m, 3H), 7.30 (t, 1H), 4.21 (t, 2H), 4.02 (s, 3H), 3.66-3.60 (m, 2H), 3.10+2.96 (2xs, 3H), 2.20-2.10 (m, 5H). MS m/z 432 (M+H).

The procedure described in Example 2a was further applied, using the appropriate acid chloride to prepare the following compounds:

2b: 6-{4-[3-(N-propionyl-N-methylamino)propoxy]-3-(trifluoromethyl)-phenyl}-1-methyl-1H-imidazo[4,5-c]pyridine-4-carbonitrile

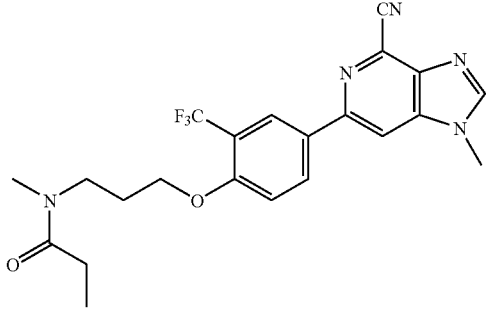

¹H NMR (MeOD) δ: 8.42 (s, 1H), 8.40-8.35 (m, 3H), 7.30 (t, 1H), 4.21 (t, 2H), 4.02 (s, 3H), 3.66-3.60 (m, 2H), 3.08 (s, 3H), 2.48-2.39 (m, 2H), 2.20-2.05 (m, 2H), 1.11-1.09 (m, 3H). MS m/z 446 (M+H).

2c: 6-{4-[3-(N-isobutyryl-N-methylamino)propoxy]-3-(trifluoromethyl)-phenyl}-1-methyl-1H-imidazo[4,5-c]pyridine-4-carbonitrile

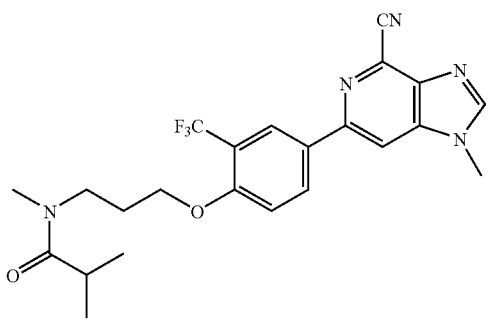

¹H NMR (MeOD) δ: 8.44 (s, 1H), 8.39-8.30 (m, 3H), 7.30 (t, 1H), 4.24-4.18 (m, 2H), 4.02 (s, 3H), 3.70 (t, 1H), 3.60 (t, 1H), 3.14+2.96 (2xs, 3H), 3.00-2.90 (m, 1H), 2.20-2.05 (m, 2H), 1.10-1.04 (dd, 6H). MS m/z 460 (M+H).

2d: N-(3-(4-(4-cyano-1-methyl-1H-imidazo[4,5-c]pyridine-6-yl)-2-(trifluoromethyl)phenoxy)propyl)-N-methylpyrrolidine-1-carboxamide

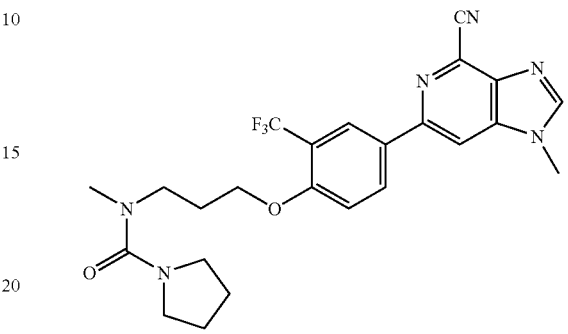

¹H NMR (MeOD) δ: 8.44 (s, 1H), 8.37-8.30 (m, 3H), 7.30 (d, 1H), 4.21 (t, 2H), 4.02 (s, 3H), 3.45 (t, 2H), 3.35-3.30 (m, 4H), 2.89 (s, 3H), 2.16-2.10 (m, 2H), 1.82 (m, 4H). MS m/z 487 (M+H).

EXAMPLE 3a

6-{4-[3-(N-acetyl-N-cyclopropylamino)propoxy]-3-(trifluoromethyl)-phenyl}-1-methyl-1H-imidazo[4,5-c]pyridine-4-carbonitrile

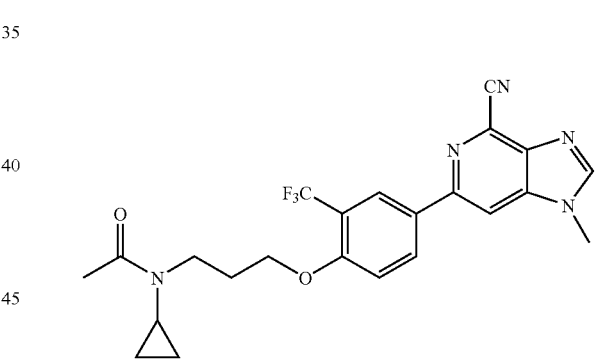

A: 6-(4-(3-(cyclopropylamino)propoxy)-3-(trifluoromethyl)phenyl)-1H-imidazo[4,5-c]pyridine-4-carbonitrile Cyclopropanamine (0.114 ml) was added to 3-(4-(4-cyano-1-methyl-1H-imidazo[4,5-c]pyridin-6-yl)-2-(trifluoromethyl)phenoxy)propyl methanesulfonate (150 mg) dissolved in NMP (1 ml). The reaction mixture was heated at 100° C. under microwave conditions for 20 minutes. The reaction mixture was filtered and then purified by acidic prep HPLC to give 6-(4-(3-(cyclopropylamino)propoxy)-3-(trifluoromethyl)phenyl)-1H-imidazo[4,5-c]pyridine-4-carbonitrile as a TFA salt. The above TFA salt was then dissolved in MeOH (3 ml) and passed through a strong cation exchange (SCX) column. After washing with methanol to remove TFA residue, product was washed out with 2M ammonia in methanol. After removal of solvent, the free base of 6-(4-(3-(cyclopropylamino)propoxy)-3-(trifluoromethyl)phenyl)-1H-imidazo[4,5-c]pyridine-4-carbonitrile was obtained (84 mg).

$^1$H NMR (MeOD) δ: 8.45 (s, 1H), 8.34-8.30 (m, 2H), 7.30 (d, 1H), 4.25 (t, 2H), 4.01 (s, 3H), 2.81 (t, 2H), 2.71-2.69 (m, 2H), 2.10 (t, 2H), 1.17 (t, 3H). MS m/z 404.2 (M+H).

B: 6-{4-[3-(N-acetyl-N-cyclopropylamino)propoxy]-3-(trifluoromethyl)-phenyl}-1-methyl-1H-imidazo[4,5-c]pyridine-4-carbonitrile Acetyl chloride (0.010 ml) was added dropwise to a solution of 6-(4-(3-(cyclopropylamino)propoxy)-3-(trifluoromethyl)phenyl)-1H-imidazo[4,5-c]pyridine-4-carbonitrile (20 mg) and diisopropylethylamine (0.042 ml) in THF (2 ml). The reaction mixture was stirred at room temperature for 1 hour. The product was then purified by acidic prep HPLC to give 6-{4-[3-(N-acetyl-N-cyclopropylamino)propoxy]-3-(trifluoromethyl)-phenyl}-1-methyl-1H-imidazo[4,5-c]pyridine-4-carbonitrile.

$^1$H NMR (DMSO) δ: 8.71 (s, 1H), 8.64 (s, 1H), 8.45-8.41 (m, 2H), 7.30 (d, 1H), 422-4.19 (t, 2H), 3.99 (s, 3H), 3.41 (m, 2H), 2.75 (m, 1H), 2.11 (s, 3H), 1.99-1.95 (m, 2H), 0.80-0.70 (m, 4H). MS m/z 458 (M+H).

The procedure described in Example 3a was further applied, using the appropriate acid chloride to prepare the following compounds:

3b: 6-{4-[3-(N-propionyl-N-cyclopropylamino)propoxy]-3-(trifluoromethyl)-phenyl}-1-methyl-1H-imidazo[4,5-c]pyridine-4-carbonitrile $^1$H NMR (DMSO) δ: 8.71 (s, 1H), 8.64 (s, 1H), 8.45-8.41 (m, 2H), 7.30 (d, 1H), 4.22-4.19 (t, 2H), 3.99 (s, 3H), 3.41 (m, 2H), 2.75 (m, 1H), 2.51 (m, 2H), 2.00-1.98 (m, 2H) 1.01 (t, 3H), 0.85-0.70 (m, 4H). MS m/z 472 (M+H).

3c: 6-{4-[3-(N-isobutyryl-N-cyclopropylamino)propoxy]-3-(trifluoromethyl)-phenyl}-1-methyl-1H-imidazo[4,5-c]pyridine-4-carbonitrile $^1$H NMR (DMSO) δ: 8.71 (s, 1H), 8.64 (s, 1H), 8.45-8.41 (m, 2H), 7.42 (d, 1H), 4.22-4.19 (t, 2H), 3.99 (s, 3H), 3.49 (m, 2H), 3.30 (m, 1H), 2.80 (m, 1H), 1.02 (t, 6H), 0.85-0.70 (m, 4H). MS m/z 486 (M+H).

EXAMPLE 4a

6-{4-[3-(N-acetyl-N-ethylamino)propoxy]-3-(trifluoromethyl)-phenyl}-1-methyl-1H-imidazo[4,5-c]pyridine-4-carbonitrile

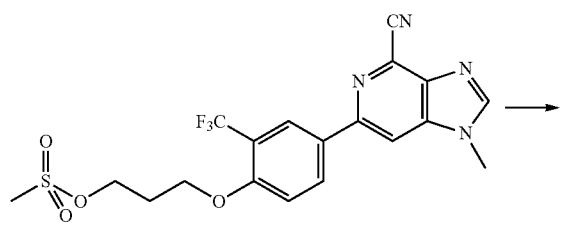

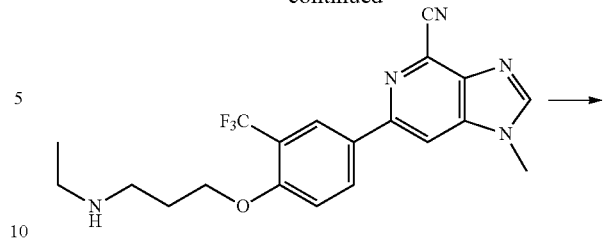

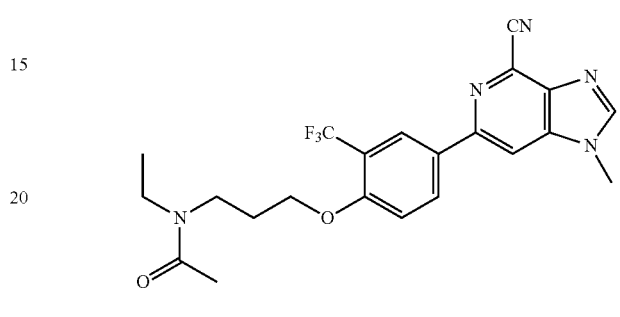

A: 6-(4-(3-(ethylamino)propoxy)-3-(trifluoromethyl)phenyl)-1H-imidazo[4,5-c]pyridine-4-carbonitrile Ethylamine (2M in THF, 0.825 ml) was added to 3-(4-(4-cyano-1-methyl-1H-imidazo[4,5-c]pyridin-6-yl)-2-(trifluoromethyl)phenoxy)propyl methanesulfonate (150 mg) dissolved in NMP (1 ml). The reaction mixture was heated at 100° C. under microwave conditions for 20 minutes. The reaction mixture was filtered and then purified by acidic prep HPLC to give 6-(4-(3-(ethylamino)propoxy)-3-(trifluoromethyl)-phenyl)-1H-imidazo[4,5-c]pyridine-4-carbonitrile as a TFA salt. The above TFA salt was then dissolved in MeOH (3 ml) and passed through a strong cation exchange (SCX) column. After washing with methanol to remove TFA residue, product was washed out with 2M ammonia in methanol. After removal of solvent, the free base of 6-(4-(3-(ethylamino)propoxy)-3-(trifluoromethyl)phenyl)-1H-imidazo[4,5-c]pyridine-4-carbonitrile was obtained (71 mg). $^1$H NMR (MeOD) δ: 8.45 (s, 1H), 8.34-8.30 (m, 2H), 7.30 (d, 1H), 4.25 (t, 2H), 4.01 (s, 3H), 2.81 (t, 2H), 2.71-2.69 (m, 2H), 2.10 (t, 2H), 1.17 (t, 3H). MS m/z 404.2 (M+H).

B: 6-{4-[3-(N-acetyl-N-ethylamino)propoxy]-3-(trifluoromethyl)-phenyl}-1-methyl-1H-imidazo[4,5-c]pyridine-4-carbonitrile Acetyl chloride (0.009 ml) was added dropwise to a solution of 6-(4-(3-(ethylamino)propoxy)-3-(trifluoromethyl)phenyl)-1H-imidazo[4,5-c]pyridine-4-carbonitrile (17.5 mg) and diisopropylethylamine (0.034 ml) in THF (2 ml). The reaction mixture was stirred at room temperature for 1 hour. The product was then purified by acidic prep HPLC to 6-{4-[3-(N-acetyl-N-ethylamino)propoxy]-3-(trifluoromethyl)-phenyl}-1-methyl-1H-imidazo[4,5-c]pyridine-4-carbonitrile. $^1$H NMR (MeOD) δ: 8.43 (s, 1H), 8.34-8.30 (m, 2H), 7.30 (t, 1H), 4.25-4.18 (m, 2H), 4.02 (s, 3H), 3.52-3.63 (m, 2H), 3.45 (q, 2H), 2.20-2.11 (m, 5H), 1.22+1.15 (2xt, 3H). MS m/z 446 (M+H).

The procedure described in Example 4a was further applied, using the appropriate acid chloride to prepare the following compounds:

4b: 6-{4-[3-(N-Ethyl-N-propionylamino)propoxy]-3-(trifluoromethyl)-phenyl}-1-methyl-1H-imidazo[4,5-c]pyridine-4-carbonitrile ¹H NMR (MeOD) δ: 8.44 (s, 1H), 8.34-8.30 (m, 2H), 7.30 (t, 1H), 4.25-4.18 (m, 2H), 4.02 (s, 3H), 3.63-3.51 (m, 2H), 3.45 (q, 2H), 2.43 (q, 2H), 2.20-2.10 (m. 2H), 1.21-1.11 (m, 6H). MS m/z 460 (M+H).

4c: 6-{4-[3-(N-Ethyl-N-isobutyrylamino)propoxy]-3-(trifluoromethyl)-phenyl}-1-methyl-1H-imidazo[4,5-c]pyridine-4-carbonitrile ¹H NMR (MeOD) δ: 8.44 (s, 1H), 8.35-8.30 (m, 2H), 7.30 (t, 1H), 4.25-4.18 (m, 2H), 4.02 (s, 3H), 3.63-3.51 (m, 2H), 3.45 (q, 2H), 3.00-2.89 (m, 1H), 2.20-2.05 (m, 2H), 1.23-1.05 (m, 9H). MS m/z 474 (M+H).

4d: N-(3-(4-(4-cyano-1-methyl-1H-imidazo[4,5-c]pyridine-6-yl)-2-(trifluoromethyl)phenoxy)propyl)-N-ethylpyrrolidine-1-carboxamide

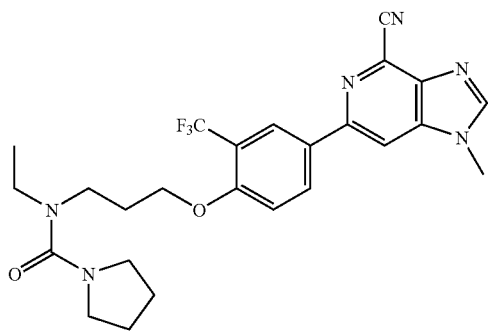

¹H NMR (MeOD) δ: 8.44 (s, 1H), 8.35-8.30 (m, 2H), 7.30 (t, 1H), 4.25-4.18 (m, 2H), 4.02 (s, 3H), 3.50 (t, 2H), 3.40-3.20 (m, 4H), 2.20-2.10 (m, 2H), 1.90 (m, 4H), 1.07 (t, 3H). MS m/z 474 (M+H).

EXAMPLE 5a

6-{4-[3-(N-acetyl-N-isopropylamino)propoxy]-3-(trifluoromethyl)-phenyl}-1-methyl-1H-imidazo[4,5-c]pyridine-4-carbonitrile

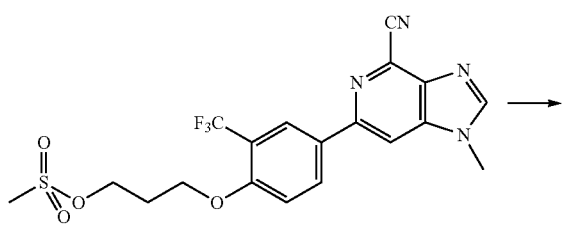

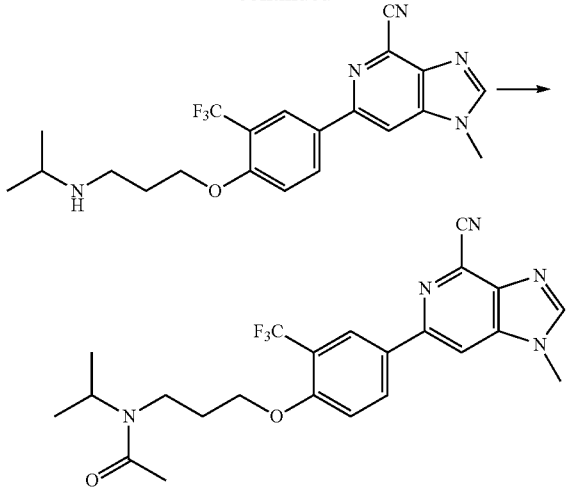

A: 6-(4-(3-(isopropylamino)propoxy)-3-(trifluoromethyl)phenyl)-1-methyl-1H-imidazo[4,5-c]pyridine-4-carbonitrile Propan-2-amine (0.141 ml) was added to 3-(4-(4-cyano-1-methyl-1H-imidazo[4,5-c]pyridin-6-yl)-2-(trifluoromethyl)phenoxy)propyl methanesulfonate (150 mg) dissolved in NMP (1 ml). The reaction mixture was heated at 100° C. under microwave conditions for 20 minutes. The reaction mixture was filtered and then purified by acidic prep HPLC to give 6-(4-(3-(isopropylamino)propoxy)-3-(trifluoromethyl)phenyl)-1-methyl-1H-imidazo[4,5-c]pyridine-4-carbonitrile as a TFA salt. The above TFA salt was then dissolved in MeOH (3 ml) and passed through a strong cation exchange (SCX) column. After washing with methanol to remove TFA residue, product was washed out with 2M ammonia in methanol. After removal of solvent, the free base of 6-(4-(3-(isopropylamino)propoxy)-3-(trifluoromethyl)phenyl)-1-methyl-1H-imidazo[4,5-c]pyridine-4-carbonitrile (65 mg). ¹H NMR (MeOD) δ: 8.41 (s, 1H), 8.34-8.30 (m, 3H), 7.30 (d, 1H), 4.25 (t, 2H), 4.01 (s, 3H), 2.88 (m, 3H), 2.10 (q, 2H), 1.14 (d, 6H). MS m/z 418.2 (M+H).

B: 6-{4-[3-(N-acetyl-N-isopropylamino)propoxy]-3-(trifluoromethyl)-phenyl}-1-methyl-1H-imidazo[4,5-c]pyridine-4-carbonitrile Acetyl chloride (0.008 ml) was added dropwise to a solution of 6-(4-(3-(isopropylamino)propoxy)-3-(trifluoromethyl)phenyl)-1H-imidazo[4,5-c]pyridine-4-carbonitrile (15 mg) and diisopropylethylamine (0.031 ml) in THF (2 ml). The reaction mixture was stirred at room temperature for 1 hour. The product was then purified by acidic prep HPLC to give 6-{4-[3-(N-acetyl-N-isopropylamino)propoxy]-3-(trifluoromethyl)-phenyl}-1-methyl-1H-imidazo[4,5-c]pyridine-4-carbonitrile. ¹H NMR (DMSO) δ: 8.72 (s, 1H), 8.64 (s, 1H), 8.46-8.42 (m, 2H), 7.43 (t, 1H), 3.99 (s, 3H), 3.40+ 3.28 (2xt, 1H), 2.04-1.96 (m, 3H), 1.16-1.10 (dd, 6H). MS m/z 460 (M+H).

The procedure described in Example 5a was further applied, using the appropriate acid chloride to prepare the following compound:

5b: 6-{4-[3-(N-isopropyl-N-propionylamino)propoxy]-3-(trifluoromethyl)-phenyl}-1-methyl-1H-imidazol-[4,5-c]pyridine-4-carbonitrile ¹H NMR (MeOD) δ: 8.43-8.30 (m, 4H), 7.43 (t, 1H), 3.99 (s, 3H), 4.40 (m, 1H), 4.23-4.15 (m, 3H), 4.02 (s, 3H), 3.6-3.4

(2xt, 2H), 2.47-2.45 (q, 2H), 2.20-2.10 (m, 2H), 1.26-1.21 (2xd, 6H), 1.15 (t, 3H) MS m/z 474 (M+H).

EXAMPLE 6a

N-(3-(4-(4-cyano-1-methyl-1H-imidazo[4,5-c]pyridin-6-yl)-2-(trifluoromethyl)phenoxy)ethyl)methanesulfonamide

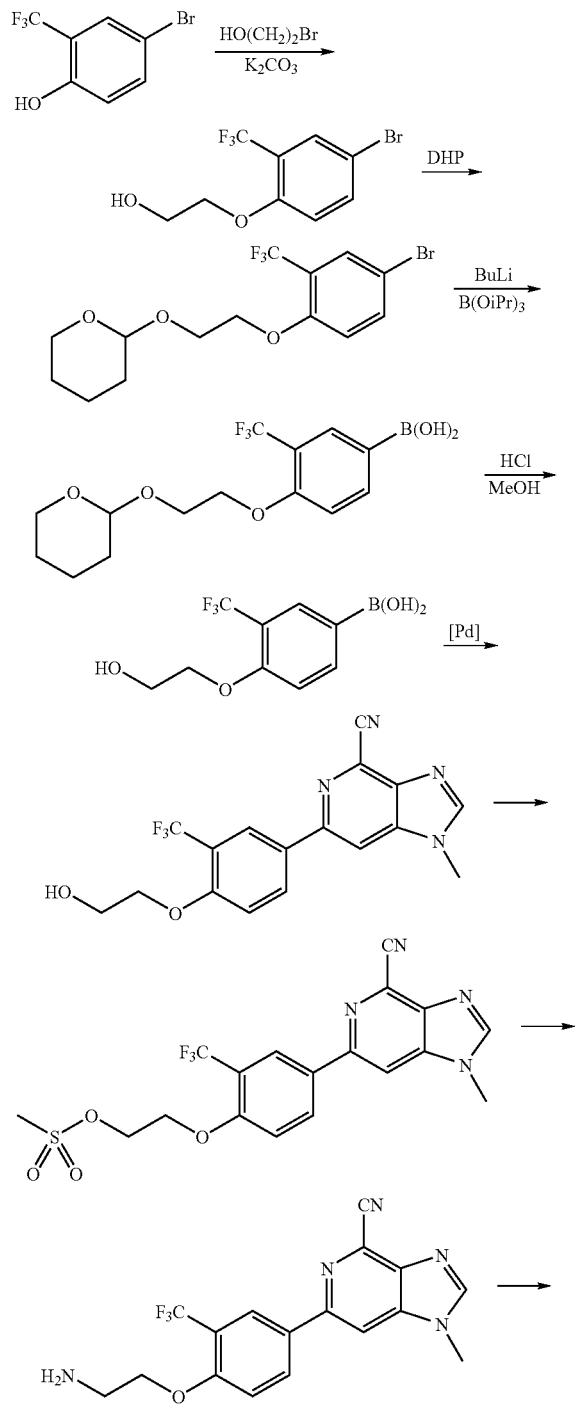

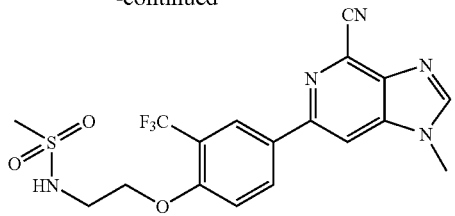

A: 2-(4-Bromo-2-(trifluoromethyl)phenoxy)-ethanol

2-Bromoethanol (23.3 g) was added to a mixture of 4-bromo-2-(trifluoromethyl)-phenol (30 g) and potassium carbonate (34.4 g) in acetonitrile (200 ml). The above mixture was refluxed for 8 hours then another portion of 2-bromoethanol (8 g) was added and the reflux continued for another 6 hours. After diluting with ethyl acetate (500 ml), the mixture was washed with water (300 ml) then 0.1 M sodium hydroxide (200 ml). Organic layer was dried over magnesium sulphate, solvent removed under reduced pressure, the residue was taken into heptane by heat, 2-(4-bromo-2-(trifluoromethyl)-phenoxy)-ethanol crystalised and collected by filtration (17 g).

$^1$H NMR (CDCl$_3$) δ: 7.69 (d, 1H), 7.59 (dd, 1H), 6.90 (d, 1H), 4.15 (t, 2H), 3.97 (t, 2H).

B: 2-(2-(4-Bromo-2-(trifluoromethyl)-phenoxy)-ethoxy)-tetrahydro-2H-pyran

A mixture of 2-(4-bromo-2-(trifluoromethyl)phenoxy) ethanol (16 g), 3,4-dihydro-2H-puran (9.5 g) and p-toluenesulfonic acid hydrate (0.5 g) in THF (100 ml) was stirred at room temperature for 1 hour then diluted with 5% sodium bicarbonate (300 ml) and extracted with ethyl acetate (500 ml). Organic layer was then dried over sodium sulphate, solvent removed under vacuum to give expected product (21 g).

$^1$H NMR (CDCl3) δ: 7.67 (d, 1H), 7.58 (dd, 1H), 6.93 (d, 1H), 4.71 (m, 1H), 4.23 (t, 2H), 4.08 (m, 1H), 3.75-3.95 (m, 2H), 3.53 (m, 1H), 1.5-1.9 (m, 6H).

C: 4-(2-(tetrahydro-2H-pyran-2-yloxy)-ethoxy)-3-(trifluoromethyl)-phenylboronic acid BuLi (2.5M, 6 ml) was added dropwise to a solution of 2-(2-(4-bromo-2-(trifluoromethyl)phenoxy)ethoxy)tetrahydro-2H-pyran (5 g) in THF (50 ml) at −78° C. under N2 during 3 minutes. After stirring at −78° C. for another 10 minutes, triisopropyl borate (3.8 ml) was then added dropwise during 2 minutes at −78° C. The mixture was stirred at −78° C. for further 30 minutes, then slowly warmed up to room temperature and stirred at room temperature for 30 minutes. The mixture was then quenched with acetic acid (10% in water, 20 ml), extracted with EtOAc (300 ml), washed with water (200 ml×3), dried over sodium sulphate, solvent removed under reduced pressure, the residue was taken in to toluene and then solvent removed under reduced pressure to take out traces of acetic acid (repeat 3 times) (4.5 g).

$^1$H NMR (CDCl3) δ: 8.38 (m, 1H), 8.33 (m, 1H), 7.16 (m, 1H), 4.74 (m, 1H), 4.22 (m, 2H), 4.08 (m, 1H), 3.92-3.80 (m, 2H), 3.56-3.50 (m, 1H), 1.90-1.68 (m, 2H), 1.65-1.48 (m, 4H).

D: 4-(2-Hydroxyethoxy)-3-(trifluoromethyl)-phenylboronic acid 4-(2-(Tetrahydro-2H-pyran-2-yloxy)ethoxy)-3-(trifluoromethyl)phenylboronic acid (8 g) was added to hydrochloric acid (1M in MeOH) and the mixture was heated at 60° C. for 60 minutes. Solvent and HCl was then removed under reduced pressure and residue (5.52 g) was used for next step without further purification.

$^1$H NMR (CDCl3 (0.7 ml)+CD3OD (0.2 ml)) δ: 7.97 (s, 1H), 7.88 (d, 1H), 7.0 (d, 1H), 4.19 (t, 2H), 3.98 (t, 2H).

E: 6-[4-(2-Hydroxyethoxy)-3-(trifluoromethyl)-phenyl]-1-methyl-1H-imidazo[4,5-c]pyridine-4-carbonitrile A mixture of 6-chloro-1-methyl-1H-imidazo[4,5-c]pyridine-4-carbonitrile (0.75 g), 4-(2-hydroxyethoxy)-3-(trifluoromethyl)phenylboronic acid (1.46 g), tris(dibenzylideneacetone)dipalladium (0.18 g), tricyclohexylphosphine (0.13 g) and tribasic potassium phosphate (1.65 g) in dioxane (7.5 ml) and water (3 ml) was heated at 100° C. under N2 for 3 hours. The mixture was then diluted with ethyl acetate (100 ml), organic layer seperated and solvent removed under reduced pressure, the residue was then columned on silica gel using DCM-MeOH (3%) as eluant to give 6-[4-(2-hydroxyethoxy)-3-(trifluoromethyl)-phenyl]-1-methyl-1H-imidazo[4,5-c]pyridine-4-carbonitrile (1.07 g).

$^1$H NMR (DMSO) δ: 8.65 (s, 1H), 8.60 (s, 1H), 8.40 (d, 1H), 8.39 (s, 1H), 7.43 (d, 1H), 4.9 (t, 1H), 4.25 (t, 1H), 3.97 (s, 3H), 3.30 (m, 1H). MS m/z 363 (M+H).

F: 2-(4-(4-Cyano-1-methyl-1H-imidazo[4,5-c]pyridin-6-yl)-2-(trifluoromethylphenoxy)ethyl methanesulfonate Methanesulphonyl chloride (0.23 ml) was added dropwise to a solution of 6-(4-(2-hydroxyethoxy)-3-(trifluoromethyl)-phenyl)-1-methyl-1H-imidazo[4,5-c]pyridine-4-carbonitrile (0.77 g) and diisopropylethylamine (1.2 ml) in NMP (6 ml). The mixture was stirred at room temperature for 3 hours. After adding cold water (20 ml), solid product was collected by filtration, washed with cold ethanol (20 ml) to give 2-(4-(4-cyano-1-methyl-1H-imidazo[4,5-c]pyridin-6-yl)-2-(trifluoromethyl)phenoxy)ethyl methanesulfonate (0.89 g).

$^1$H NMR (DMSO) δ: 8.72 (s, 1H), 8.64 (s, 1H), 8.47 (d, 1H), 8.43 (s, 1H), 7.48 (d, 1H), 4.58 (t, 2H), 4.51 (t, 2H), 3.99 (s, 3H), 3.23 (s, 3H). MS m/z 441 (M+1).

G: 6-{-4-[2-aminoethoxy]-3-(trifluoromethyl)-phenyl}-1-methyl-1H-imidazo[4,5-c]pyridine-4-carbonitrile MsOH A mixture of 2-(4-(4-cyano-1-methyl-1H-imidazo[4,5-c]pyridin-6-yl)-2-(trifluoromethyl)phenoxy)ethyl methanesulfonate (700 mg), and ammonia in methanol (7M, 8 ml) was heated in a microwave at 110° C. for 50 minutes. After removal of solvent under vacuum, the crude product, 6-{4-[2-amino-ethoxy]-3-(trifluoromethyl)-phenyl}-1-methyl-1H-imidazo[4,5-c]pyridine-4-carbonitrile methanesulphonic acid salt is sufficiently pure and used for next step without further purification.

$^1$H NMR (CD3OD) δ: 8.45 (s, 1H), 8.4-8.44 (m, 3H), 7.40 (d, 1H), 4.47 (t, 2H), 4.02 (s, 3H), 3.48 (t, 2H), 2.70 (s, MsOH).

H: N-(3-(4-(4-cyano-1-methyl-1H-imidazo[4,5-c]pyridin-6-yl)-2-(trifluoromethyl)phenoxy)ethyl)methanesulfonamide Methanesulphonyl chloride (31 mg) was added to the solution of 6-[4-(3-aminoethoxy)-3-(trifluoromethyl)-phenyl]-1-methyl-1H-imidazo[4,5-c]pyridine-4-carbonitrile (20 mg) in DCM (1 ml) containing DIPEA (44 uL). The mixture was stirred at rt for 1 hour, then solvent removed under vacuum and residue dissolved in NMP (1 ml) and purified by HPLC to give expected product, N-(3-(4-(4-cyano-1-methyl-1H-imidazo[4,5-c]pyridin-6-yl)-2-(trifluoromethyl)phenoxy)ethyl) methanesulfonamide. $^1$H NMR (DMSO) δ: 8.73 (s, 1H), 8.65 (s, 1H), 8.46 (d, 1H), 8.42 (s, 1H), 7.47 (d, 1H), 7.31 (t, 1H, NH), 4.27 (t, 2H), 3.99 (s, 3H), 3.40 (q, 2H), 2.96 (s, 3H). MS m/z 440 (M+H).

The procedure described in Example 6a was further applied, using the appropriate acylation agent, to prepare the following compound:

6b: 6-[4-(2-acetylaminoethoxy)-3-(trifluoromethyl)-phenyl]-1-methyl-1H-imidazo[4,5-c]pyridine-4-carbonitrile

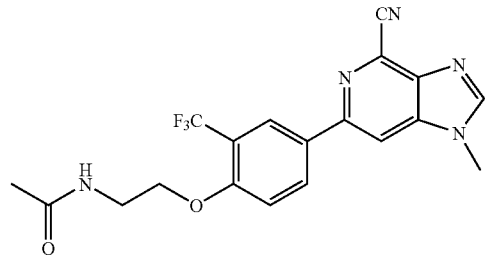

$^1$H NMR (CDCl3) δ: 8.28 (s, 1H), 8.26 (d, 1H), 8.19 (s, 1H), 7.90 (s, 1H), 7.12 (d, 1H), 6.17 (t, b, 1H, NH), 4.23 (t, 2H), 4.02 (s, 3H), 3.77 (q, 2H), 2.08 (s, 3H). MS m/z 404 (M+H).

EXAMPLE 7a 1-methyl-6-(4-(2-(N-propionyl-N-methylamino)ethoxy)-3-(trifluoromethyl)phenyl)-1H-imidazo[4,5-c]pyridine-4-carbonitrile

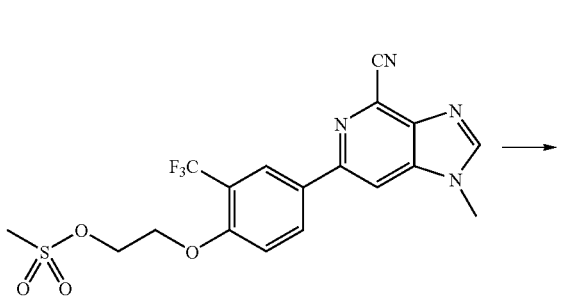

-continued

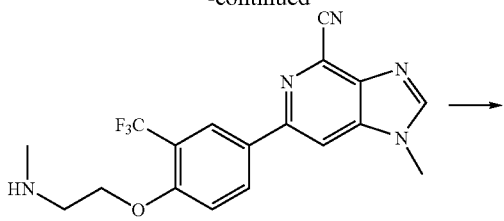

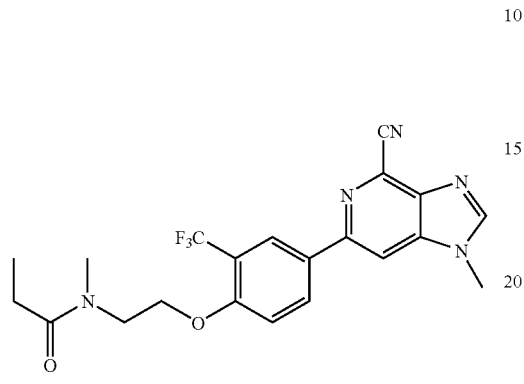

A: 1-methyl-6-(4-(2-(methylamino)ethoxy)-3-(trifluoromethyl)phenyl)-1H-imidazo[4,5-c]pyridine-4-carbonitrile A mixture of 2-(4-(4-cyano-1-methyl-1H-imidazo[4,5-c]pyridin-6-yl)-2-(trifluoromethyl)phenoxy)ethyl methanesulfonate (0.341 mmol, 150 mg) and methylamine (2M in THF, 1.703 mmol, 0.851 mL) in NMP (1 mL) was heated at 100° C. under microwave conditions for 20 minutes. The product was then purified by HPLC to give 1-methyl-6-(4-(2-(methylamino)ethoxy)-3-(trifluoromethyl)phenyl)-1H-imidazo[4,5-c]pyridine-4-carbonitrile as a TFA salt. The above TFA salt was then dissolved in MeOH (3 mL) and passed through a strong cation exchange (SCX) column. After washing with methanol to remove TFA residue, product was washed out with 2M ammonia in methanol. After removal of solvent, the free base of 1-methyl-6-(4-(2-(methylamino)ethoxy)-3-(trifluoromethyl)phenyl)-1H-imidazo[4,5-c]pyridine-4-carbonitrile was obtained as a white solid. $^1$H NMR (CD$_3$OD) δ: 8.43 (s, 1H), 8.35-8.39 (m, 3H), 7.36 (d, 1H), 4.30 (t, 2H), 4.02 (s, 3H), 3.03 (t, 2H), 2.50 (s, 3H). MS m/z 376 (M+H).

B: 1-methyl-6-(4-(2-(N-propionyl-N-methylamino)ethoxy)-3-(trifluoromethyl)phenyl)-1H-imidazo[4,5-c]pyridine-4-carbonitrile To a solution of 1-methyl-6-(4-(2-(methylamino)ethoxy)-3-(trifluoromethyl)-phenyl)-1H-imidazo[4,5-c]pyridine-4-carbonitrile (0.053 mmol, 20 mg) in THF (1 mL) was added DIPEA (0.266 mmol, 47 μL) and propionyl chloride (0.16 mmol, 15 mg). The mixture was stirred at r.t. for 16 h and the product was then purified by HPLC to give 1-methyl-6-(4-(2-(N-propionyl-N-methylamino)ethoxy)-3-(trifluoromethyl)phenyl)-1H-imidazo[4,5-c]pyridine-4-carbonitrile. $^1$H NMR (CD$_3$OD) δ: 8.37-8.46 (m, 4H), 7.31 (d, 1H), 4.31-4.37 (m, 2H), 3.90 (s, 3H), 3.82-3.90 (m, 2H), 3.01, 3.30 (2xs, 3H), 2.42-2.58 (m, 2H), 1.10-1.15 (m, 3H). MS m/z 432 (M+H).

The procedure described in Example 7a was further applied, using the appropriate acyl chloride derivatives, to prepare the following compounds:

7b: 1-methyl-6-(4-(2-(N-isobutyryl-N-methylamino)ethoxy)-3-(trifluoromethyl)phenyl)-1H-imidazo[4,5-c]pyridine-4-carbonitrile

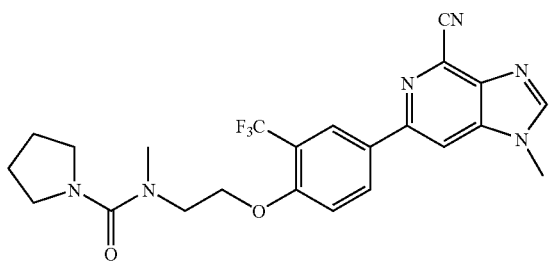

$^1$H NMR (CD$_3$OD) δ: 8.34-8.46 (m, 4H), 7.31 (d, 1H), 4.31-4.36 (m, 2H), 4.02 (s, 3H), 3.81-3.92 (m, 2H), 3.03, 3.30 (2xs, 3H), 2.97 (m, 1H), 1.10-1.14 (m, 6H). MS m/z 446 (M+H).

7c: N-(2-(4-(4-cyano-1-methyl-1H-imidazo[4,5-c]pyridin-6-yl)-2-(trifluoromethyl)phenoxy)ethyl)-N-methylpyrrolidine-1-carboxamide

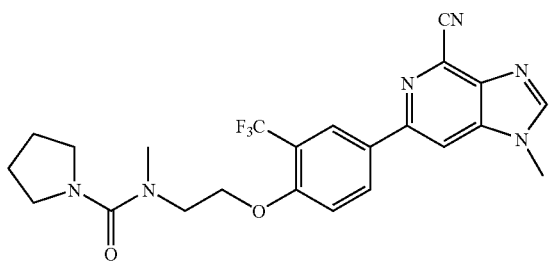

$^1$H NMR (CD$_3$OD) δ: 8.40-8.44 (m, 4H), 7.31 (d, 1H), 4.34 (t, 2H), 4.03 (s, 3H), 3.71 (t, 2H), 3.36-3.39 (m, 4H), 3.04 (s, 3H), 1.83-1.86 (m, 4H). MS m/z 473 (M+H).

7d: 1-methyl-6-(4-(2-(N-acetyl-N-methylamino)ethoxy)-3-(trifluoromethyl)phenyl)-1H-imidazo[4,5-c]pyridine-4-carbonitrile

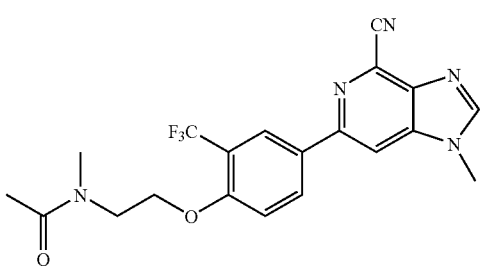

$^1$H NMR (DMSO) δ: 8.71 (s, 1H), 8.63 (s, 1H), 8.43 (d, 1H), 8.42 (s, 1H), 7.45 (m, 1H), 4.37 (m, 1H), 4.30 (m, 1H), 3.99 (s, 3H), 3.77 (m, 1H), 3.70 (m, 1H), 3.09 2.88 (2 s, 3H), 2.08 2.01 (2 s, 3H). MS m/z 418 (M+H).

7e: N-(2-(4-(4-cyano-1-methyl-1H-imidazo[4,5-c]pyridine-6-yl)-2-(trifluoromethyl)phenoxy)ethyl)-N-methylmethanesulfonamide

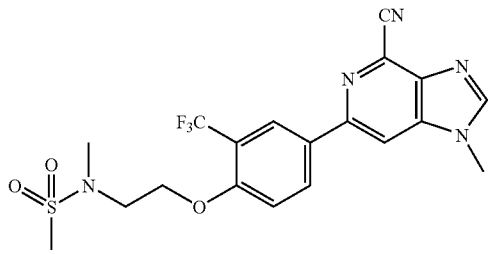

$^1$H NMR (MeOD) δ: 8.73 (s, 1H), 8.64 (s, 1H), 7.35 (d, 1H), 4.38 (t, 2H), 4.00 (s, 3H), 3.55 (t, 2H), 2.96 (s, 3H), 2.93 (s, 3H). MS m/z 454.2 (M+H).

EXAMPLE 8a 6-(4-(2-(N-Acetyl-N-isopropylamino)ethoxy)-3-(trifluoromethyl)phenyl)-1-methyl-1H-imidazo[4,5-c]pyridine-4-carbonitrile

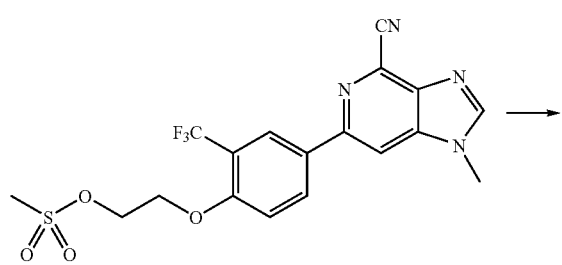

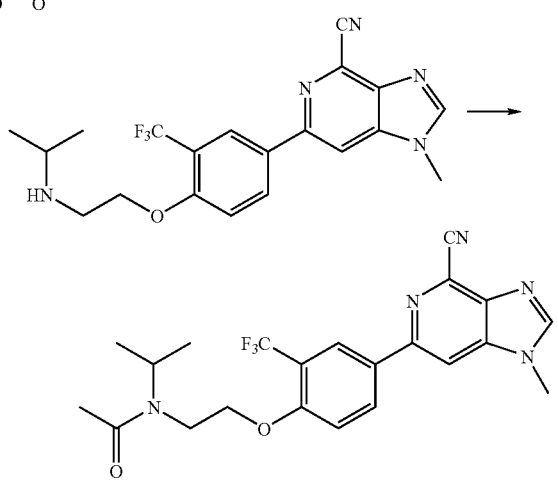

A: 6-(4-(2-(isopropylamino)ethoxy)-3-(trifluoromethyl)phenyl)-1-methyl-1H-imidazo[4,5-c]pyridine-4-carbonitrile A mixture of 2-(4-(4-cyano-1-methyl-1H-imidazo[4,5-c]pyridin-6-yl)-2-(trifluoromethyl)phenoxy)ethyl methanesulfonate (0.341 mmol, 150 mg) and isopropylamine (1.703 mmol, 101 mg) in NMP (1 mL) was heated at 100° C. under microwave conditions for 20 minutes. The product was then purified by HPLC to give 6-(4-(2-(isopropylamino)ethoxy)-3-(trifluoromethyl)phenyl)-1-methyl-1H-imidazo[4,5-c]pyridine-4-carbonitrile as a TFA salt. The above TFA salt was then dissolved in MeOH (3 mL) and passed through a strong cation exchange (SCX) column. After washing with methanol to remove TFA residue, product was washed out with 2M ammonia in methanol. After removal of solvent, the free base of 6-(4-(2-(isopropyl-amino)ethoxy)-3-(trifluoromethyl)phenyl)-1-methyl-1H-imidazo[4,5-c]pyridine-4-carbonitrile was obtained as a white solid. $^1$H NMR (CD$_3$OD) δ: 8.40-8.44 (m, 4H), 7.36 (d, 1H), 4.31 (t, 2H), 4.03 (s, 3H), 3.07 (t, 2H), 2.95 (m, 1H), 1.13 (d, 6H). MS m/z 404 (M+H).

B: 6-(4-(2-(N-Acetyl-N-isopropylamino)ethoxy)-3-(trifluoromethyl)phenyl)-1-methyl-1H-imidazo[4,5-c]pyridine-4-carbonitrile To a solution of 6-(4-(2-(isopropylamino)ethoxy)-3-(trifluoromethyl)phenyl)-1-methyl-1H-imidazo[4,5-c]pyridine-4-carbonitrile (0.05 mmol, 20 mg) in THF (1 mL) was added DIPEA (0.248 mmol, 44 µL) and acetyl chloride (0.149 mmol, 12 mg). The mixture was stirred at r.t. for 16 h and the product was then purified by HPLC to give 6-(4-(2-(N-acetyl-N-isopropylamino)ethoxy)-3-(trifluoromethyl)phenyl)-1-methyl-1H-imidazo[4,5-c]pyridine-4-carbonitrile. $^1$H NMR (CD$_3$OD) δ: 8.38-8.44 (m, 4H), 7.35 (d, 1H), 4.15-4.34 (m, 3H), 4.02 (s, 3H), 3.68-3.85 (m, 2H), 2.19 (2xs, 3H), 1.25-1.29 (m, 6H). MS m/z 446 (M+H).

EXAMPLE 9a 6-(4-(2-(N-Acetyl-N-ethylamino)ethoxy)-3-(trifluoromethyl)phenyl)-1-methyl-1H-imidazo[4,5-c]pyridine-4-carbonitrile

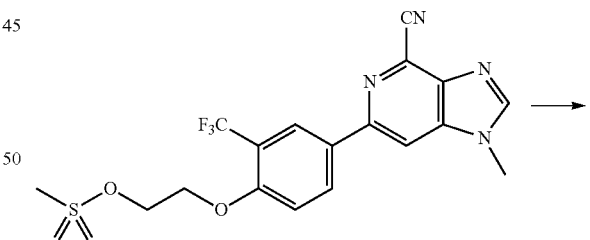

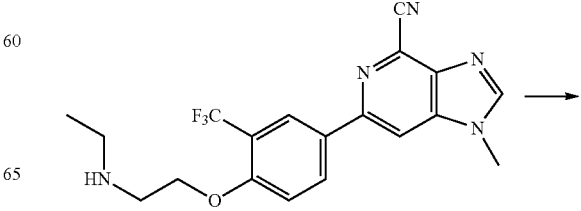

-continued

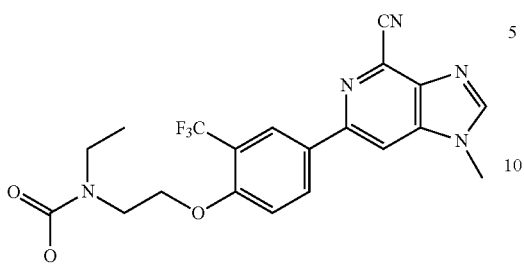

A: 6-(4-(3-(ethylamino)ethoxy)-3-(trifluoromethyl)phenyl)-1-methyl-1H-imidazo[4,5-c]pyridine-4-carbonitrile Ethylamine (2M in THF, 0.851 ml) was added to 2-(4-(4-cyano-1-methyl-1H-imidazo[4,5-c]pyridin-6-yl)-2-(trifluoromethyl)phenoxy)ethyl methanesulfonate (150 mg) dissolved in NMP (1 ml). The reaction mixture was heated at 100° C. under microwave conditions for 20 minutes. The reaction mixture was filtered and then purified by acidic prep HPLC to give 6-(4-(3-(ethylamino)ethoxy)-3-(trifluoromethyl)-phenyl)-1-methyl-1H-imidazo[4,5-c]pyridine-4-carbonitrile as a TFA salt. The above TFA salt was then dissolved in MeOH (3 ml) and passed through a strong cation exchange (SCX) column. After washing with methanol to remove TFA residue, product was washed out with 2M ammonia in methanol. After removal of solvent, the free base of 6-(4-(3-(ethylamino)ethoxy)-3-(trifluoromethyl)phenyl)-1-methyl-1H-imidazo[4,5-c]pyridine-4-carbonitrile (60 mg). $^1$H NMR (MeOD) δ: 8.44-8.40 (m, 4H), 7.35 (d, 1H), 4.31 (t, 2H), 4.03 (s, 3H), 3.09 (t, 2H), 2.77 (q, 2H), 1.19 (t, 3H). MS m/z 390 (M+H).

B: 6-(4-(2-(N-Acetyl-N-ethylamino)ethoxy)-3-(trifluoromethyl)phenyl)-1-methyl-1H-imidazo[4,5-c]pyridine-4-carbonitrile Acetyl chloride (0.011 ml) was added dropwise to a solution of 6-(4-(3-(ethylamino)ethoxy)-3-(trifluoromethyl)phenyl)-1-methyl-1H-imidazo[4,5-c]pyridine-4-carbonitrile (20 mg) and diisopropylethylamine (0.045 ml) in THF (2 ml). The reaction mixture was stirred at room temperature for 1 hour. The product was then purified by acidic prep HPLC to give 6-(4-(2-(N-Acetyl-N-ethylamino)ethoxy)-3-(trifluoromethyl)-phenyl)-1-methyl-1H-imidazo[4,5-c]pyridine-4-carbonitrile. $^1$H NMR (DMSO) δ: 8.7 (s, 1H), 8.60 (s, 1H), 8.42-8.35 (m, 2H), 7.41 (d, 1H), 4.31-4.20 (tt, 2H), 3.42 (s, 3H), 3.70-3.60 (tt, 2H), 3.40 (m, 2H), 2.02+2.00 (2xs, 3H), 1.1+0.97 (2xt, 3H). MS m/z 432 (M+H).

The procedure described in Example 9a was further applied, using the appropriate acid chloride to prepare the following compounds:

9b: 6-(4-(2-(N-ethyl-N-propionylamino)ethoxy)-3-(trifluoromethyl)phenyl)-1-methyl-1H-imidazo[4,5-c]pyridine-4-carbonitrile

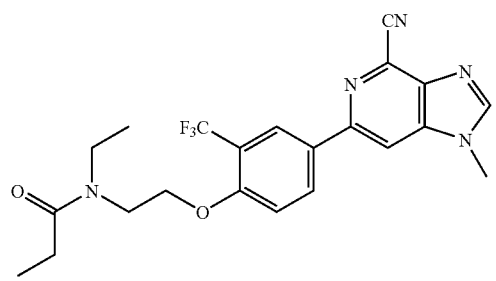

$^1$H NMR (DMSO) δ: 8.7 (s, 1H), 8.60 (s, 1H), 8.42-8.35 (m, 2H), 7.41 (d, 1H), 4.31-4.20 (tt, 2H), 3.92 (s, 3H), 3.70-3.60 (tt, 2H), 3.40 (m, 2H), 2.40-2.25 (2xt, 2H), 1.10-0.90 (m, 6H). MS m/z 446 (M+H).

9c: 6-(4-(2-(N-ethyl-N-isobutyrylamino)ethoxy)-3-(trifluoromethyl)phenyl)-1-methyl-1H-imidazo[4,5-c]pyridine-4-carbonitrile

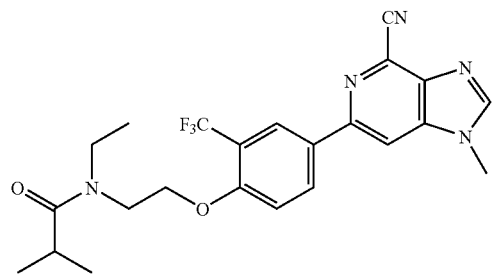

$^1$H NMR (DMSO) δ: 8.72 (s, 1H), 8.64 (s, 1H), 8.50-8.35 (m, 2H), 7.50 (m, 1H), 4.35-4.28 (m, 2H), 3.99 (s, 3H), 3.65

(m, 2H), 3.50+3.36 (2xm, 2H), 2.83 (m, 1H), 1.15 (t, 3H), 1.00 (d, 6H). MS m/z 460 (M+H).

EXAMPLE 10a 6-(4-(2-(N-Acetyl-N-cyclopropylamino)ethoxy)-3-(trifluoromethyl)phenyl)-1-methyl-1H-imidazo[4,5-c]pyridine-4-carbonitrile

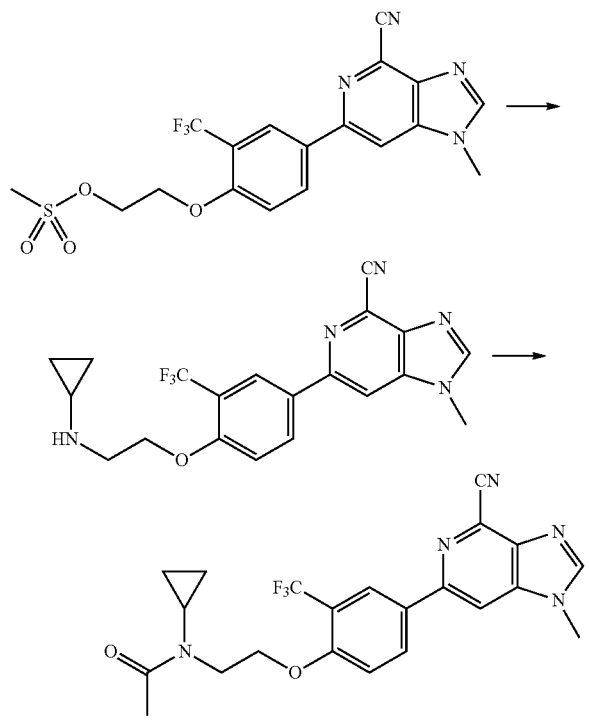

A: 6-(4-(3-(cyclopropylamino)ethoxy)-3-(trifluoromethyl)phenyl)-1-methyl-1H-imidazo[4,5-c]pyridine-4-carbonitrile Cyclopropanamine (0.118 ml) was added 6-(4-(2-(cyclopropylamino)ethoxy)-3-(trifluoromethyl)phenyl)-1-methyl-1H-imidazo[4,5-c]pyridine-4-carbonitrile (150 mg) dissolved in NMP (1 ml). The reaction mixture was heated at 100° C. under microwave conditions for 20 minutes. The reaction mixture was filtered and then purified by acidic prep HPLC to give 6-(4-(3-(cyclopropylamino)ethoxy)-3-(trifluoromethyl)phenyl)-1-methyl-1H-imidazo[4,5-c]pyridine-4-carbonitrile as a TFA salt. The above TFA salt was then dissolved in MeOH (3 ml) and passed through a strong cation exchange (SCX) column. After washing with methanol to remove TFA residue, product was washed out with 2M ammonia in methanol. After removal of solvent, the free base of 6-(4-(3-(cyclopropylamino)ethoxy)-3-(trifluoromethyl)phenyl)-1-methyl-1H-imidazo[4,5-c]pyridine-4-carbonitrile (60 mg)

$^1$H NMR (MeOD) δ: 8.44-8.40 (m, 4H), 7.35 (d, 1H), 4.30 (t, 2H), 4.03 (s, 3H), 3.15 (t, 2H), 2.30 (q, 1H), 0.53 (m, 3H), 0.40 (m, 3H). MS m/z 402 (M+H).

B: 6-(4-(2-(N-Acetyl-N-cyclopropylamino)ethoxy)-3-(trifluoromethyl)phenyl)-1-methyl-1H-imidazo[4,5-c]pyridine-4-carbonitrile Acetyl chloride (0.011 ml) was added dropwise to a solution of 6-(4-(3-(cyclopropylamino)ethoxy)-3-(trifluoromethyl)phenyl)-1-methyl-1H-imidazo[4,5-c]pyridine-4-carbonitrile (20 mg) and diisopropylethylamine (0.044 ml) in THF (2 ml). The reaction mixture was stirred at room temperature for 1 hour. The product was then purified by acidic prep HPLC to give 6-(4-(2-(N-acetyl-N-cyclopropylamino)-ethoxy)-3-(trifluoromethyl)phenyl)-1-methyl-1H-imidazo[4,5-c]pyridine-4-carbonitrile.

$^1$H NMR (MeOD) δ: 8.45-8.36 (m, 4H), 7.35 (d, 1H), 4.37 (t, 2H), 4.03 (s, 3H), 3.85 (t, 2H), 2.90 (m, 1H), 2.25 (s, 3H), 1.30 (m, 1H), 1.00-0.82 (m, 5H). MS m/z 444 (M+H).

The procedure described in Example 10a was further applied, using the appropriate acid chloride to prepare the following compound:

10b: 6-(4-(2-(N-cyclopropyl-N-propionylamino)ethoxy)-3-(trifluoromethyl)phenyl)-1-methyl-1H-imidazo[4,5-c]pyridine-4-carbonitrile

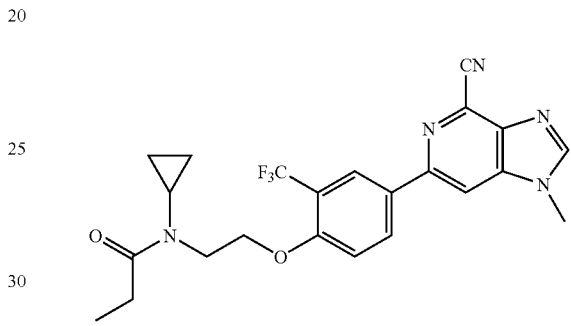

$^1$H NMR (MeOD) δ: 8.45-8.36 (m, 4H), 7.35 (d, 1H), 4.37 (t, 2H), 4.03 (s, 3H), 3.85 (t, 2H), 2.86 (m, 1H), 2.65 (q, 2H), 1.12 (t, 3H), 0.98-0.80 (m, 4H). MS m/z 458 (M+H).

EXAMPLE 11a

1-Methyl-6-{4-[(2-(pyrolidin-1-yl)-pyridin-4-yl)-methoxy]-3-(trifluoromethyl)-phenyl}-1H-imidazol-[4,5-c]pyridine-4-carbonitrile

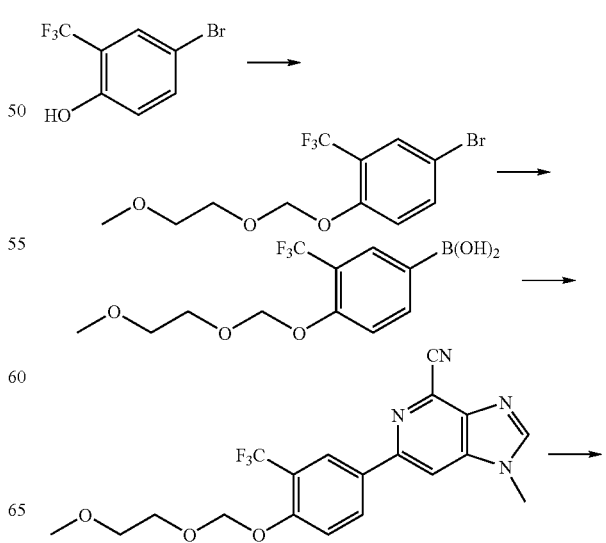

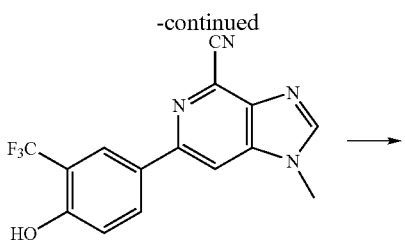

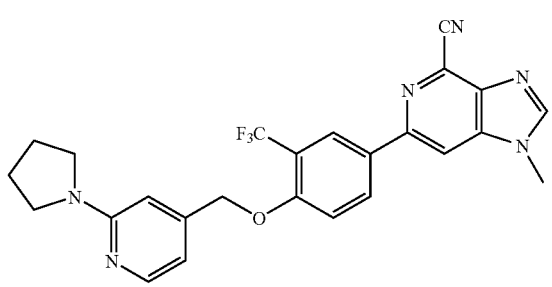

A: 4-Bromo-1-(2-methoxy-ethoxymethoxy)-2-trifluoromethyl-benzene

Sodium hydride (60% w/w dispersion in mineral oil, 0.96 g) was added to a solution of 4-bromo-2-trifluoromethyl-phenol (5.0 g) in dry THF (200 ml) and the mixture was stirred for 30 minutes. 1-Chloromethoxy-2-methoxy-ethane (2.85 ml) was then added and the mixture was stirred for 1 hour at room temperature. The solvent was removed under reduced pressure. The residue was taken into water and tert-butyl methyl ether, the organic layer was washed with brine, dried over sodium sulphate and concentrated under reduced pressure to afford 4-bromo-1-(2-methoxy-ethoxymethoxy)-2-trifluoromethyl-benzene (6.4 g) as an oil. $^1$H NMR (CDCl$_3$) δ: 7.69 (m, 1H), 7.53 (m, 1H), 7.19 (m, 1H), 5.33 (s, 2H), 3.83 (m, 2H), 3.55 (m, 2H), 3.37 (s, 3H).

B: 4-(2-Methoxy-ethoxymethoxy)-3-trifluoromethyl-phenyl-boronic acid n-Butyl lithium (2.5M in hexane, 91.2 ml) was added dropwise to a solution of 4-bromo-1-(2-methoxy-ethoxymethoxy)-2-trifluoromethyl-benzene (30 g) in dry THF (335 ml) at −78° C. under nitrogen atmosphere. The mixture was then stirred at −78° C. for another 30 minutes. Triisopropyl borate (101 ml) was then added slowly at −78° C. under nitrogen, the mixture was then allowed to slowly warm up to room temperature and stirred at this temperature overnight. After adding water (300 ml), the mixture was extracted with ethyl acetate (300 ml×3). The combined organic layers were dried over sodium sulphate. After removal of solvent under reduced pressure, the residue was columned on silica gel using DCM-MeOH as eluant to give 4-(2-methoxy-ethoxymethoxy)-3-trifluoromethyl-phenyl-boronic acid (14.4 g).

$^1$H NMR (CDCl3) δ: 8.38 (m, 1H), 8.33 (m, 1H), 7.42 (m, 1H), 5.46 (s, 2H), 3.86 (m, 2H), 3.56 (m, 2H), 3.38 (s, 3H).

C: 6-(4-(2-Methoxy-ethoxymethoxy)-3-trifluoromethyl-phenyl)-1-methyl-1H-imidazo[4,5-c]pyridine-4-carbonitrile A mixture of 6-chloro-1-methyl-1H-imidazo[4,5-c]pyridine-4-carbonitrile (5.9 g), 4-(2-methoxy-ethoxymethoxy)-3-trifluoromethyl-phenyl-boronic acid (9.92 g), potassium phosphate (11.1 g), tris(dibenzylideneacetone)dipalladium (1.4 g) and tricyclohexylphosphine (1.03 g) in dioxane (190 ml) and water (60 ml) was heated at 100° C. under nitrogen atmosphere for 2 hours. After cooling to room temperature, the mixture was then extracted with ethyl acetate (500 ml×2), the combined organic layers were dried over sodium sulphate and solvent was then removed under reduced pressure. To the residue was then added methanol (20 ml), and the solid product, 6-(4-(2-methoxy-ethoxymethoxy)-3-trifluoromethyl-phenyl)-1-methyl-1H-imidazo[4,5-c]pyridine-4-carbonitrile was collected by filtration (8.95 g). $^1$H NMR (CDCl$_3$) δ: 8.27 (m, 1H), 8.19 (m, 1H), 8.10 (s, 1H), 7.88 (s, 1H), 7.42 (m, 1H), 5.44 (s, 2H), 3.99 (s, 3H), 3.88 (m, 2H), 3.58 (m, 2H), 3.38 (s, 3H). MS m/z 407 (M+1).

D: 6-(4-Hydroxy-3-trifluoromethyl-phenyl)-1-methyl-1H-imidazo[4,5-c]pyridine-4-carbonitrile 6-(4-(2-Methoxy-ethoxymethoxy)-3-trifluoromethyl-phenyl)-1-methyl-1H-imidazo[4,5-c]pyridine-4-carbonitrile (7.5 g) was added to a mixed solvent of THF (300 ml) and 1M HCl (aq). The mixture was heated to 65° C. until the full disappearance of all starting material. After adding saturated sodium chloride solution (200 ml), the mixture was extracted with ethyl acetate (300 ml×3), and the combined organic layers were then dried over sodium sulphate, solvent was removed under reduced pressure, and the residue was triturated in ether. Product, 6-(4-hydroxy-3-trifluoromethyl-phenyl)-1-methyl-1H-imidazo[4,5-c]pyridine-4-carbonitrile (5.9 g) was collected by filtration. $^1$H NMR (CD3OD) δ: 8.45 (s, 1H); 8.34 (s, 1H); 8.29 (s, 1H); 8.20 (m, 1H); 7.09 (m, 1H); 4.04 (s, 3H). MS m/z 319 (M+1).

E: 1-Methyl-6-{4-[(2-(pyrrolidin-1-yl)-pyridin-4-A-methoxy]-3-(trifluoromethyl)-phenyl}-1H-imidazo[4,5-c]pyridine-4-carbonitrile Diisopropyl azodicarboxylate (80 mg) was added with stirring at room temperature under a nitrogen atmosphere to a mixture of 6-(4-hydroxy-3-trifluoromethyl-phenyl)-1-methyl-1H-imidazo[4,5-c]pyridine-4-carbonitrile (42 mg), resin bound triphenylphosphine (3 mmol/g, 130 mg) and 2-(pyrrolidin-1-yl)-pyridin-4-ylmethanol (54 mg) in DCM (2 ml). The mixture was then shaken for 8 hours. After filtering off resin, the filtrate was concentrated under reduced pressure, and the residue was purified by HPLC to give 1-methyl-6-{4-[(2-(pyrrolidin-1-yl)-pyridin-4-yl)-methoxy]-3-(trifluoromethyl)-phenyl}-1H-imidazo[4,5-c]pyridine-4-carbonitrile as a TFA salt. This salt was then converted to free base using the SCX procedure described before. $^1$H NMR (DMSO) δ: 8.73 (s, 1H), 8.64 (s, 1H), 8.44 (m, 2H), 8.07 (d, 1H), 7.48 (d, 1H), 6.58 (d, 1H), 6.55 (s, 1H), 5.33 (s, 2H), 3.99 (s, 3H), 3.36 (m, 4H), 1.94 (m, 4H). MS m/z 479 (M+1).

The procedure described in Example 11a was further applied, using the appropriate alcohol, to prepare the following compounds as either salts or free base:

11b: 6-{4-[(6-(Dimethylamino)-pyridin-2-yl)-methoxy]-3-(trifluoromethyl)-phenyl}-1-methyl-1H-imidazol-[4,5-c]pyridine-4-carbonitrile

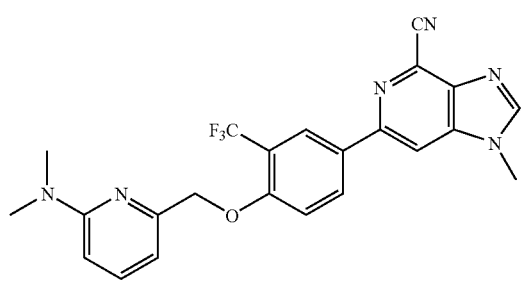

$^1$H NMR (DMSO) δ: 8.72 (s, 1H), 8.64 (s, 1H), 8.44 (m, 2H), 7.56 (m, 1H), 7.53 (m, 1H), 6.71 (d, 1H), 6.60 (s, 1H), 5.26 (s, 2H), 3.99 (s, 3H), 3.03 (s, 6H). MS m/z 453 (M+1).

11c: 6-{4-[(6-Fluoropyridin-2-yl)-methoxy]-3-(trifluoromethyl)-phenyl}-1-methyl-1H-imidazo[4,5-c]pyridine-4-carbonitrile

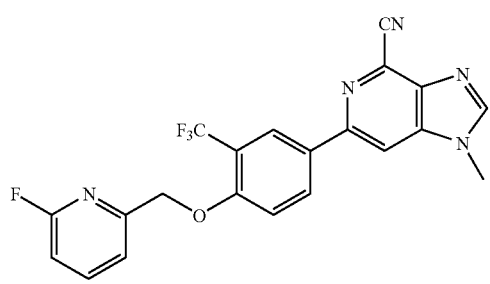

$^1$H NMR (DMSO) δ: 8.74 (s, 1H), 8.65 (s, 1H), 8.46 (m, 2H), 8.10 (q, 1H), 7.51 (d, 1H), 7.47 (d, 1H), 7.17 (d, 1H), 5.41 (s, 2H), 3.99 (s, 3H). MS m/z 428 (M+1).

11d: 6-{4-[(2-Fluoropyridin-4-yl)-methoxy]-3-(trifluoromethyl)-phenyl}-1-methyl-1H-imidazo[4,5-c]pyridine-4-carbonitrile

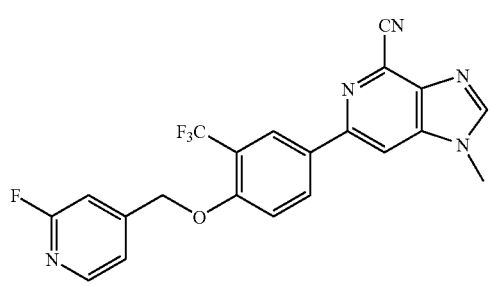

$^1$H NMR (DMSO) δ: 8.74 (s, 1H), 8.66 (s, 1H), 8.48 (m, 2H), 8.32 (q, 1H), 7.51 (d, 1H), 7.43 (d, 1H), 7.21 (s, 1H), 5.52 (s, 2H), 3.99 (s, 3H). MS m/z 428 (M+1).

11e: 1-Methyl-6-{4-[(4-methoxypyridin-2-yl)-methoxy]-3-(trifluoromethyl)-phenyl}-1H-imidazo[4,5-c]pyridine-4-carbonitrile

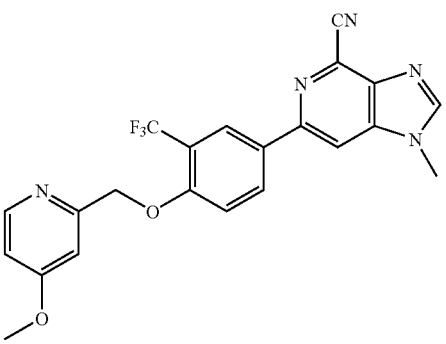

$^1$H NMR (DMSO) δ: 8.74 (s, 1H), 8.65 (s, 1H), 8.46 (s, 1H), 8.42 (d, 1H), 7.54 (d, 1H), 7.09 (s, 1H), 6.96 (d, 1H), 5.39 (s, 2H), 3.99 (s, 3H), 3.84 (s, 3H). MS m/z 440 (M+1).

EXAMPLE 12a

1-Methyl-6-{4-[(2-(N-ethyl-N-methylamino)-pyridin-4-yl)-methoxy]-3-(trifluoromethyl)-phenyl}-1H-imidazo[4,5-c]pyridine-4-carbonitrile Hydrocloride

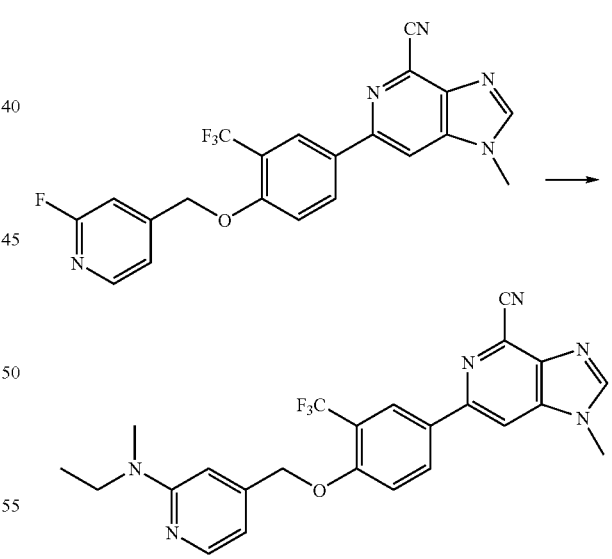

6-(4-((2-fluoropyridin-4-yl)methoxy)-3-(trifluoromethyl)phenyl)-1-methyl-1H-imidazo[4,5-c]pyridine-4-carbonitrile (200 mg) and N-ethylmethylamine (122 μl) were dissolved in NMP (2000 μl) and heated at 140° C. for 5 hours in a microwave. Purification by preparative HPLC afforded the product as a TFA salt. This TFA salt was then converted to free base by means of SCX method, then to HCl salt by treating with 2M HCl in ether. Product 1-methyl-6-{4-[(2-(N-ethyl-N-methylamino)-pyridin-4-yl)-methoxy]-3-(trifluoromethyl)-phenyl}-1H-imidazo[4,5-c]pyridine-4-carbonitrile was obtained as a pale yellow solid. ¹H NMR (CD3OD) δ: 8.44 (m, 2H), 8.40 (s, 1H), 8.36 (d, 1H), 7.90 (d, 1H), 7.34 (m, 2H), 6.96 (d, 1H), 5.36 (s, 2H), 4.02 (s, 3H), 3.68 (m, 2H), 3.32 (s, 3H), 1.32 (t, 3H). MS m/z 467.1 (M+H).

The procedure described in Example 12a was further applied, using the appropriate alcohol, to prepare the following compounds as either salts or free base:

12b: 1-Methyl-6-{4-[(2-(N-ethylamino)-pyridin-4-O-methoxy]-3-(trifluoromethyl)-phenyl}-1H-imidazo[4,5-c]pyridine-4-carbonitrile ¹H NMR (DMSO) δ: 8.72 (s, 1H), 8.65 (s, 1H), 8.45 (s, 1H), 8.43 (d, 1H), 7.98 (d, 1H), 7.45 (d, 1H), 6.62 (br, NH), 6.52 (m, 2H), 5.28 (s, 2H), 3.99 (s, 3H), 3.24 (m, 2H), 1.12 (t, 3H). MS m/z 453 (M+1).

12c: 1-Methyl-6-{4-[(2-(N-methylamino)-pyridin-4-yl)-methoxy]-3-(trifluoromethyl)-phenyl}-1H-imidazo[4,5-c]pyridine-4-carbonitrile ¹H NMR (DMSO) δ: 8.72 (s, 1H), 8.65 (s, 1H), 8.45 (s, 1H), 8.43 (d, 1H), 8.00 (d, 1H), 7.45 (d, 1H), 6.64 (br, NH), 6.55 (d, 1H), 6.52 (s, 1H), 5.29 (s, 2H), 3.99 (s, 3H), 2.75 (d, 3H). MS m/z 439 (M+1).

12d: 1-Methyl-6-{4-[(2-(dimethylamino)-pyridin-4-yl)-methoxy]-3-(trifluoromethyl)-phenyl}-1H-imidazo[4,5-c]pyridine-4-carbonitrile

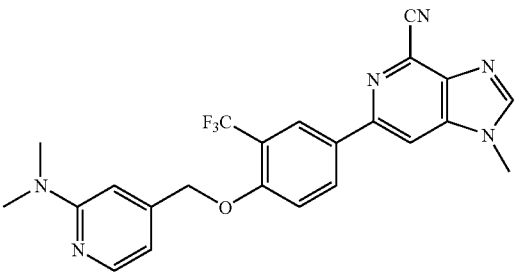

¹H NMR (DMSO) δ: 8.73 (s, 1H), 8.65 (s, 1H), 8.45 (m, 2H), 8.10 (d, 1H), 7.50 (d, 1H), 6.74 (s, 1H), 6.62 (d, 1H), 5.34 (s, 2H), 3.99 (s, 3H), 3.03 (s, 6H). MS m/z 453 (M+1).

12e: 1-Methyl-6-{4-[(6-(N-methylamino)-pyridin-2-yl)-methoxy]-3-(trifluoromethyl)-phenyl}-1H-imidazo[4,5-c]pyridine-4-carbonitrile

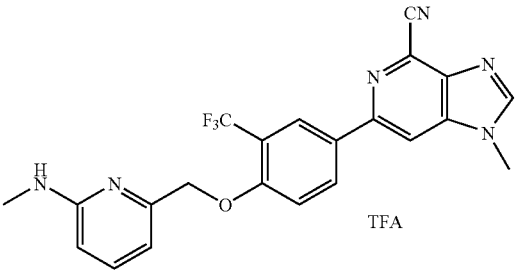

¹H NMR (CD3OD) δ: 8.4-8.5 (m, 4H), 7.90 (t, 1H), 7.43 (d, 1H), 7.03 (d, 1H), 7.00 (d, 1H), 5.38 (s, 2H), 4.03 (s, 3H), 3.08 (s, 3H). MS m/z 439 (M+1).

12f: 1-Methyl-6-{4-[(6-(N-ethylamino)-pyridin-2-yl)-methoxy]-3-(trifluoromethyl)-phenyl}-1H-imidazo[4,5-c]pyridine-4-carbonitrile

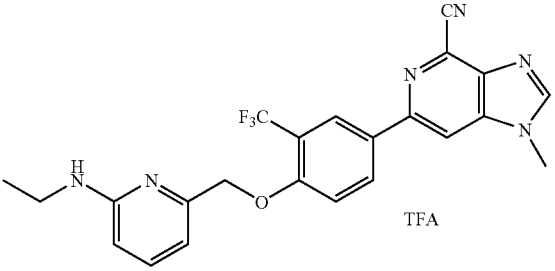

¹H NMR (CD3OD) δ: 8.4-8.5 (m, 4H), 7.90 (t, 1H), 7.43 (d, 1H), 7.02 (d, 1H), 7.00 (d, 1H), 5.37 (s, 2H), 4.03 (s, 3H), 3.48 (q, 2H), 1.36 (t, 3H). MS m/z 453 (M+1).

12g: 1-Methyl-6-{4-[(6-(N-isopropylamino)-pyridin-2-yl)-methoxy]-3-(trifluoromethyl)-phenyl}-1H-imidazo[4,5-c]pyridine-4-carbonitrile

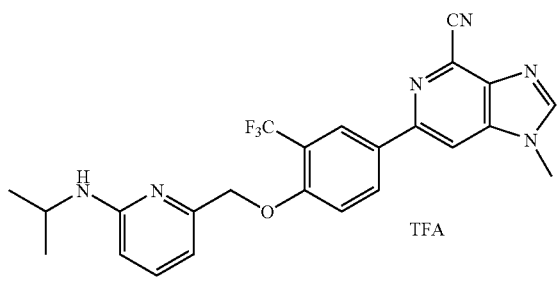

TFA

¹H NMR (CD3OD) δ: 8.4-8.5 (m, 4H), 7.83 (t, 1H), 7.44 (d, 1H), 6.98 (d, 1H), 6.94 (d, 1H), 5.35 (s, 2H), 4.05 (m, 1H), 4.03 (s, 3H), 1.33 (d, 6H). MS m/z 467 (M+1).

EXAMPLE 13a

1-Methyl-6-{4-[2-(1-acetylpiperidin-4-yl)-ethoxy]-3-(trifluoromethyl)-phenyl}-1H-imidazo[4,5-c]pyridine-4-carbonitrile

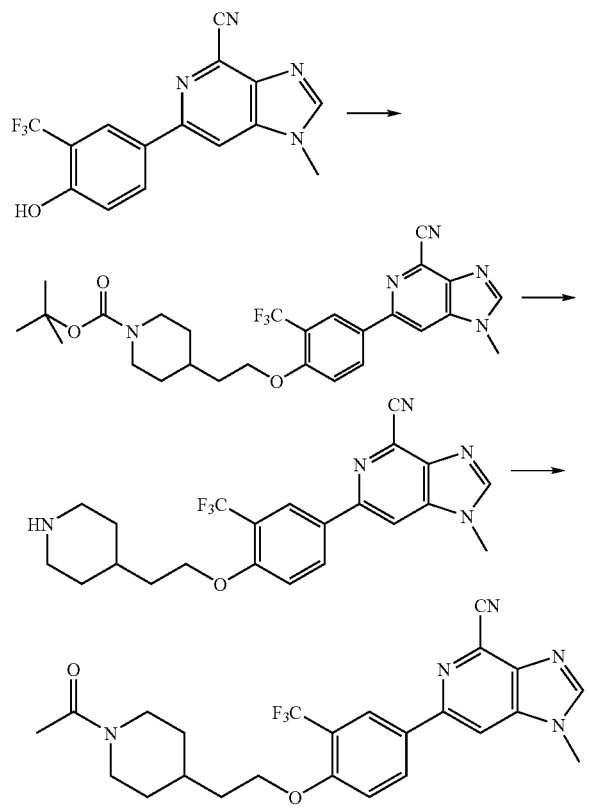

A: tert-butyl 4-(2-(4-(4-cyano-1-methyl-1H-imidazo[4,5-c]pyridin-6-yl)-2-(trifluoromethyl)phenoxy)ethyl)piperidine-1-carboxylate Diisopropyl azodicarboxylate (380 mg) was added with stirring at room temperature under nitrogen atmosphere to a mixture of 6-(4-hydroxy-3-trifluoro-methyl-phenyl)-1-methyl-1H-imidazo[4,5-c]pyridine-4-carbonitrile (300 mg), resin bound triphenylphosphine (3 mmol/g, 630 mg) and tert-butyl 4-(2-hydroxyethyl)-piperidine-1-carboxylate (430 mg) in DCM (2 ml). The mixture was then shaken for 8 hours. After filtering off resin, the filtrate was concentrated under reduced pressure, the residue columned on silica gel using ethyl acetate as eluant to give tert-butyl 4-(2-(4-(4-cyano-1-methyl-1H-imidazo[4,5-c]pyridin-6-yl)-2-(trifluoromethyl)phenoxy)-ethyl)piperidine-1-carboxylate as a white solid. ¹H NMR (CDCl₃) δ: 8.27 (d, 1H), 8.21 (s, 1H), 8.08 (s, 1H), 7.86 (s, 1H), 7.10 (d, 1H), 4.18 (t, 2H), 4.10 (m, 2H), 3.98 (s, 3H), 2.75 (m, 2H), 1.7-1.9 (m, 5H), 1.46 (s, 9H), 1.21 (m, 2H). MS m/z 530 (M+1).

B: 1-Methyl-6-{4-[2-(piperidin-4-yl)-ethoxy]-3-(trifluoromethyl)-phenyl}-1H-imidazo[4,5-c]pyridine-4-carbonitrile tert-Butyl 4-(2-(4-(4-cyano-1-methyl-1H-imidazo[4,5-c]pyridin-6-yl)-2-(trifluoromethyl)phenoxy)ethyl)piperidine-1-carboxylate (49 g) was dissolved in a mixed solvent of DCM (300 ml) and acetonitrile (150 ml), to this solution was then added trifluoroactetic acid (180 ml). After stirring at room temperature for 10 minutes, all solvent and excess trifluoroacetic acid was removed under reduced pressure. The residue was dissolved in ethyl acetate (200 ml) and diethyl ether (150 ml) was then added, the product as TFA salt slowly precipitated and was collected by filtration (44 g). ¹H NMR (CD3OD) δ: 8.44 (s, 1H), 8.40 (s, 1H), 8.38 (s, 1H), 8.39 (d, 1H), 7.31 (d, 1H), 4.27 (t, 2H), 4.02 (s, 3H), 3.42 (dm, 2H), 3.00 (t, 2H), 2.05 (d, 2H), 1.95 (m, 1H), 1.89 (m, 1H), 1.50 (m, 2H). MS m/z 430 (M+1).

Some of the TFA salt was then converted to HCl salt using the procedure described before by means of SCX. ¹H NMR (CD3OD) δ: 8.73 (s, 1H), 8.47 (s, 1H), 8.40 (s, 1H), 8.39 (d, 1H), 7.35 (d, 1H), 4.29 (t, 2H), 4.07 (s, 3H), 3.42 (dm, 2H), 3.00 (t, 2H), 2.06 (d, 2H), 1.98 (m, 2H), 1.90 (t, 2H), 1.50 (m, 2H). MS m/z 430 (M+1).

C: 6-{4-[2-(1-Acetylpiperidin-4-yl)-ethoxy]-3-(trifluoromethyl)-phenyl}-1-methyl-1H-imidazo[4,5-c]pyridine-4-carbonitrile Acetyl chloride (0.012 ml) was added dropwise to a solution of 1-methyl-(6-(4-(2-(piperidin-4-yl)ethoxy)-3-(trifluoromethyl)phenyl)-1H-imidazo[4,5-c]pyridine-4-carbonitrile (25 mg) and diisopropylethylamine (0.051 ml) in THF (2 ml). The reaction mixture was stirred at room temperature for 18 hours. The product was then purified by acidic prep HPLC to give 6-(4-(2-(1-acetylpiperidine-4-yl)-ethoxy)-3-(trifluoromethyl)phenyl)-1-methyl-1H-imidazo[4,5-c]pyridine-4-carbonitrile (7.2 mg).

¹H NMR (MeOD) δ: 8.45 (s, 1H), 8.35-8.30 (m, 3H), 7.30 (d, 1H), 4.55 (d, 1H), 4.24 (t, 2H), 4.02 (s, 3H), 3.94 (d, 1H), 3.12 (t, 1H), 2.66 (t, 1H), 2.10 (s, 3H), 1.86 (m, 5H), 1.20 (m, 2H). MS m/z 472.2 (M+H).

The procedure described in Example 13a was further applied, using the appropriate alkylating agent, to prepare the following compounds:

13b: 1-methyl-6-(4-(2-(1-probionylpiperidine-4-yl)ethoxy)-3-(trifluoromethyl)phenyl)-1-methyl-1H-imidazo[4,5-c]pyridine-4-carbonitrile

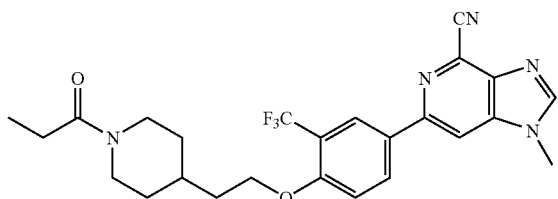

¹H NMR (MeOD) δ: 8.44 (s, 1H), 8.36-8.31 (m, 3H), 7.31 (d, 1H), 4.52 (d, 1H), 4.24 (t, 2H), 4.02 (s, 3H), 3.09 (t, 1H), 2.64 (t, 1H), 2.42 (q, 2H), 1.95-1.83 (m, 5H), 1.30-1.10 (m, 5H). MS m/z 486.2 (M+H).

13c: 1-methyl-6-(4-(2-(1-isobutyrylpiperidine-4-yl)ethoxy)-3-(trifluoromethyl)phenyl)-1-methyl-1H-imidazo[4,5-c]pyridine-4-carbonitrile

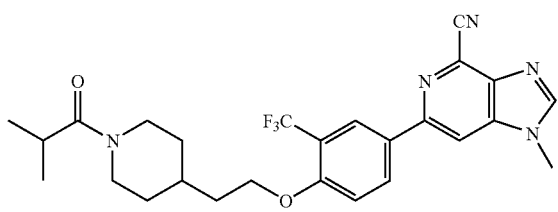

¹H NMR (MeOD) δ: 8.44 (s, 1H), 8.36-8.31 (m, 3H), 7.31 (d, 1H), 4.52 (d, 1H), 4.24 (t, 2H), 4.10 (d, 1H), 4.02 (s, 3H), 3.09 (t, 1H), 2.96 (m, 1H), 2.66 (t, 1H), 1.92-1.82 (m, 5H), 1.30-1.09 (m, 8H). MS m/z 500.2 (M+H).

13d: 1-methyl-6-(4-(2-(1-(pyrrolidine-1-carbonyl)piperidine-4-yl)ethoxy)-3-(trifluoromethyl)phenyl)-1-methyl-1H-imidazo[4,5-c]pyridine-4-carbonitrile

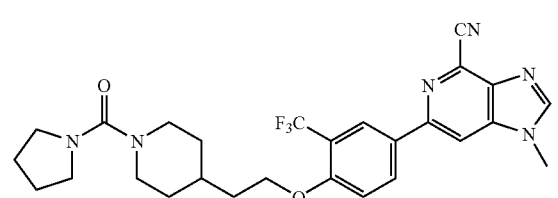

¹H NMR (MeOD) δ: 8.43 (s, 1H), 8.35-8.29 (m, 3H), 7.29 (d, 1H), 4.23 (t, 2H), 4.02 (s, 3H), 3.77 (d, 2H), 3.36 (m, 4H), 2.81 (t, 2H), 1.86-1.79 (m, 9H), 1.28 (m, 2H). MS m/z 527.2 (M+H).

13e: 1-methyl-6-(4-(2-(1-(morpholine-4-carbonyl)piperidine-4-yl)ethoxy)-3-(trifluoromethyl)phenyl)-1-methyl-1H-imidazo[4,5-c]pyridine-4-carbonitrile

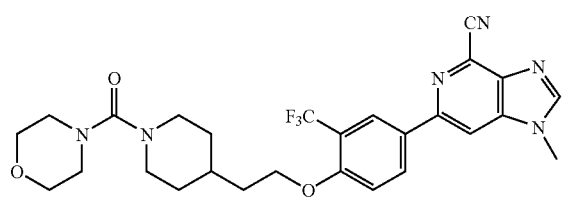

¹H NMR (MeOD) δ: 8.45 (s, 1H), 8.37-8.31 (m, 3H), 7.31 (d, 1H), 4.23 (t, 2H), 4.02 (s, 3H), 3.77 (d, 2H), 3.65 (m, 4H), 3.24 (m, 4H), 2.85 (t, 2H), 1.82-1.76 (m, 5H), 1.30 (m, 2H). MS m/z 543.2 (M+H).

13f: 4-(2-(4-(4-cyano-1-methyl-1H-imidazo[4,5-c]pyridin-6-O-2-(trifluoromethyl)phenoxy)ethyl)-N,N-dimethylpiperidine-1-carboxamide

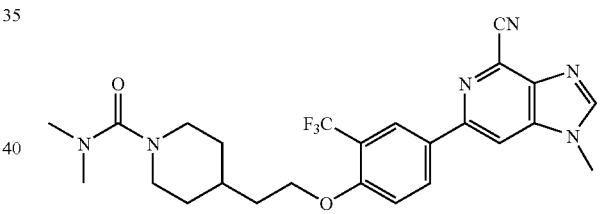

¹H NMR (MeOD) δ: 8.45 (s, 1H), 8.35-8.30 (m, 3H), 7.30 (d, 1H), 4.23 (t, 2H), 4.02 (s, 3H), 3.70 (d, 1H), 2.83-2.70 (m, 8H), 1.82-1.72 (m, 5H), 1.3 (m, 2H). MS m/z 501.2 (M+H).

13g: methyl-6-(4-(2-(1-(methylsulfonyl)piperidin-4-yl)ethoxy)-3-(trifluoromethyl)phenyl)-1H-imidazo[4,5-c]pyridine-4-carbonitrile

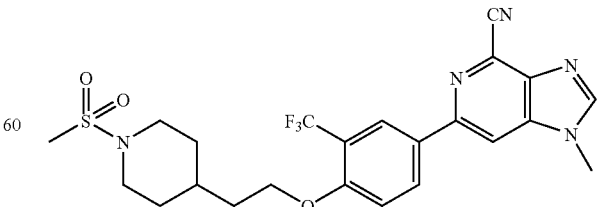

¹H NMR (DMSO) δ: 8.70 (s, 1H), 8.63 (s, 1H), 8.44-8.39 (m, 2H), 7.89 (d, 2H), 7.46 (d, 1H), 4.25 (t, 2H), 3.98 (s, 3H), 3.56 (d, 2H), 2.85 (s, 3H), 2.66 (t, 2H), 1.84-1.60 (m, 5H), 1.27 (m, 2H). MS m/z 508.2 (M+H).

EXAMPLE 14a 1-methyl-6-(4-(2-(1-(oxazol-2-ylmethyl)piperidin-4-yl)ethoxy)-3-(trifluoromethyl)phenyl)-1H-imidazo[4,5-c]pyridine-4-carbonitrile hydrochloride

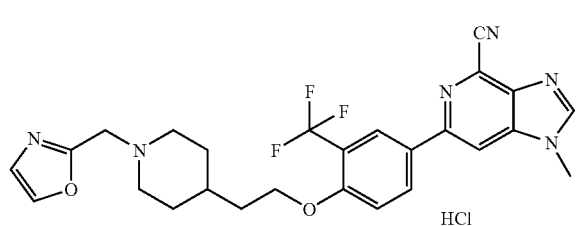

2-Chloromethyloxazole (140 mg) was added to the solution of 1-methyl-6-(4-(2-(piperidin-4-yl)-ethoxy)-3-(trifluoromethyl)-phenyl)-1H-imidazo[4,5-c]pyridine-4-carbonitrile TFA salt (330 mg) in methanol (2 ml) containing triethylamine (0.5 ml). The mixture was stirred at rt for 20 hours and then heated at 55° C. for 8 hours. After diluting with ethyl acetate (100 ml), washing with saturated sodium bicarbonate (50 ml), dried over sodium sulphate, solvent removed under vacuum, residue was then columned on silica gel using DCM:MeOH (95:5) as eluant to give 250 mg product as white solid. This solid was dissolved in THF (5 ml) and treated with 2M HCl in ether (1 ml). The product as HCl salt was collected by filtration and dried under high vacuum at 85° C. to give 260 mg product as white solid. $^1$H NMR (CD3OD) δ: 8.82 (s, 1H), 8.52 (s, 1H), 8.40 (s, 1H), 8.38 (d, 1H), 8.08 (s, 1H), 7.37 (d, 1H), 7.33 (s, 1H), 4.59 (s, 2H), 4.28 (t, 2H), 4.09 (s, 3H), 3.70 (m, 2H), 3.17 (m, 2H), 2.15 (m, 2H), 1.96 (m, 1H), 1.90 (m, 2H), 1.62 (m, 2H). MS m/z 511 (M+1).

The procedure described in Example 14a was further applied, using the appropriate alkylating agent, to prepare the following compounds as either TFA salt, free base or HCl salt:

14b: 1-methyl-6-(4-(2-(1-((5-methylisoxazol-3-yl)methyl)piperidin-4-yl)ethoxy)-3-(trifluoromethyl)phenyl)-1H-imidazo[4,5-c]pyridine-4-carbonitrile

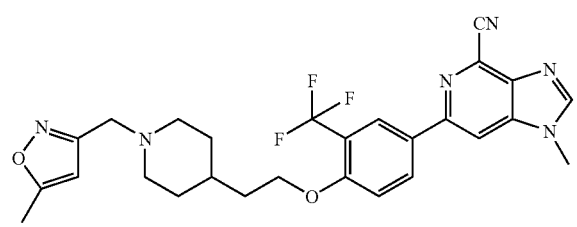

$^1$H NMR (CDCl3) δ: 8.28 (d, 1H), 8.20 (s, 1H), 8.07 (s, 1H), 7.86 (s, 1H), 7.09 (d, 1H), 6.00 (s, 1H), 4.17 (t, 2H), 3.98 (s, 3H), 3.54 (s, 2H), 2.90 (m, 2H), 2.40 (s, 3H), 2.08 (t, 2H), 1.81 (q, 2H), 1.74 (m, 2H), 1.60 (m, 1H), 1.38 (m, 2H). MS m/z 525 (M+1).

14c: 6-(4-(2-(1-((3,5-dimethylisoxazol-4-yl)methyl)piperidin-4-yl)ethoxy)-3-(trifluoromethyl)phenyl)-1-methyl-1H-imidazo[4,5-c]pyridine-4-carbonitrile

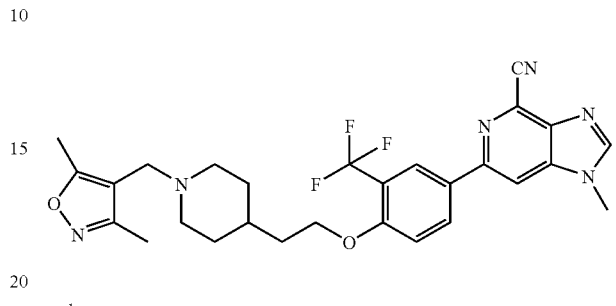

$^1$H NMR (CDCl3) δ: 8.27 (d, 1H), 8.20 (s, 1H), 8.07 (s, 1H), 7.86 (s, 1H), 7.08 (d, 1H), 4.17 (t, 2H), 3.98 (s, 3H), 3.19 (s, 2H), 2.80 (m, 2H), 2.33 (s, 3H), 2.25 (s, 3H), 1.90 (t, 2H), 1.80 (q, 2H), 1.72 (m, 2H), 1.60 (m, 1H), 1.26 (m, 2H). MS m/z 539 (M+1).

14d: 6-(4-(2-(1-(2-dimethylamino-2-oxo-ethyl)piperidin-4-yl)ethoxy)-3-(trifluoromethyl)phenyl)-1-methyl-1H-imidazo[4,5-c]pyridine-4-carbonitrile

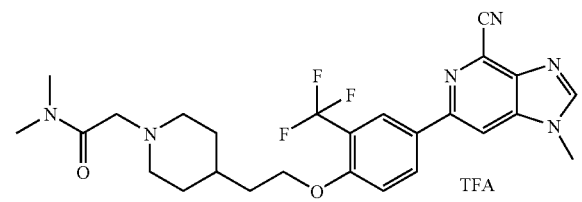

$^1$H NMR (CD3OD) δ: 8.44 (s, 1H), 8.39 (s, 2H), 8.37 (d, 1H), 7.33 (d, 1H), 4.30 (t, 2H), 4.18 (s, 2H), 4.02 (s, 3H), 3.67 (m, 2H), 3.05 (m, 2H), 2.10 (m, 2H), 2.0 (m, 1H), 1.90 (m, 2H), 1.67 (m, 2H). MS m/z 515 (M+1).

14e: 6-(4-(2-(1-(2-oxo-2-(pyrrolidin-1-yl)ethyl)piperidin-4-yl)ethoxy)-3-(trifluoromethyl)phenyl)-1-methyl-1H-imidazo[4,5-c]pyridine-4-carbonitrile

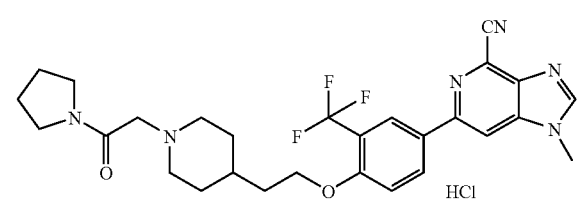

$^1$H NMR (CD3OD) δ: 8.65 (s, 1H), 8.45 (s, 1H), 8.40 (s, 1H), 8.39 (d, 1H), 7.35 (d, 1H), 4.29 (t, 2H), 4.11 (s, 2H), 4.06

(s, 3H), 3.67 (m, 2H), 3.50 (t, 2H), 3.07 (t, 2H), 3.07 (t, 2H), 1.8-2.2 (m, 9H), 1.67 (m, 2H). MS m/z 541 (M+1).

14f: 6-(4-(2-(1-(2-fluoroethyl)piperidin-4-yl)ethoxy)-3-(trifluoromethyl)phenyl)-1-methyl-1H-imidazo[4,5-c]pyridine-4-carbonitrile

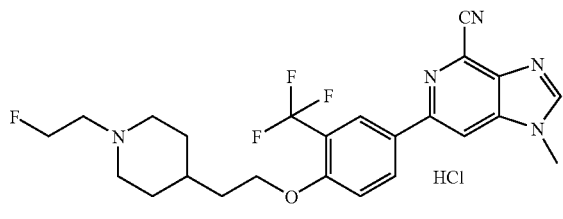

¹H NMR (CD3OD) δ: 8.56 (s, 1H), 8.44 (s, 1H), 8.39 (s, 1H), 8.37 (d, 1H), 7.37 (d, 1H), 4.84 (tt, 2H), 4.29 (t, 2H), 4.04 (s, 3H), 3.67 (m, 2H), 3.50 (tt, 2H), 3.10 (t, 2H), 2.13 (m, 2H), 2.0 (m, 1H), 1.90)m, 2H), 1.53 (m, 2H). MS m/z 476 (M+1).

14g: 6-(4-(2-(1-(2,2-difluoroethyl)piperidin-4-yl)ethoxy)-3-(trifluoromethyl)phenyl)-1-methyl-1H-imidazo[4,5-c]pyridine-4-carbonitrile

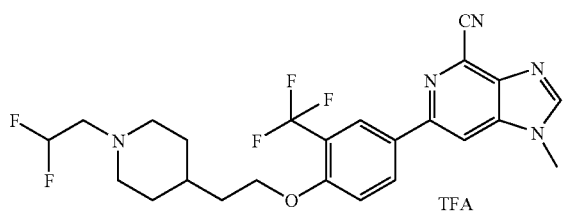

¹H NMR (CD3OD) δ: 8.45 (s, 1H), 8.39 (s, 1H), 8.38 (s, 1H), 8.37 (d, 1H), 7.34 (d, 1H), 6.42 (tt, 1H), 428 (t, 2H), 4.02 (s, 3H), 3.6-3.8 (m, 4H), 3.2 (m, 2H), 2.12 (m, 2H), 2.0 (m, 1H), 1.90 (m, 2H), 1.53 (m, 2H). MS m/z 494 (M+1).

14h: 6-(4-(2-(1-(2-methoxyethyl)piperidin-4yl)ethoxy)-3-(trifluoromethyl)phenyl)-1-methyl-1H-imidazo[4,5-c]pyridine-4-carbonitrile

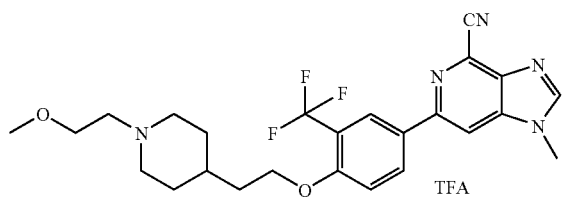

¹H NMR (CD3OD) δ: 8.46 (s, 1H), 8.41 (s, 1H), 8.40 (s, 1H), 8.39 (d, 1H), 7.35 (d, 1H), 4.28 (t, 2H), 4.03 (s, 3H), 3.71 (t, 2H), 3.62 (m, 2H), 3.43 (s, 3H), 3.3 (t, 2H), 3.0 (t, 2H), 2.10 (m, 2H), 2.0 (m, 1H), 1.90 (m, 2H), 1.60 (m, 2H). MS m/z 488 (M+1).

14i: 1-methyl-6-(4-(2-(1-(thiazol-2-ylmethyl)piperidin-4-yl)ethoxy)-3-(trifluoromethyl)-phenyl)-1H-imidazo[4,5-c]pyridine-4-carbonitrile

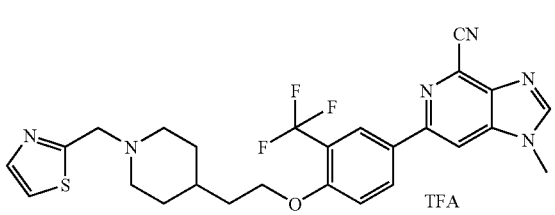

¹H NMR (CDCl₃) δ: 8.22 (s, 1H), 8.20 (d, 1H), 8.13 (s, 1H), 7.90 (s, 1H), 7.88 (d, 1H), 7.54 (d, 1H), 7.08 (d, 1H), 4.61 (s, 2H), 4.17 (t, 2H), 4.00 (s, 3H), 3.65 (m, 2H), 2.93 (m, 2H), 2.03 (m, 2H), 1.8-1.95 (m, 3H), 1.75 (m, 2H). MS m/z 527 (M+1).

14j: 1-methyl-6-(4-(2-(1-((5-methyl-1,2,4-oxadiazol-3-yl)methyl)piperidin-4-yl)ethoxy)-3-(trifluoromethyl)phenyl)-1H-imidazo[4,5-c]pyridine-4-carbonitrile

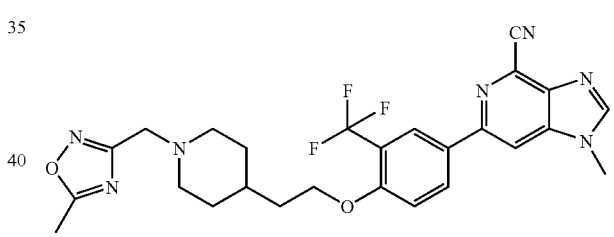

¹H NMR (CDCl₃) δ: 8.25 (d, 1H), 8.21 (s, 1H), 8.08 (s, 1H), 7.87 (s, 1H), 7.10 (d, 1H), 4.16 (t, 2H), 3.99 (s, 3H), 3.65 (s, 2H), 2.98 (m, 2H), 2.60 (s, 3H), 2.15 (t, 2H), 1.80 (m, 4H), 1.62 (m, 1H), 1.41 (m, 2H). MS m/z 526 (M+1).

14k: 1-methyl-6-(4-(2-(1-((3-methyl-1,2,4-oxadiazol-5-yl)methyl)piperidin-4-yl)-ethoxy)-3-(trifluoromethyl)phenyl)-1H-imidazo[4,5-c]pyridine-4-carbonitrile

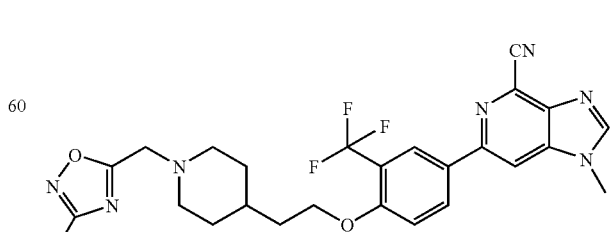

¹H NMR (CD3OD) δ: 8.44 (s, 1H), 8.36 (m, 3H), 7.31 (d, 1H), 4.23 (t, 2H), 4.02 (s, 3H), 3.85 (s, 2H), 2.99 (m, 2H), 2.37 (s, 3H), 2.24 (t, 2H), 1.80 (m, 5H), 1.65 (m, 2H). MS m/z 526 (M+1).

14l: 1-methyl-6-(4-(2-(1-((5-methyl-1,3,4-oxadiazol-2-yl)ethoxy)piperidin-4-yl)ethoxy)-3-(trifluoromethyl)phenyl)-1H-imidazo[4,5-c]pyridine-4-carbonitrile

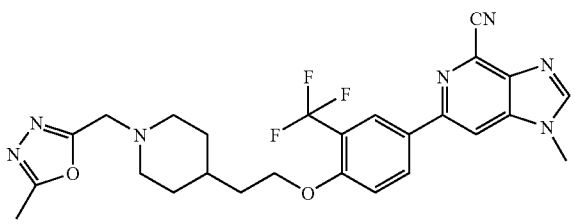

¹H NMR (CD3OD) δ: 8.44 (s, 1H), 8.38 (s, 1H), 8.37 (s, 1H), 8.33 (d, 1H), 7.29 (d, 1H), 4.22 (t, 2H), 4.02 (s, 3H), 3.80 (s, 2H), 2.95 (m, 2H), 2.54 (s, 3H), 2.20 (t, 2H), 1.79 (m, 4H), 1.65 (m, 1H), 1.38 (m, 2H). MS m/z 526.8 (M+H).

14m: 1-methyl-6-(4-(2-(1-((3-methylisoxazol-54) methyl)piperidin-4-yl)ethoxy)-3-(trifluoromethyl) phenyl)-1H-imidazo[4,5-c]pyridine-4-carbonitrile

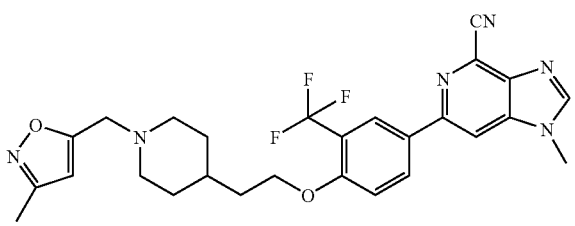

¹H NMR (DMSO) δ: 8.71 (s, 1H), 8.64 (s, 1H), 8.44 (d, 1H), 8.40 (s, 1H), 7.43 (d, 1H), 6.23 (s, 1H), 4.23 (t, 2H), 3.99 (s, 3H), 3.59 (s, 2H), 2.80 (m, 2H), 2.21 (s, 3H), 1.98 (m, 2H), 1.70 (m, 4H), 1.47 (m, 1H), 1.22 (m, 2H). MS m/z 525 (M+1).

EXAMPLE 15

6-(4-((6-(methylaminocarbonyl)pyridin-2-yl)methoxy)-3-(trifluoromethyl)phenyl)-1H-imidazo[4,5-c]pyridine-4-carbonitrile

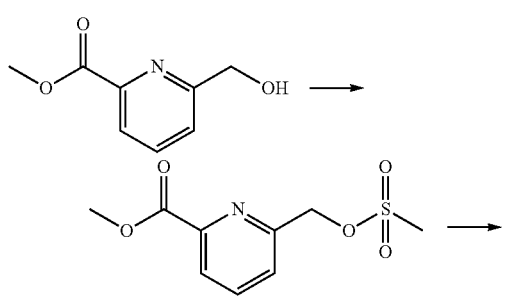

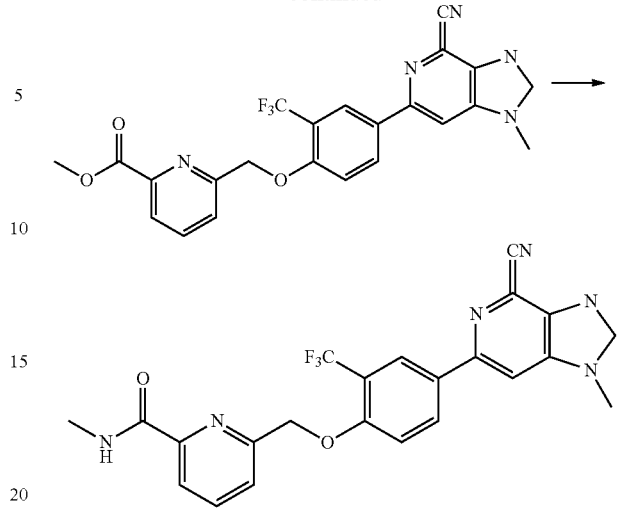

A: methyl 6-((methylsulfonyloxy)methyl)picolinate

Methanesulphonyl chloride (0.28 ml) was added at 0° C. to a solution of methyl 6-hydroxymethylpicolinate (500 mg), TEA (0.5 ml) in DCM (5 ml). The mixture was stirred at rt for 1 hour, then diluted with DCM (50 ml) and washed with water (2×30 ml). Organic layer dried, solvent removed under vacuum to give expected product methyl 6-((methylsulfonyloxy)methyl)picolinate (770 mg). ¹H NMR (CDCl₃) δ: 8.11 (d, 1H), 7.93 (t, 1H), 7.70 (d, 1H), 5.44 (s, 2H), 4.01 (s, 3H), 3.16 (s, 3H).

B: methyl 6-((4-(4-cyano-1-methyl-1H-imidazo[4,5-c]pyridin-6-yl)-2-(trifluoromethyl)-phenoxy)methyl) picolinate A mixture of methyl 6-((methylsulfonyloxy)methyl)picolinate (733 mg), 6-(4-hydroxy-3-(trifluoromethyl)phenyl)-1-methyl-1H-imidazo[4,5-c]pyridine-4-carbonitrile (950 mg), sodium iodide (44 mg) and potassium carbonate (830 mg) in acetonitrile (20 ml) was heated at 80° C. for 14 hours. After cooling to room temperature, water (30 ml) was added, the white precipitate was collected by filtration and washed with cold methanol (20 ml) to give methyl 6-((4-(4-cyano-1-methyl-1H-imidazo[4,5-c]pyridin-6-yl)-2-(trifluoromethyl) phenoxy)methyl)picolinate (1.1 g). ¹H NMR (DMSO) δ: 8.81 (s, 1H), 8.71 (s, 1H), 8.53 (m, 2H), 8.20 (m, 1H), 8.11 (m, 1H), 7.83 (d, 1H), 7.63 (d, 1H), 5.60 (s, 2H), 4.06 (s, 3H), 3.98 (s, 3H). MS m/z 468 (M+1).

C: 6-(4-((6-(methylaminocarbonyl)pyridin-2-yl) methoxy)-3-(trifluoromethyl)phenyl)-1H-imidazo[4, 5-c]pyridine-4-carbonitrile The mixture of methyl 6-((4-(4-cyano-1-methyl-1H-imidazo[4,5-c]pyridin-6-yl)-2-(trifluoromethyl)phenoxy)methyl)picolinate (0.064 mmol, 30 mg) and methylamine in methanol (2M, 1 ml) was heated with microwaves at 120° C. for 10 minutes, then diluted with water (3 ml). The product was collected by filtration and washed with cold methanol (3 ml) to give 6-(4-((6-(methylaminocarbonyl)pyridin-2-yl) methoxy)-3-(trifluoromethyl)phenyl)-1H-imidazo[4,5-c]pyridine-4-carbonitrile (22 mg). ¹H NMR (DMSO) δ: 8.80 (s, 1H), 8.77 (m, 1H, NH), 8.76 (s, 1H), 8.54 (m, 2H), 8.16 (m, 1H), 8.06 (d, 1H), 7.76 (d, 1H), 7.59 (d, 1H), 5.58 (s, 2H), 4.04 (s, 3H). MS m/z 467 (M+1).

EXAMPLE 16

6-(4-((6-(dimethylaminocarbonyl)pyridin-2-yl)methoxy)-3-(trifluoromethyl)phenyl)-1H-imidazo[4,5-c]pyridine-4-carbonitrile

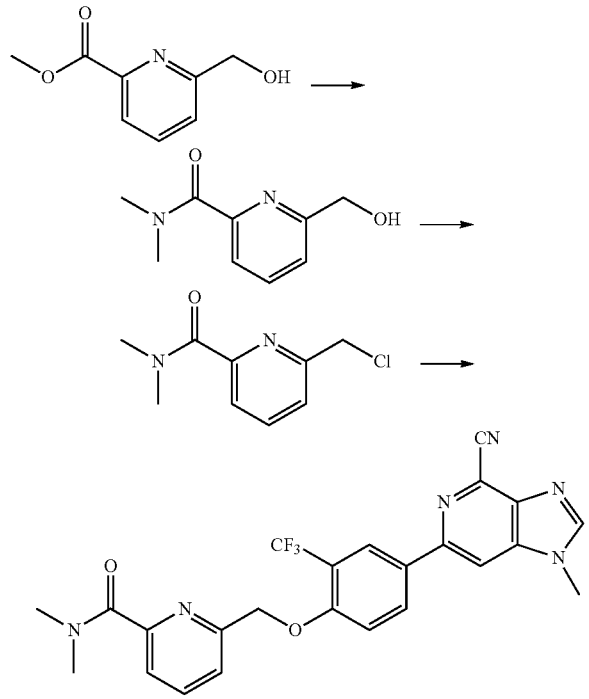

A: 6-(hydroxymethyl)-N,N-dimethylpicolinamide

Methyl 6-(hydroxymethyl)picolinate (0.598 mmol, 100 mg) was suspended in dimethylamine (2M in MeOH) (2.99 mmol, 1496 µl) and heated to 150° C. for 20 minutes in a microwave. Heating was repeated for a further 20 minutes then further dimethylamine (2M in MeOH) (2.99 mmol, 1496 µl) added and heating repeated again for 20 minutes. Solvent was evaporated under reduced pressure to yield 6-(hydroxymethyl)-N,N-dimethylpicolinamide (103% yield) as a clear oil. $^1$H NMR (CD3OD) δ: 7.95 (d, 1H), 7.82 (t, 1H), 7.50 (d, 1H), 4.75 (s, 2H), 2.73 (s, 6H).

B: 6-(chloromethyl)-N,N-dimethylpicolinamide

Mesyl chloride (0.924 mmol, 71.5 µl, 106 mg) was added to a stirred solution of 6-(hydroxymethyl)-N,N-dimethylpicolinamide (0.616 mmol, 111 mg) and DIPEA (1.232 mmol, 204 µl, 159 mg) in DCM (2000 µl) at 0° C. The reaction was allowed to warm to room temperature and stirred for two hours. The mixture was diluted with EtOAc (20 mL) and an excess of MeOH added. Stirring was continued for 15 minutes then the mixture washed with water. Organics were dried over sodium sulphate and solvent evaporated. NMR showed desired product obtained but MsCl remaining. The residue was re-dissolved in DCM and MeOH and heated to 40° C. for 15 minutes. Solvent was evaporated under reduced pressure to yield 6-(chloromethyl)-N,N-dimethylpicolinamide. $^1$H NMR (CDCl$_3$) δ: 7.88 (t, 1H), 7.62 (d, 1H), 7.52 (d, 1H), 5.34 (s, 2H), 3.15 (s, 6H).

C: 6-(4-((6-(dimethylaminocarbonyl)pyridin-2-yl)methoxy)-3-(trifluoromethyl)phenyl)-1H-imidazo[4,5-c]pyridine-4-carbonitrile 6-(4-hydroxy-3-(trifluoromethyl)phenyl)-1-methyl-1H-imidazo[4,5-c]pyridine-4-carbonitrile (0.157 mmol, 50 mg) 6-(chloromethyl)-N,N-dimethylpicolinamide (0.236 mmol, 46.8 mg) potassium carbonate (0.314 mmol, 43.4 mg) and sodium iodide (0.016 mmol, 2.355 mg) were suspended in acetonitrile (1571 µl) and heated to 80° C. for 16 hours, overnight. Solvent was evaporated under reduced pressure and the resulting solid suspended in EtOAc and water. The mixture was filtered and the solid then suspended in MeOH and stirred for 10 minutes. The mixture was filtered and the resulting solid washed with ether to yield 6-((4-(4-cyano-1-methyl-1H-imidazo[4,5-c]pyridin-6-yl)-2-(trifluoromethyl)phenoxy)methyl)-N,N-dimethylpicolinamide (59.9% yield). $^1$H NMR (DMSO) δ: 8.74 (s, 1H), 8.65 (s, 1H), 8.46 (m, 2H), 8.03 (t, 1H), 7.59 (d, 1H), 7.52 (m, 2H), 5.48 (s, 2H), 3.99 (s, 3H), 3.02 (s, 3H), 2.94 (s, 3H). MS m/z 481.0 (M+H).

EXAMPLE 17

6-(4-(3-acetylaminobenzoxy)-3-(trifluoromethyl)phenyl)-1H-imidazo[4,5-c]pyridine-4-carbonitrile

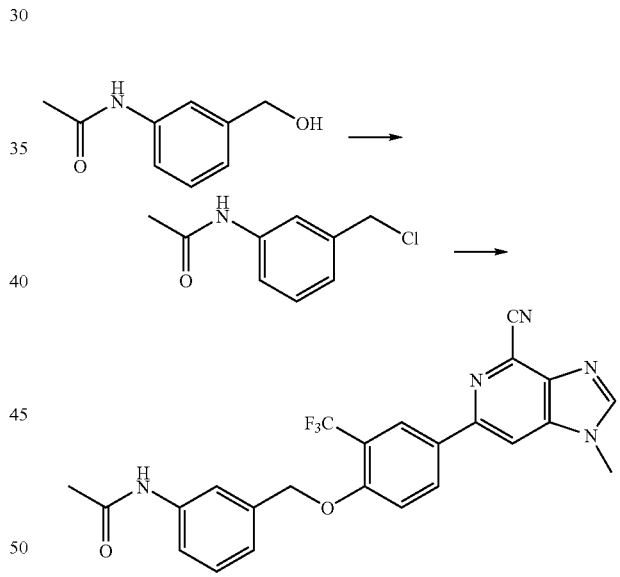

A: 3-acetylaminobenzylchloride

Methanesulphonyl chloride (0.15 ml) was added to a stirred solution of 3-acetylaminobenzylalcohol (260 mg) and TEA (0.26 ml) in DCM (2 ml) at 0° C. The reaction was allowed to warm to room temperature and stirred for two hours. The mixture was diluted with EtOAc (20 mL) and MeOH (1 ml) and stirred for 5 minutes. The mixture was then washed with water (30 ml), organic layer was dried over sodium sulphate and solvent evaporated. The residue was columned on silica gel using DCM then ethyl acetate as eluant to give 3-acetylaminobenzylchloride (210 mg). $^1$H NMR (CDCl$_3$) δ: 7.59 (s, 1H), 7.41 (d, 1H), 7.31 (t, 1H), 7.14 (d, 1H), 4.56 (s, 2H), 2.18 (s, 3H).

B: 6-(4-(3-acetylaminobenzoxy)-3-(trifluoromethyl) phenyl)-1H-imidazo[4,5-c]pyridine-4-carbonitrile A mixture of 3-acetylaminobenzylchloride (200 mg), 6-(4-hydroxy-3-(trifluoromethyl)-phenyl)-1-methyl-1H-imidazo[4,5-c]pyridine-4-carbonitrile (350 mg), sodium iodide (16 mg) and potassium carbonate (300 mg) in acetonitrile (20 ml) was heated at 80° C. for 14 hours. After cooling to room temperature, water (30 ml) was added, the white precipitate collected by filtration was dissolved in DMSO (1 ml) and purified by HPLC to give 6-(4-(3-acetylaminobenzoxy)-3-(trifluoromethyl)phenyl)-1H-imidazo[4,5-c]pyridine-4-carbonitrile. $^{1}$H NMR (DMSO) δ: 8.71 (s, 1H), 8.64 (s, 1H), 8.43 (m, 2H), 7.74 (s, 1H), 7.51 (m, 2H), 7.33 (t, 1H), 7.15 (d, 1H), 5.34 (s, 2H), 3.98 (s, 3H), 2.04 (s, 3H). MS m/z 466 (M+1).

EXAMPLE 18

6-(4-(2-(4,4-dimethyl-5-oxo-4,5-dihydro-1H-imidazol-1-yl)ethoxy)-3-(trifluoromethyl)phenyl)-1-methyl-1H-imidazo[4,5-c]pyridine-4-carbonitrile TFA salt

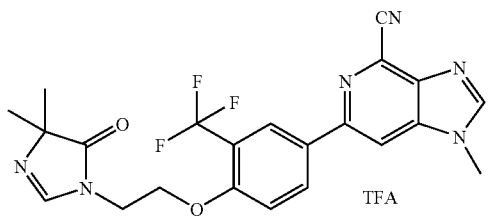

TFA 3-(4-(4-Cyano-1-methyl-1H-imidazo[4,5-c]pyridin-6-yl)-2-(trifluoromethyl)-phenoxy)ethyl methanesulfonate (100 mg) 5,5-dimethyl-1H-imidazol-4(5H)-one (55 mg) and potassium carbonate (91 mg) were dissolved in DMF (500 μl) and heated to 120° C. in a microwave for 30 minutes. HPLC purification afforded 6-(4-(3-(4,4-dimethyl-5-oxo-4,5-dihydro-1H-imidazol-1-yl)ethoxy)-3-(trifluoromethyl)phenyl)-1-methyl-1H-imidazo[4,5-c]pyridine-4-carbonitrile as TFA salt. $^{1}$H NMR (DMSO) δ: 8.73 (s, 1H), 8.65 (s, 1H), 8.44 (d, 1H), 8.41 (s, 1H), 8.13 (s, 1H), 7.47 (d, 1H), 4.41 (t, 2H), 3.99 (s, 3H), 3.91 (t, 2H), 1.20 (s, 6H). MS m/z 457 (M+H).

EXAMPLE 19

6-(4-(3-(5,5-dimethyl-4-oxo-4,5-dihydro-1H-imidazol-1-yl)propoxy)-3-(trifluoromethyl)phenyl)-1-methyl-1H-imidazo[4,5-c]pyridine-4-carbonitrile TFA salt

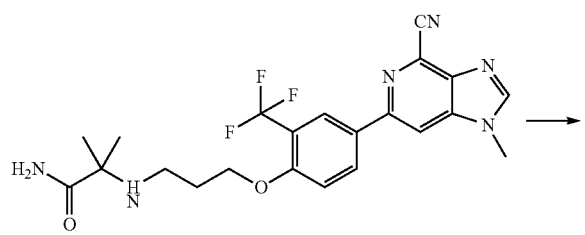

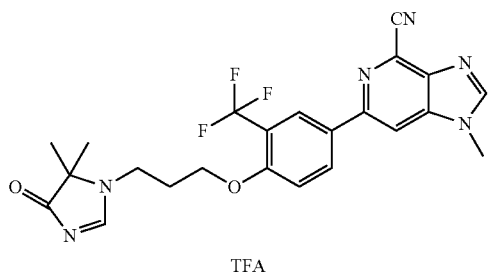

TFA 2-(3-(4-(4-Cyano-1-methyl-1H-imidazo[4,5-c]pyridin-6-yl)-2-(trifluoromethyl)-phenoxy)propylamino)-2-methyl-propanamide (51 mg) triethylorthoformate (500 μl) and AcOH (63.4 μl) were suspended in DCM (500 μl) and heated to 100° C. in a microwave for 15 minutes. HPLC purification afforded 6-(4-(3-(5,5-dimethyl-4-oxo-4,5-dihydro-1H-imidazol-1-yl)propoxy)-3-(trifluoromethyl)phenyl)-1-methyl-1H-imidazo[4,5-c]pyridine-4-carbonitrile as TFA salt. $^{1}$H NMR (CD3OD) δ: 9.54 (s, 1H), 8.46 (s, 1H), 8.41 (d, 3H), 7.36 (d, 1H), 4.37 (t, 2H), 4.02 (s, 3H), 3.97 (t, 2H), 2.45 (m, 2H), 1.60 (s, 6H). MS m/z 471 (M+H).

EXAMPLE 20

6-(4-(2-(4-fluoropiperidin-4-yl)ethoxy)-3-(trifluoromethyl)phenyl)-1-methyl-1H-imidazo[4,5-c]pyridine-4-carbonitrile hydrochloride

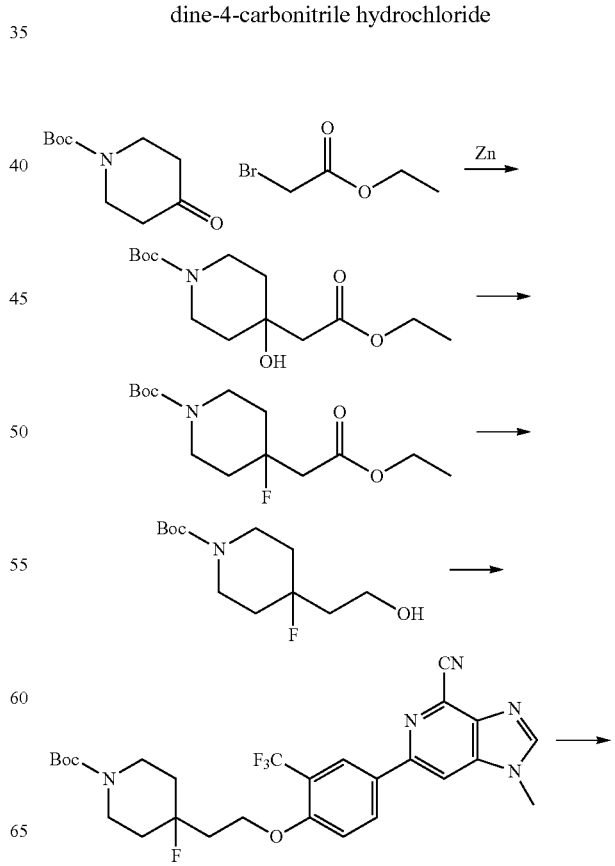

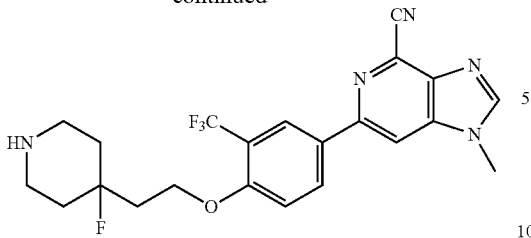

A: tert-butyl 4-(2-ethoxy-2-oxoethyl)-4-hydroxypiperidine-1-carboxylate

Iodine (12.7 g) was added to the suspension of zinc dust (20 g) in dry THF (200 ml) under nitrogen. An exothermic reaction takes place within 2 minutes and iodine disappeared in less the 10 minutes (a cold water bath is ready to cool the reaction down, but not used). To above mixture was then added by syringe a solution of mixture of ethyl bromoacetate (10.9 g) and N-Boc-4-piperidinone (10 g) in THF (50 ml) on the speed to maintain the reaction at gentle reflux. After stirring for 2 more hours, this mixture was then poured to the mixture of aqueous sodium bicarbonate (200 ml) and ethyl acetate (500 ml). Organic layer was seperated, washed with brine (200 ml), dried over sodium sulphate, solvent removed, the residue was columned on silica gel using heptane:EtOAc (10:1) as eluant to give expected product as a colourless oil (13.1 g). $^1$H NMR (CDCl$_3$) δ: 4.18 (q, 2H), 3.80 (br, 2H), 3.57 (s, 1H), 3.22 (t, br, 2H), 2.46 (s, 2H), 1.67 (m, 2H), 1.47 (m, 2H), 1.46 (s, 9H), 1.28 (t, 3H).

B: tert-butyl 4-(2-ethoxy-2-oxoethyl)-4-fluoropiperidine-1-carboxylate

To tert-butyl 4-(2-ethoxy-2-oxoethyl)-4-hydroxypiperidine-1-carboxylate (12 g) in DCM (60 ml) at −78° C. under nitrogen was added by syringe diethylaminosulfur trifluoride (DAST) (8.3 ml). The mixture was stirred at −78° C. for 3 hours, then slowly warming up to rt, the mixture was then poured to aqueous sodium bicarbonate (200 ml), extracted with ethyl acetate (200 ml+100 ml), organic layer dried over sodium sulphate, solvent removed under vacuum. The oily residue was taken into ethanol (150 ml) and water (150 ml). Magnesium sulphate (5.4 g) was then added, followed by potassium permanganate (7.2 g). The mixture was stirred at rt for 1 hour, then extracted with ethyl acetate (600 ml). Organic layer was washed with brine (150 ml), dried over sodium sulphate, solvent removed under vacuum, residue was columned on silica gel using heptane:EtOAc (7:1) as eluant to give tert-butyl 4-(2-ethoxy-2-oxoethyl)-4-fluoropiperidine-1-carboxylate (3.8 g) as a colourless oil. $^1$H NMR (CDCl3) δ: 4.16 (q, 2H), 3.95 (br, 2H), 3.10 (t, br, 2H), 2.64 (d, 2H), 1.93 (t, br, 2H), 1.6-1.85 (m, 2H), 1.46 (s, 9H), 1.27 (t, 3H).

C: tert-butyl 4-fluoro-4-(2-hydroxyethyl)piperidine-1-carboxylate

To tert-butyl 4-(2-ethoxy-2-oxoethyl)-4-fluoropiperidine-1-carboxylate (3.8 g) in DCM (20 ml) at −78° C. under nitrogen was added by syringe diisobutylaluminum hydride (2.2M in Toluene, 24 ml). The mixture was stirred at −78° C. for 2 hours, then warmed up to room temperature. The mixture was then poured to ice (100 g), acidified to pH 3, and extracted with ethyl acetate (200 ml+100 ml×3). Combined ethyl acetate layer was then dried over sodium sulphate, solvent removed to give tert-butyl 4-fluoro-4-(2-hydroxyethyl) piperidine-1-carboxylate which is contaminated with HF eliminated allylic alcohol in ~3:1 ratio in favour of desired product (3 g). As purification proved to be difficult, this was used for next step as a mixture.

D: tert-butyl 4-(2-(4-(4-cyano-1-methyl-1H-imidazo[4,5-c]pyridin-6-yl)-2-(trifluoromethyl)phenoxy) ethyl)-4-fluoropiperidine-1-carboxylate 6-(4-Hydroxy-3-(trifluoromethyl)phenyl)-1-methyl-1H-imidazo[4,5-c]pyridine-4-carbonitrile (2.2 g), tert-butyl 4-fluoro-4-(2-hydroxyethyl)piperidine-1-carboxylate (1.72 g, with contamination as mentioned above), triphenylphosphine (2.2 g) in DCM (50 ml) was cooled to 0-5° C. by a ice bath. To this solution was then added dropwise DIAD (diisopropyl azodicarboxylate) (1.65 ml). The mixture was stirred at 0° C. for 2 hours, then room temperature for another 2 hours. After removal of solvent under reduced pressure, the residue was then columned on silica gel using DCM:MeOH (100:2) as eluant to give 3.5 g solid product. This was then recrystalised from ethanol 3 times to give desired tert-butyl 4-(2-(4-(4-cyano-1-methyl-1H-imidazo[4,5-c]pyridin-6-yl)-2-(trifluoromethyl)phenoxy)ethyl)-4-fluoropiperidine-1-carboxylate (1.7 g) clean.

$^1$H NMR (CDCl3) δ: 8.26 (d, 1H), 8.22 (s, 1H), 8.09 (s, 1H), 7.85 (s, 1H), 7.12 (d, 1H), 4.30 (t, 2H), 3.99 (s, 3H), 3.95 (br, 2H), 3.12 (t, br, 2H), 2.2 (dt, 2H), 1.9 (t, br, 2H), 1.6-1.85 (m, 2H), 1.47 (s, 9H).

E: 6-(4-(2-(4-fluoropiperidin-4-yl)ethoxy)-3-(trifluoromethyl)phenyl)-1-methyl-1H-imidazo[4,5-c]pyridine-4-carbonitrile hydrochloride To tert-butyl 4-(2-(4-(4-cyano-1-methyl-1H-imidazo[4,5-c]pyridin-6-yl)-2-(trifluoromethyl)phenoxy)ethyl)-4-fluoropiperidine-1-carboxylate (0.7 g) in DCM (15 ml) was added acetonitrile (10 ml), followed by trifluoroacetic acid (10 ml). The mixture was stirred at room temperature for 10 minutes, then solvent and excess TFA were removed under vacuum. The residue was taken into ethyl acetate (15 ml), and diethylether (20 ml) was then added. The white precipitate product was then collected by filtration to give desired product as a TFA salt (0.7 g). 50 mg of this TFA salt was then converted to free base by means of SCX, then to HCl salt by treating with 2M HCl in ether. $^1$H NMR (CD3OD) δ: 8.60 (s, 1H), 8.45 (s, 1H), 8.41 (s, 1H), 8.40 (d, 1H), 7.39 (d, 1H), 4.40 (t, 2H), 4.05 (s, 3H), 3.2-3.5 (m, 4H), 2.2-2.4 (m, 4H), 2.0-2.2 (m, 2H). MS m/z 448 (M+H).

EXAMPLE 21a 6-(4-(2-(1-(2,2-dimethylamino-2-oxoethyl)-4-fluoropiperidin-4-yl)ethoxy)-3-(trifluoromethyl)phenyl)-1-methyl-1H-imidazo[4,5-c]pyridine-4-carbonitrile hydrochloride

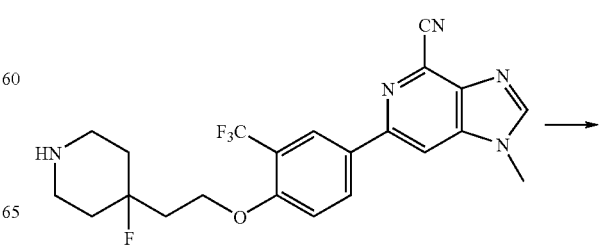

-continued

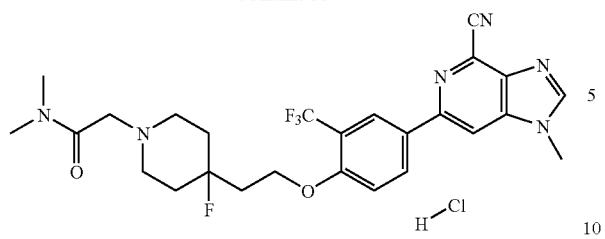

To 6-(4-(2-(4-fluoropiperidin-4-yl)ethoxy)-3-(trifluoromethyl)phenyl)-1-methyl-1H-imidazo[4,5-c]pyridine-4-carbonitrile (TFA salt, 600 mg) in methanol (3 ml) was added DIPEA (0.9 ml), followed by 2-chloro-N,N-dimethyl acetamide (390 mg). The mixture was heated at 55° C. for 20 minutes. After adding ammonia (2 ml, 7M in MeOH) and stirring at room temperature for 1 hour, the reaction mixture was poured to aqueous sodium bicarbonate (50 ml). The mixture was extracted with ethyl acetate (100 ml+50 ml×4). Combined organic layer was dried over sodium sulphate, solvent removed under vacuum, the residue columned on silica gel using 100:5 DCM:MeOH as eluant to give 6-(4-(2-(1-(2,2-dimethylamino-2-oxoethyl)-4-fluoropiperidin-4-yl) ethoxy)-3-(trifluoromethyl)phenyl)-1-methyl-1H-imidazo[4,5-c]pyridine-4-carbonitrile. The free base was then converted to HCl salt by treating with 2M HCl in ether (450 mg). $^1$H NMR (DMSO) δ: 9.75 (br, 1H), 8.72 (s, 1H), 8.65 (s, 1H), 8.46 (d, 1H), 8.43 (s, 1H), 7.50 (d, 1H), 4.40 (t, 2H), 4.3-4.5 (m, 4H), 4.00 (s, 3H), 3.48 (m, 2H), 3.20 (m, 2H), 2.94 (s, 3H), 2.91 (s, 3H), 2.0-2.4 (m, 6H). MS m/z 533 (M+H).

The procedure described in Example 21a was further applied, using the appropriate alkylating agent, to prepare the following compounds as either TFA salt, free base or HCl salt:

21b: 6-(4-(2-(4-fluoro-1-(2-methoxyethyl)piperidin-4-yl)ethoxy)-3-(trifluoromethyl)phenyl)-1-methyl-1H-imidazo[4,5-c]pyridine-4-carbonitrile TFA salt

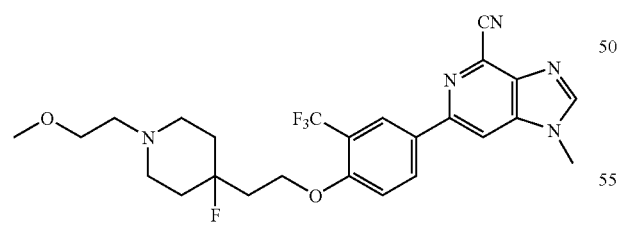

$^1$H NMR (CD3OD) δ: 8.44 (s, 1H), 8.38 (s, 1H), 8.37 (s, 1H), 8.35 (d, 1H), 7.35 (d, 1H), 4.39 (t, 2H), 4.02 (s, 3H), 3.74 (t, 2H), 3.60 (m, 2H), 3.43 (s, 3H), 3.40 (t, 2H), 3.30 (m, 2H), 2.0-2.4 (m, 6H). MS m/z 506 (M+H).

21c: 6-(4-(2-(1-ethyl-4-fluoro-piperidin-4-yl)ethoxy)-3-(trifluoromethyl)phenyl)-1-methyl-1H-imidazo[4,5-c]pyridine-4-carbonitrile TFA salt

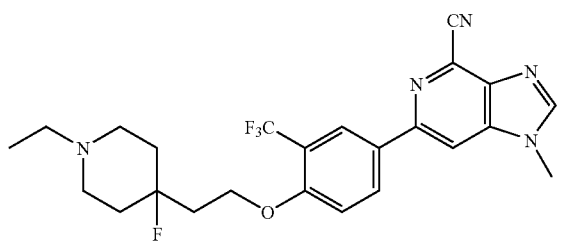

$^1$H NMR (CD3OD) δ: 8.43 (5, 1H), 8.36 (s, 2H), 8.35 (d, 1H), 7.35 (d, 1H), 4.39 (t, 2H), 4.02 (s, 3H), 3.58 (m, 2H), 3.15-3.3 (m, 4H), 2.25-2.4 (m, 4H), 2.0-2.25 (m, 2H), 1.38 (t, 3H). MS m/z 476 (M+H).

21d: 6-(4-(2-(4-fluoro-1-(2-fluoroethyl)piperidin-4-yl)ethoxy)-3-(trifluoromethyl)phenyl)-1-methyl-1H-imidazo[4,5-c]pyridine-4-carbonitrile TFA salt

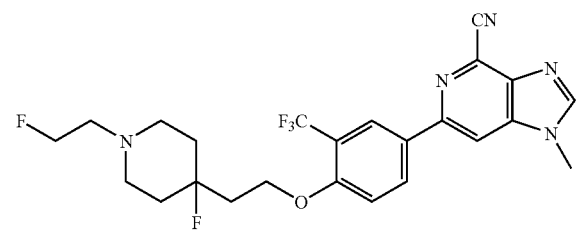

$^1$H NMR (CD3OD) δ: 8.43 (5, 1H), 8.34 (s, 1H), 8.33 (s, 1H), 8.32 (d, 1H), 7.32 (d, 1H), 4.9 (dt, 2H), 4.39 (t, 2H), 4.01 (s, 3H), 3.5-3.75 (m, 4H), 3.4 (m, 2H), 2.1-2.45 (m, 6H). MS m/z 494 (M+H).

EXAMPLE 22

6-(4-(2-(4-fluoro-1-methyl-piperidin-4-yl)ethoxy)-3-(trifluoromethyl)phenyl)-1-methyl-1H-imidazo[4,5-c]pyridine-4-carbonitrile TFA salt

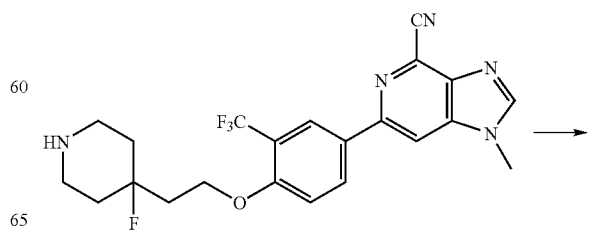

-continued

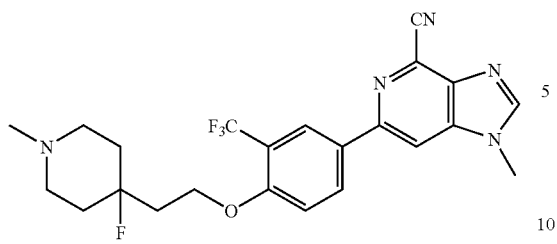

To 6-(4-(2-(4-fluoropiperidin-4-yl)ethoxy)-3-(trifluoromethyl)phenyl)-1-methyl-1H-imidazo[4,5-c]pyridine-4-carbonitrile (TFA salt, 100 mg) in acetonitrile/THF (2 ml, 1:1) was added formaldehyde (37%, 140 ul), acetic acid (0.3 ml), followed by sodium cyanoborohydride (100 mg). The mixture was stirred at room temperature for 2 hours, and then poured to aqueous sodium bicarbonate (10 ml). The mixture was then extracted with ethyl acetate (20 ml+10 ml×4). Combined organic layer was then dried over sodium sulphate. After removal of solvent under reduced pressure, the residue was purified by HPLC to give 6-(4-(2-(4-fluoro-1-methyl-piperidin-4-yl)ethoxy)-3-(trifluoromethyl)phenyl)-1-methyl-1H-imidazo[4,5-c]pyridine-4-carbonitrile as a TFA salt. $^1$H NMR (CD3OD) δ: 8.45 (s, 1H), 8.38 (s, 2H), 8.35 (d, 1H), 7.35 (d, 1H), 4.39 (t, 2H), 4.02 (s, 3H), 3.50 (m, 2H), 3.3 (m, 2H), 2.93 (s, 3H), 2.25-2.4 (m, 4H), 2.0-2.25 (m, 2H). MS m/z 462 (M+H).

EXAMPLE 23

1-methyl-6-(4-(2-(1-(thiazol-2-yl)piperidin-4-yl) ethoxy)-3-(trifluoromethyl)phenyl)-1H-imidazo[4,5-c]pyridine-4-carbonitrile TFA salt

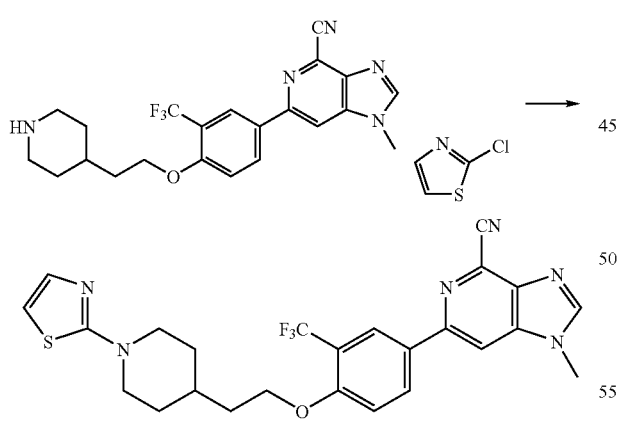

Methyl-6-{4-[2-(piperidin-4-yl)-ethoxy]-3-(trifluoromethyl)-phenyl}-1H-imidazo[4,5-c]pyridine-4-carbonitrile (50 mg), 2-chlorothiazole (33 mg) and triethylamine (60 uL) in DMSO (2 ml) was heated in a microwave at 180° C. for 20 minutes. The mixture was then purified by HPLC to afford 1-methyl-6-(4-(2-(1-(thiazol-2-yl)piperidin-4-yl)ethoxy)-3-(trifluoromethyl)phenyl)-1H-imidazo[4,5-c]pyridine-4-carbonitrile as TFA. Salt. $^1$H NMR (CD3OD) δ: 8.44 (s, 1H), 8.37 (s, 2H), 8.35 (d, 1H), 7.32 (d, 1H), 7.27 (d, 1H), 6.93 (d, 1H), 4.29 (t, 2H), 4.02 (s, 3H), 3.95 (d, 2H), 3.40 (t, 2H), 1.95-2.1 (m, 3H), 1.90 (m, 2H), 1.50 (m, 2H). MS m/z 513 (M+H).

EXAMPLE 24a 1-methyl-6-(4-(2-(1-(pyridin-2-piperidin-4-yl) ethoxy)-3-(trifluoromethyl)phenyl)-1H-imidazo[4,5-c]pyridine-4-carbonitrile TFA salt

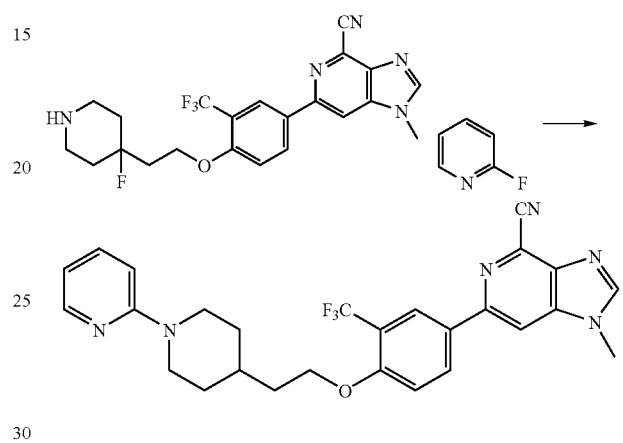

Methyl-6-{4-[2-(piperidin-4-yl)-ethoxy]-3-(trifluoromethyl)-phenyl}-1H-imidazo[4,5-c]pyridine-4-carbonitrile (50 mg), 2-fluoropyridine (38 mg) and triethylamine (60 uL) in DMSO (2 ml) was heated in a microwave at 180° C. for 20 minutes. The mixture was then purified by HPLC to afford 1-methyl-6-(4-(2-(1-(pyridin-2-yl)piperidin-4-yl)ethoxy)-3-(trifluoromethyl)phenyl)-1H-imidazo[4,5-c]pyridine-4-carbonitrile as TFA. Salt. $^1$H NMR (CD3OD) δ: 8.44 (s, 1H), 8.36 (s, 2H), 8.35 (d, 1H), 8.00 (t, 1H), 7.90 (d, 1H), 7.40 (d, 1H), 7.32 (d, 1H), 6.95 (t, 1H), 4.29 (t, 2H), 4.20 (d, 2H), 4.02 (s, 3H), 3.30 (t, 2H), 2.0-2.2 (m, 3H), 1.90 (m, 2H), 1.50 (m, 2H). MS m/z 506.9 (M+H).

The procedure described in Example 24a was further applied, using the appropriate fluoropyridine, to prepare the following compounds as either TFA salt, free base or HCl salt:

24b: 1-methyl-6-(4-(2-(1-(5-chloro-pyridin-2-piperidin-4-yl)ethoxy)-3-(trifluoromethyl)phenyl)-1H-imidazo[4,5-c]pyridine-4-carbonitrile TFA salt

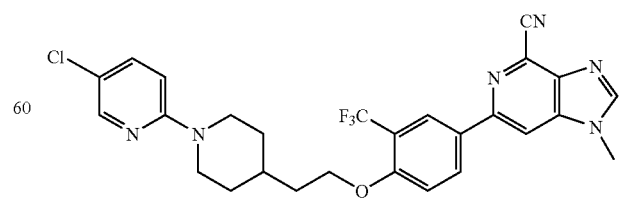

$^1$H NMR (CD3OD) δ: 8.44 (s, 1H), 8.37 (s, 2H), 8.35 (d, 1H), 7.99 (s, 1H), 7.76 (d, 1H), 7.35 (d, 1H), 7.15 (d, 1H), 4.28

(t, 2H), 4.25 (d, 2H), 4.02 (s, 3H), 3.10 (t, 2H), 1.95-2.10 (m, 3H), 1.90 (m, 2H), 1.49 (m, 2H). MS m/z 541 (M+H).

24c: 1-methyl-6-(4-(2-(1-(6-methyl-pyridin-2-yl)piperidin-4-yl)ethoxy)-3-(trifluoromethyl)phenyl)-1H-imidazo[4,5-c]pyridine-4-carbonitrile TFA salt

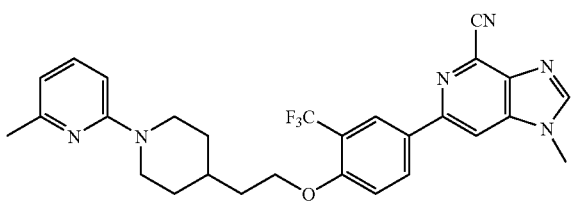

¹H NMR (CD3OD) δ: 8.44 (s, 1H), 8.38 (s, 2H), 8.35 (d, 1H), 7.89 (t, 1H), 7.34 (d, 1H), 7.20 (d, 1H), 6.75 (d, 1H), 4.28 (t, 2H), 4.25 (d, 2H), 4.02 (s, 3H), 3.26 (t, 2H), 2.55 (s, 3H), 1.95-2.10 (m, 3H), 1.90 (m, 2H), 1.50 (m, 2H). MS m/z 521 (M+H).

EXAMPLE 25a

N-(2-(4-(4-cyano-1-methyl-1H-imidazo[4,5-c]pyridin-6-yl)-2-(trifluoromethyl)-phenoxy)ethyl)-N-methyl-2-(methylamino)acetamide

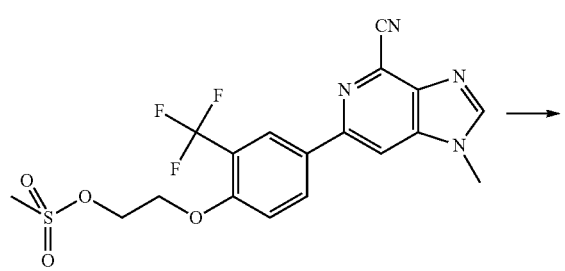

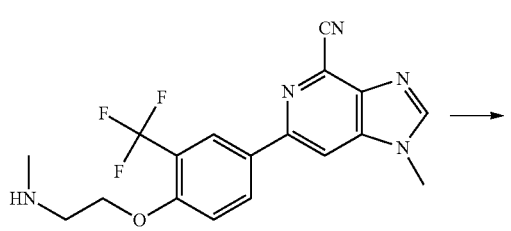

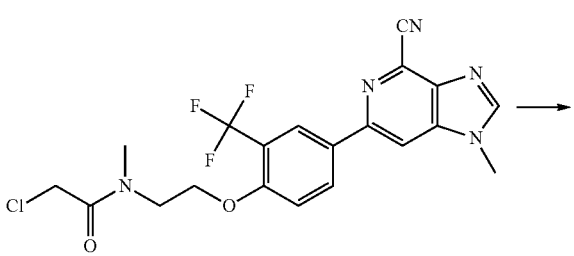

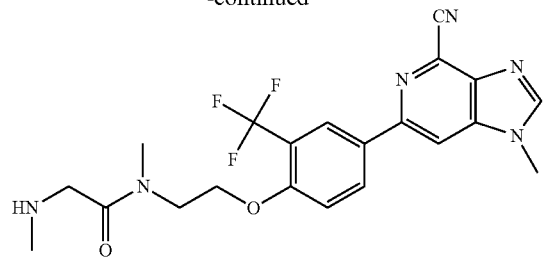

A: 1-methyl-6-(4-(2-(methylamino)ethoxy)-3-(trifluoromethyl)phenyl)-1H-imidazo[4,5-c]pyridine-4-carbonitrile 2M methylamine in THF (2.84 ml) was added to 2-(4-(4-cyano-1-methyl-1H-imidazo[4,5-c]pyridin-6-yl)-2-(trifluoromethyl)phenoxy)ethyl methanesulfonate (500 mg) dissolved in NMP (4 ml). Reaction mixture was heated at 100° C. under microwave conditions for 20 minutes. The reaction mixture was filtered and purified by acidic prep HPLC to give 1-methyl-6-(4-(2-(methylamino)ethoxy)-3-(trifluoromethyl)phenyl)-1H-imidazo[4,5-c]pyridine-4-carbonitrile as TFA salt. The free base was obtained by Cationic Exchange Column to afford 1-methyl-6-(4-(2-(methyl-amino)ethoxy)-3-(trifluoromethyl)phenyl)-1H-imidazo[4,5-c]pyridine-4-carbonitrile (211 mg). ¹H NMR (CDCL3) δ: 8.22 (m, 2H), 8.07 (s, 1H), 7.86 (s, 1H), 7.13 (d, 1H), 4.25 (t, 2H), 3.98 (s, 3H), 3.05 (t, 2H), 2.54 (s, 3H). MS m/z 376.0 (M+H).

B: 2-chloro-N-(2-(4-(4-cyano-1-methyl-1H-imidazo[4,5-c]pyridin-6-yl)-2-(trifluoromethyl)phenoxy)ethyl)-N-methylacetamide At 0° C., 2-chloroacetyl chloride (127 mg) was added to a solution of 1-methyl-6-(4-(2-(methylamino)ethoxy)-3-(trifluoromethyl)phenyl)-1H-imidazo[4,5-c]pyridine-4-carbonitrile (211 mg) and N-ethyl-N-isopropylpropan-2-amine (0.465 ml) dissolved in THF (5 ml). Reaction mixture was stirred at room temperature for 1 hour. Reaction mixture diluted with ethyl acetate, washed with sodium bicarbonate and water. Organic layer was dried over magnesium sulphate, solvent removed under vacuo to afford 2-chloro-N-(2-(4-(4-cyano-1-methyl-1H-imidazo[4,5-c]pyridin-6-yl)-2-(trifluoromethyl)phenoxy)ethyl)-N-methylacetamide (205 mg). ¹H NMR (CDCL3) δ: 8.22 (m, 2H), 8.08 (s, 1H), 7.87 (s, 1H), 7.13 (d, 1H), 4.32 (t, 2H), 4.13 (s, 2H), 3.99 (s, 3H), 3.88 (t, 2H), 3.29 (s, 3H). MS m/z 452.0 (M+H).

C: N-(2-(4-(4-cyano-1-methyl-1H-imidazo[4,5-c]pyridin-6-yl)-2-(trifluoromethyl)-phenoxy)ethyl)-N-methyl-2-(methylamino)acetamide 2M methylamine in methanol (0.276 ml) was added to 2-chloro-N-(2-(4-(4-cyano-1-methyl-1H-imidazo[4,5-c]pyridin-6-yl)-2-(trifluoromethyl)phenoxy)ethyl)-N-methylacetamide (25 mg) in MeOH (1 ml). Reaction mixture was heated at 90° C. under microwave conditions for 40 minutes, then filtered and purified by acidic prep HPLC to give expected product as TFA salt. The free base was obtained by cationic exchange column affording N-(2-(4-(4-cyano-1-methyl-1H-imidazo[4,5-c]pyridin-6-yl)-2-(trifluoromethyl)phenoxy)ethyl)-N-methyl-2-(methylamino)acetamide (4.4 mg). ¹H NMR (CDCL3) δ: 8.25 (m, 2H), 8.09 (s, 1H), 7.87 (s, 1H), 7.06 (d, 1H), 4.29 (t, 2H), 3.99 (s, 3H), 3.85 (t, 2H), 3.48 (s, 2H), 3.16 (s, 3H), 2.51 (s, 3H). MS m/z 447.2 (M+H).

The procedure described in Example 25a was further applied, using the appropriate amine, to prepare the following compounds:

25b: N-(2-(4-(4-cyano-1-methyl-1H-imidazo[4,5-c]pyridin-6-yl)-2-(trifluoromethyl)-phenoxy)ethyl)-2-(dimethylamino)-N-methylacetamide

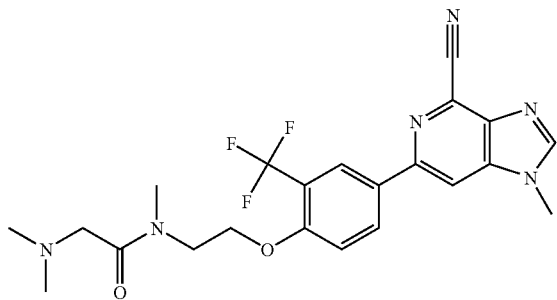

$^1$H NMR (CDCl3) δ: 8.25 (m, 2H), 8.09 (s, 1H), 7.87 (s, 1H), 7.09 (d, 1H), 4.30 (t, 2H), 4.00 (s, 3H), 3.24 (s, 3H), 3.19 (s, 2H), 2.37 (d, 6H). MS m/z 461.2 (M+H).

25c: N-(2-(4-(4-cyano-1-methyl-1H-imidazo[4,5-c]pyridin-6-yl)-2-(trifluoromethyl)-phenoxy)ethyl)-N-methyl-2-morpholinoacetamide

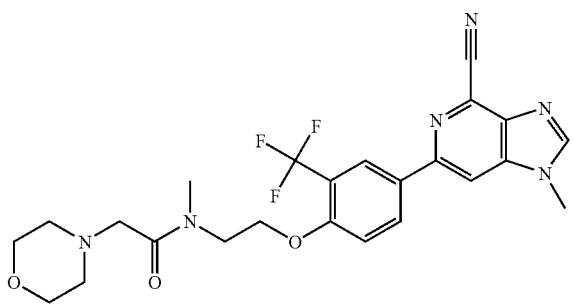

$^1$H NMR (CDCl3) δ: 8.25 (m, 2H), 8.09 (s, 1H), 7.87 (s, 1H), 7.09 (d, 1H), 4.31 (t, 2H), 4.00 (s, 3H), 3.83 (t, 2H), 3.75 (m, 4H), 3.25 (s, 3H), 3.06 (s, 2H), 2.60 (broad m, H). MS m/z 504.2 (M+H).

25d: N-(2-(4-(4-cyano-1-methyl-1H-imidazo[4,5-c]pyridin-6-yl)-2-(trifluoromethyl)-phenoxy)ethyl)-N-methyl-2-(pyrrolidin-1-yl)acetamide

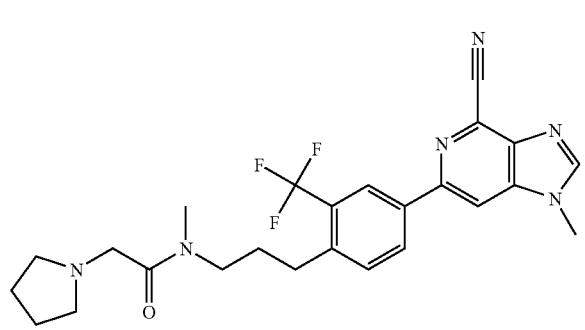

$^1$H NMR (CDCl3) δ: 8.25 (m, 2H), 8.09 (s, 1H), 7.87 (s, 1H), 7.09 (d, 1H), 4.31 (t, 2H), 4.00 (s, 3H), 3.83 (t, 2H), 3.50 (s, 2H), 3.21 (s, 3H), 2.82 (broad m, 4H), 1.87 (broad m, 4H). MS m/z 487.2 (M+H).

25e: N-(2-(4-(4-cyano-1-methyl-1H-imidazo[4,5-c]pyridin-6-yl)-2-(trifluoromethyl)-phenoxy)ethyl)-2-((2-methoxyethyl)(methylamino)-N-methylacetamide

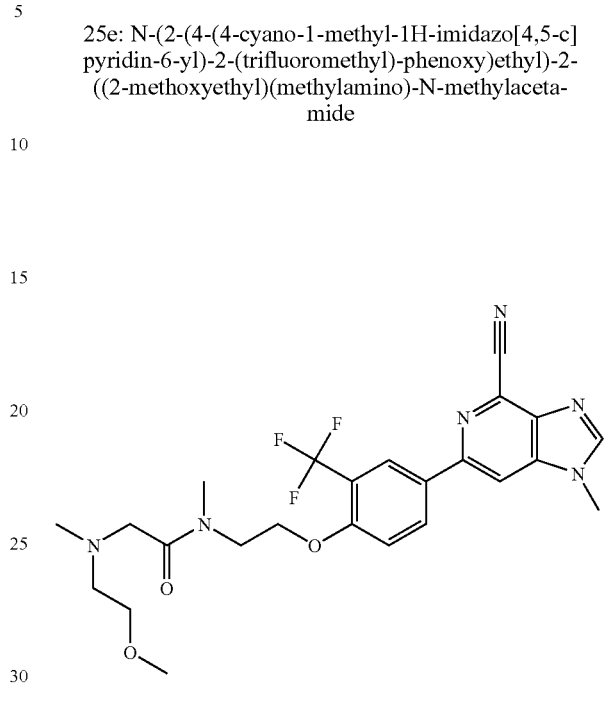

$^1$H NMR (CDCl3) δ: 8.25 (m, 2H), 8.10 (s, 1H), 7.89 (s, 1H), 7.10 (d, 1H), 4.31 (t, 2H), 3.99 (s, 3H), 3.89 (s, 3H), 3.66 (m, 2H), 3.35 (s, 2H), 3.19 (s, 3H), 2.79 (broad m, 2H)). MS m/z 505.2 (M+H).

25f: 2-(7-azabicyclo[2.2.1]heptan-7-yl)-N-(2-(4-(4-cyano-1-methyl-1H-imidazo[4,5-c]-pyridin-6-yl)-2-(trifluoromethyl)phenoxy)ethyl)-N-methylacetamide

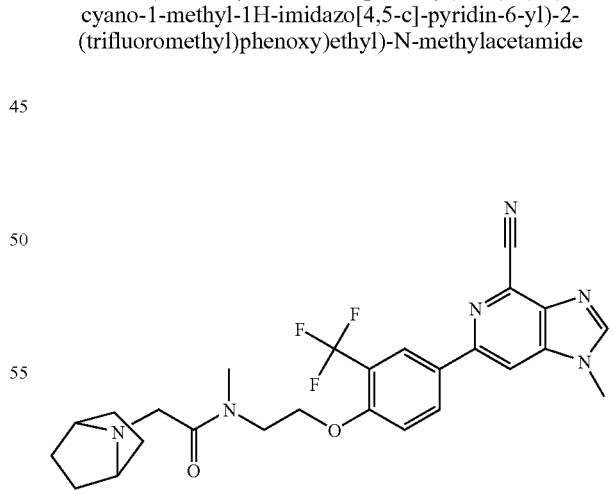

$^1$H NMR (CDCl3) δ: 8.25 (m, 2H), 8.08 (s, 1H), 7.87 (s, 1H), 7.08 (d, 1H), 4.31 (t, 2H), 4.00 (s, 3H), 3.81 (m, 2H), 3.40 (m, 1H), 3.33 (m, 1H), 3.24 (s, 3H), 3.07 (s, 2H), 1.77 (broad m, 4H), 1.30 (broad m, 4H). MS m/z 513.2 (M+H).

25g: N-(2-(4-(4-cyano-1-methyl-1H-imidazo[4,5-c]pyridin-6-yl)-2-(trifluoromethyl)phenoxy)ethyl)-N-methyl-2-(6-azaspiro[3.4]octan-6-yl)acetamide

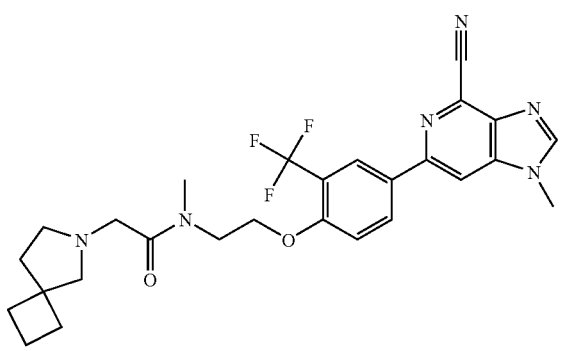

¹H NMR (CDCl₃) δ: 8.25 (m, 2H), 8.09 (s, 1H), 7.878 (s, 1H), 7.09 (d, 1H), 4.31 (t, 2H), 4.00 (s, 3H), 3.81 (m, 2H), 3.40 (m, 1H), 3.32 (s, 2H), 3.23 (s, 3H), 2.10-2.63 (m, 4H), 1.97-1.77 (m, 9H). MS m/z 527.2 (M+H).

25h: N-(3-(4-(4-cyano-1-methyl-1H-imidazo[4,5-c]pyridin-6-yl)-2-(trifluoromethyl)-phenoxy)propyl)-2-(dimethylamino)-N-methylacetamide

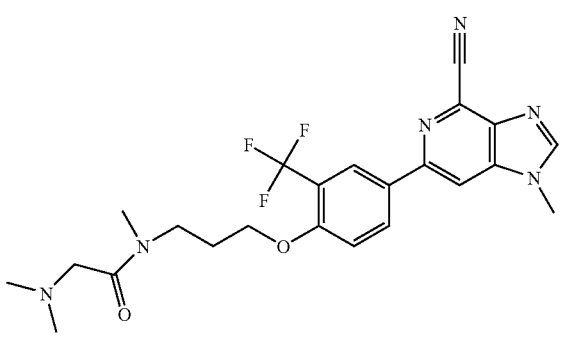

¹H NMR (CDCl₃) δ: 8.25 (m, 2H), 8.09 (s, 1H), 7.878 (s, 1H), 7.09 (d, 1H), 4.31 (t, 2H), 4.00 (s, 3H), 3.49 (m, 2H), 3.16 (S, 2H), 2.97 (s, 3H), 2.32 (s, 3H), 2.27 (s, 3H), 2.12 (m, 2H). MS m/z 475.2 (M+H).

25i: N-(3-(4-(4-cyano-1-methyl-1H-imidazo[4,5-c]pyridin-6-yl)-2-(trifluoromethyl)-phenoxy)propyl)-N-methyl-2-morpholinoacetamide

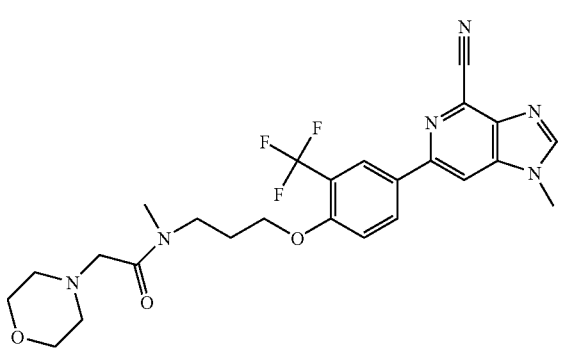

¹H NMR (CDCl₃) δ: 8.25 (m, 2H), 8.09 (s, 1H), 7.878 (s, 1H), 7.09 (d, 1H), 4.17 (t, 2H), 4.00 (s, 3H), 3.74 (broad m, 4H), 3.60 (m, 2H), 3.17 (s, 2H), 2.97 (3H), 2.50 (broad m, 4H), 2.16 (m, 2H). MS m/z 517.2 (M+H).

25j: N-(3-(4-(4-cyano-1-methyl-1H-imidazo[4,5-c]pyridin-6-yl)-2-(trifluoromethyl)-phenoxy)propyl)-N-methyl-2-(pyrrolidin-1-yl)acetamide

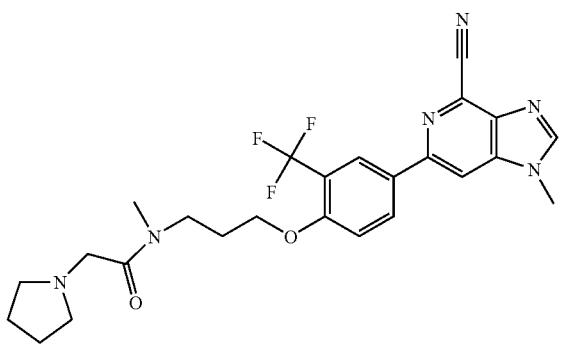

¹H NMR (CDCl₃) δ: 8.25 (m, 2H), 8.09 (s, 1H), 7.878 (s, 1H), 7.09 (d, 1H), 4.17 (t, 2H), 4.00 (s, 3H), 3.60 (m, 2H), 3.31 (d, 2H), 3.08 (s, 3H), 2.59 (broad m, 4H), 2.13 (m, 2H), 1.79 (m, 4H). MS m/z 501.2 (M+H).

EXAMPLE 26a (S)—N-(2-(4-(4-cyano-1-methyl-1H-imidazo[4,5-c]pyridin-6-yl)-2-(trifluoromethyl)-phenoxy)ethyl)-N,1-dimethylpyrrolidine-2-carboxamide

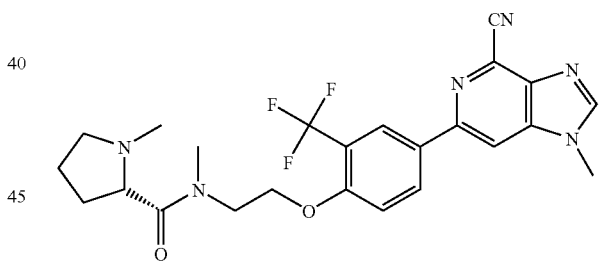

To a solution of (S)-1-methylpyrrolidine-2-carboxylic acid (16 mg), DIPEA (60 ul) and HBTU (51.7 mg) in dichloromethane (2 ml) was added 1-methyl-6-(4-(2-(methylamino)ethoxy)-3-(trifluoromethyl)phenyl)-1H-imidazo[4,5-c]pyridine-4-carbonitrile (51.1 mg). The reaction was left stirring at room temperature for 60 hrs. Reaction mixture was diluted with dichloromethane, washed with sodium bicarbonate and water. Organic layer was dried over magnesium sulphate and solvent removed under reduced pressure. The residue was purified by acidic prep HPLC and cationic ion exchange column to yield (S)—N-(2-(4-(4-cyano-1-methyl-1H-imidazo[4,5-c]pyridin-6-yl)-2-(trifluoromethyl)phenoxy)ethyl)-N,1-dimethylpyrrolidine-2-carboxamide (30.2 mg).

¹H NMR (CDCl3) δ: 8.25 (m, 2H), 8.09 (s, 1H), 7.88 (s, 1H), 7.10 (d, 1H), 4.32 (t, 2H), 4.00 (s, 3H), 3.85 (m, 2H), 3.27 (s, 3H), 3.16 (m, 2H), 2.39 (s, 3H), 2.32-1.73 (broad m, 6H). MS m/z 487.2 (M+H).

The procedure described in Example 26a was further applied, using the appropriate carboxylic acid, to prepare the following compounds:

26b: N-(2-(4-(4-cyano-1-methyl-1H-imidazo[4,5-c]pyridin-6-yl)-2-(trifluoromethyl)-phenoxy)ethyl)-N,1-dimethyl-1H-imidazole-5-carboxamide

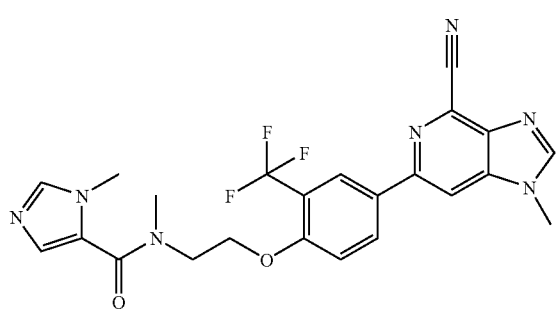

¹H NMR (CDCl3) δ: 8.24 (m, 2H), 8.07 (s, 1H), 7.87 (s, 1H), 7.50 (s, 1H), 7.33 (s, 1H), 7.09 (d, 1H), 4.40 (m, 2H), 3.99 (s, 3H), 3.83 (s, 3H), 3.48 (s, 3H), 3.40 (m, 2H). MS m/z 484.2 (M+H).

26c: N-(2-(4-(4-cyano-1-methyl-1H-imidazo[4,5-c]pyridin-6-yl)-2-(trifluoromethyl)-phenoxy)ethyl)-N,2-dimethyl-2-(pyrrolidin-1-yl)propanamide

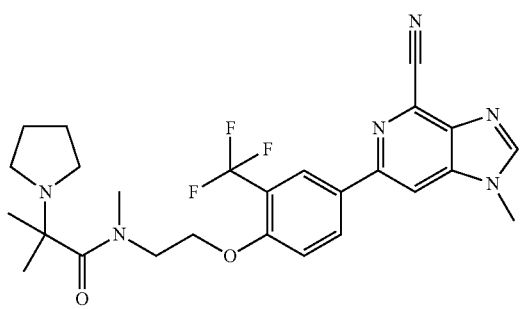

¹H NMR (CDCl3) δ: 8.24 (m, 2H), 8.08 (s, 1H), 7.87 (s, 1H), 7.09 (d, 1H), 4.40 (m, 2H), 3.99 (s, 3H), 3.75-3.59 (broad m, 6H), 2.56 (m, 4H), 1.71 (m, 4H), 1.57 (m, 6H), (.MS m/z 515.2 (M+H).

26d: 2-((1S,4R)-2-azabicyclo[2.2.1]heptan-2-yl)-N-(2-(4-(4-cyano-1-methyl-1H-imidazo[4,5-c]pyridin-6-yl)-2-(trifluoromethyl)phenoxy)ethyl)-N-methylacetamide

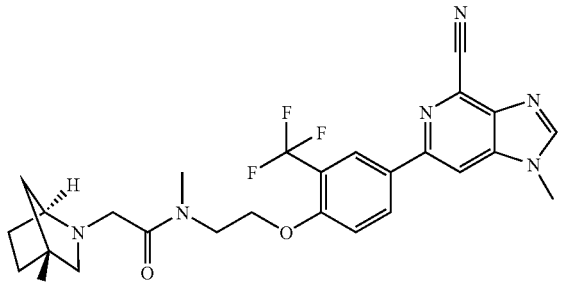

¹H NMR (CDCl3) δ: 8.24 (m, 2H), 8.08 (s, 1H), 7.87 (s, 1H), 7.09 (d, 1H), 4.30 (m, 2H), 3.99 (s, 3H), 3.76 (m, 2H), 3.49 (s, 2H), 3.22 (s, 3H), 2.90 (m, 1H), 2.31 (m, 2H), 1.82-1.21 (broad m, 7H). MS m/z 513.2 (M+H).

EXAMPLE 27

(S)—N-(2-(4-(4-cyano-1-methyl-1H-imidazo[4,5-c]pyridin-6-yl)-2-(trifluoromethyl)-phenoxy)ethyl)-N-ethyl-1-methylpyrrolidine-2-carboxamide

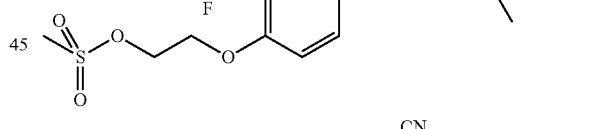

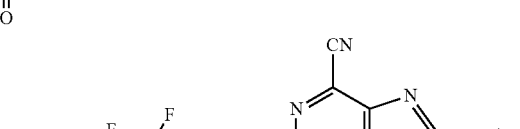

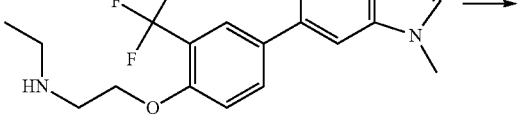

A: 6-(4-(2-(ethylamino)ethoxy)-3-(trifluoromethyl) phenyl)-1-methyl-1H-imidazo[4,5-c]pyridine-4-carbonitrile 2M ethylamine in THF (2.84 ml) was added to 2-(4-(4-cyano-1-methyl-1H-imidazo[4,5-c]pyridin-6-yl)-2-(trifluoromethyl)phenoxy)ethyl methanesulfonate (500 mg) dissolved in NMP (4 ml). Reaction mixture was heated at 100° C. under microwave conditions for 20 minutes, then filtered and purified by acidic prep HPLC to give desired product as TFA salt which was then converted to free base by Cationic Exchange Column to afford 1-methyl-6-(4-(2-(methylamino)ethoxy)-3-(trifluoromethyl)phenyl)-1H-imidazo[4,5-c]pyridine-4-carbonitrile (450 mg). $^1$H NMR (MeOD) δ: 8.43 (s, 1H), 8.38 (m, 2H), 7.33 (d, 1H), 4.32 (t, 2H), 4.02 (s, 3H), 3.09 (t, 3H), 2.78 (q, 2H), 1.19 (t, 3H)

B: (S)—N-(2-(4-(4-cyano-1-methyl-1H-imidazo[4,5-c]pyridin-6-yl)-2-(trifluoromethyl)phenoxy)ethyl)-N-ethyl-1-methylpyrrolidine-2-carboxamide To a solution of (S)-1-methylpyrrolidine-2-carboxylic acid (16 mg), DIPEA (60 ul) and HBTU (51.7 mg) in dichloromethane (2 ml) was added 1-methyl-6-(4-(2-(ethylamino) ethoxy)-3-(trifluoromethyl)phenyl)-1H-imidazo[4,5-c]pyridine-4-carbonitrile (55 mg). The reaction was left stirring at room temperature for 60 hrs. Reaction mixture was diluted with dichloromethane, washed with sodium bicarbarbonate and water. Organic layer was dried over magnesium sulphate and solvent removed under reduced pressure. The residue was purified by acidic prep HPLC and cationic ion exchange column to yield (S)—N-(2-(4-(4-cyano-1-methyl-1H-imidazo[4,5-c]pyridin-6-yl)-2-(trifluoromethyl)phenoxy) ethyl)-N-ethyl-1-methyl-pyrrolidine-2-carboxamide (40 mg).

$^1$H NMR (CDCl$_3$) δ: 8.24 (m, 2H), 8.07 (s, 1H), 7.85 (s, 1H), 7.09 (d, 1H), 4.33 (m, 2H), 3.99 (s, 3H), 3.76 (dm, 2H), 3.60 (m, 2H), 3.15 (m, 2H), 2.34 (s, 3H), 2.33-1.74 (broad m, 6H), 1.24 (t, 3H). MS m/z 501.2 (M+H).

EXAMPLE 28a

N-(3-(4-(4-cyano-1-methyl-1H-imidazo[4,5-c]pyridin-6-yl)-2-(trifluoromethyl)-phenoxy)propyl)-N,1-dimethylpiperidine-2-carboxamide

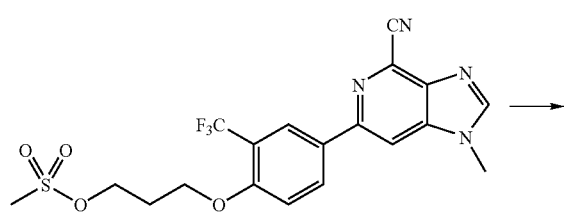

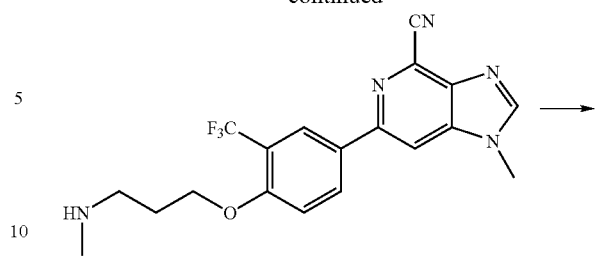

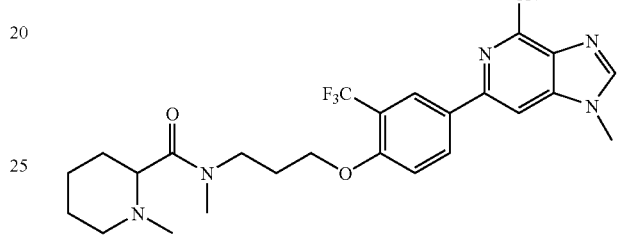

A: 1-methyl-6-(4-(3-(methylamino)propoxy)-3-(trifluoromethyl)phenyl)-1H-imidazo[4,5-c]pyridine-4-carbonitrile A mixture of 3-(4-(4-cyano-1-methyl-1H-imidazo[4,5-c]pyridin-6-yl)-2-(trifluoromethyl)phenoxy)propyl methanesulfonate (1.5 g) and methylamine in THF (2M, 8.25 ml) in NMP (12 ml) was heated at 100° C. under microwave conditions for 30 minutes. The mixture was then columned on silica gel using DCM-DCM-MeOH (19:1) then MeOH-2M ammonia in MeOH as eluant to give the expected product (757 mg). $^1$H NMR (CD3OD) δ: 8.43 (s, 1H), 8.31-8.40 (m, 3H), 7.31 (d, 1H), 4.26 (t, 2H), 4.02 (s, 3H), 2.80 (t, 2H), 2.41 (s, 3H), 2.06 (quin, 2H). MS m/z 390 (M+H).

B: N-(3-(4-(4-cyano-1-methyl-1H-imidazo[4,5-c] pyridin-6-yl)-2-(trifluoromethyl)phenoxy)propyl)-N,1-dimethylpiperidine-2-carboxamide A mixture of 1-methyl-6-(4-(3-(methylamino)propoxy)-3-(trifluoromethyl)phenyl)-1H-imidazo[4,5-c]pyridine-4-carbonitrile (50 mg), triethylamine (71 μL), 1-methylpiperidine-2-carboxylic acid hydrochloride (17 mg), and O-benzotriazol-1-yl-N,N,N',N'-tetramethyluronium hexafluorophosphate (58 mg) in DCM (1.5 ml) was stirred overnight at room temperature. The mixture was washed with sodium bicarbonate and then purified by prep HPLC (acidic) to give the expected product (11 mg). NMR (CD3OD) δ: 8.29-8.52 (m, 4H), 7.27-7.40 (m, 1H), 4.16-4.36 (m, 2H), 4.06 (s, 3H), 3.58-3.92 (m, 2H), 2.86-3.27 (m, 5H), 2.14-2.37 (m, 6H), 1.26-1.90 (m, 6H). MS m/z 515 (M+H).

The procedure described in Example 28a was further applied, using the appropriate carboxylic acids, to prepare the following compounds:

28b: 2-(2-azabicyclo[2.2.1]heptan-2-yl)-N-(3-(4-(4-cyano-1-methyl-1H-imidazo[4,5-c]pyridin-6-yl)-2-(trifluoromethyl)phenoxy)propyl)-N-methylacetamide

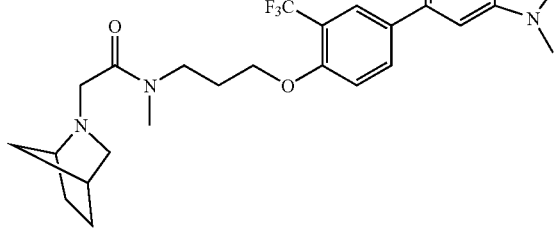

$^1$H NMR (CD3OD) δ: 8.28-8.53 (m, 4H), 7.27-7.38 (m, 1H), 4.15-4.32 (m, 2H), 4.04 (s, 3H), 3.56-3.69 (m, 2H), 3.44-3.55 (m, 2H), 3.23-3.41 (m, 1H), 2.80-3.16 (m, 4H), 2.27-2.46 (m, 2H), 2.06-2.24 (m, 2H), 1.17-1.92 (m, 6H). MS m/z 527 (M+H).

28c: (R)—N-(3-(4-(4-cyano-1-methyl-1H-imidazo[4,5-c]pyridin-6-yl)-2-(trifluoromethyl)-phenoxy)propyl)-N,1-dimethylpyrrolidine-2-carboxamide

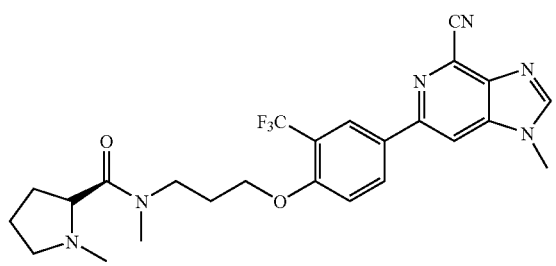

$^1$H NMR (CD3OD) δ: 8.35-8.57 (m, 4H), 7.31-7.42 (m, 1H), 4.23-4.40 (m, 2H), 4.09 (s, 3H), 3.52-3.93 (m, 2H), 3.23-3.34 (m, 1H), 3.00-3.23 (m, 4H), 2.12-2.49 (m, 7H), 1.70-2.01 (m, 3H). MS m/z 501 (M+H).

EXAMPLE 29a 1-methyl-6-(4-(2-(1-(2-(pyrrolidin-1-yl)acetyl)piperidin-4-yl)ethoxy)-3-(trifluoromethyl)-phenyl)-1H-imidazo[4,5-c]pyridine-4-carbonitrile

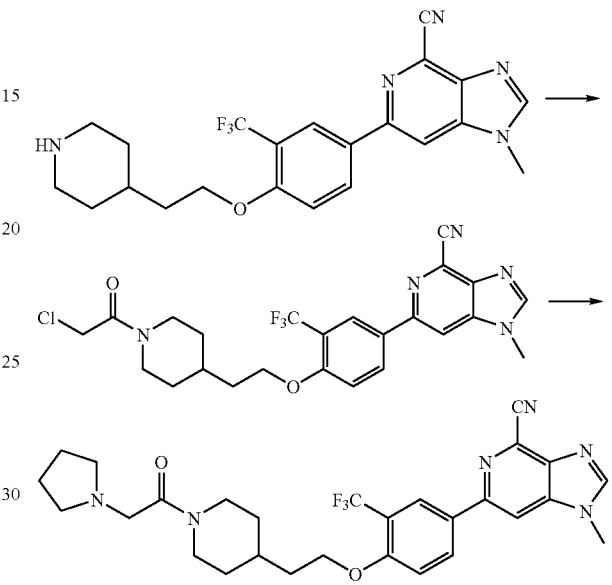

A: 6-(4-(2-(1-(2-chloroacetyl)piperidin-4-yl)ethoxy)-3-(trifluoromethyl)phenyl)-1-methyl-1H-imidazo[4,5-c]pyridine-4-carbonitrile Chloroacetylchloride (0.323 ml) in 1 ml DCM was added at 0° C. to the suspension of 1-methyl-6-(4-(2-(piperidin-4-yl)ethoxy)-3-(trifluoromethyl)phenyl)-1H-imidazo[4,5-c]pyridine-4-carbonitrile (free base) in THF/DCM (1:1, 40 ml) with DIPEA (1.7 ml). The mixture was stirred at rt for 2 hours, then 10 ml methanol added, followed by 200 ml ethyl acetate. The mixture was washed with water (100 ml), sodium bicarbonate (100 ml), dried, filtered, solvent removed, residue was columned on silica gel using 100:5 DCM/MeOH as eluant to give 0.7 g product as off white solid. $^1$H NMR (CD3OD) δ: 8.25 (d, 1H), 8.22 (s, 1H), 8.10 (s, 1H), 7.87 (s, 1H), 7.10 (d, 1H), 4.58 (m, 1H), 4.21 (t, 2H), 4.09 (d, 1H), 4.08 (d, 1H), 3.99 (s, 3H), 3.90 (m, 1H), 3.12 (t, 1H), 2.65 (t, 1H), 2.2 (m, 1H), 1.8-2.0 (m, 4H), 1.1-1.4 (m, 2H).

B: 1-methyl-6-(4-(2-(1-(2-(pyrrolidin-1-yl)acetyl)piperidin-4-yl)ethoxy)-3-(trifluoromethyl)phenyl)-1H-imidazo[4,5-c]pyridine-4-carbonitrile A mixture of 6-(4-(2-(1-(2-chloroacetyl)piperidin-4-yl)ethoxy)-3-(trifluoromethyl)phenyl)-1-methyl-1H-imidazo[4,5-c]pyridine-4-carbonitrile (25 mg), diisopropylethylamine (82 μL), and pyrrolidine (21 μL) in MeOH (1 ml) was stirred for 36 hours at room temperature. The mixture was purified by prep HPLC (acidic) to give the expected product (14 mg). $^1$H NMR (CD3OD) δ: 8.42 (s, 1H), 8.24-8.35 (m, 3H), 7.27 (d, 1H), 4.50 (d, 1H), 4.23 (t, 2H), 3.91-4.07 (m, 4H), 3.22-3.61 (m, 6H), 3.05 (t, 1H), 2.64 (t, 1H), 1.76-2.02 (m, 9H), 1.10-1.30 (m, 2H). MS m/z 541 (M+H).

The procedure described in Example 29a was further applied, using the appropriate carboxylic acids, to prepare the following compounds:

29b: 1-methyl-6-(4-(2-(1-(2-(methylamino)acetyl)piperidin-4-yl)ethoxy)-3-(trifluoromethyl)phenyl)-1H-imidazo[4,5-c]pyridine-4-carbonitrile

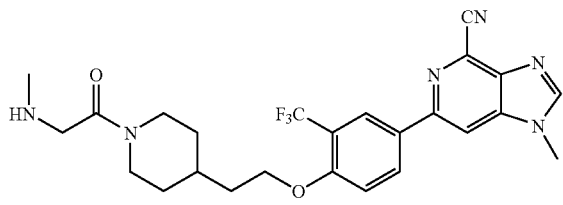

$^1$H NMR (CD3OD) δ: 8.43 (s, 1H), 8.29-8.39 (m, 3H), 7.30 (d, 1H), 4.52 (d, 1H), 4.25 (t, 2H), 4.02 (s, 3H), 3.74 (d, 1H), 3.45-3.58 (m, 2H), 3.07 (t, 1H), 2.67 (t, 1H), 2.43 (s, 3H), 1.78-1.99 (m, 5H), 1.09-1.34 (m, 2H). MS m/z 501 (M+H).

EXAMPLE 30a

N-(2-(4-(4-cyano-1-methyl-1H-imidazo[4,5-c]pyridin-6-yl)-2-(trifluoromethyl)-phenoxy)ethyl)-1-(dimethylamino)-N-methylcyclopropanecarboxamide

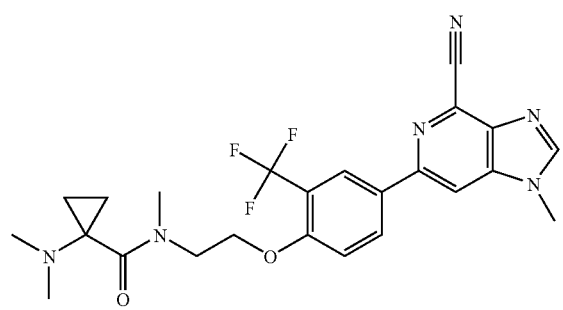

1-Methyl-6-(4-(2-(methylamino)ethoxy)-3-(trifluoromethyl)phenyl)-1H-imidazo[4,5-c]pyridine-4-carbonitrile (54 mg), 1-(dimethylamino)cyclopropane-carboxylic acid (37.2 mg), HATU (82 mg) and DIPEA (0.119 ml) were combined in NMP (2 ml) and stirred at room temperature for 16 hours. The reaction mixture was diluted with EtOAc (25 mL) and washed with 1:1 saturated sodium bicarbonate solution/water (3×15 mL). Organics were dried over sodium sulphate and solvent evaporated under reduced pressure. Purification by flash chromatography (10 g silica column, DCM to 5% MeOH in DCM gradient) followed by preparative HPLC (acidic) and SCX afforded N-(2-(4-(4-cyano-1-methyl-1H-imidazo[4,5-c]pyridin-6-yl)-2-(trifluoromethyl)phenoxy)ethyl)-1-(dimethylamino)-N-methylcyclopropane-carboxamide (22% yield) as a white solid after trituration with ether and oven drying.

$^1$H NMR (MeOD) δ: 8.45 (s, 1H), 8.40 (m, 3H), 7.34 (d, 1H), 4.39 (broad m, 2H), 4.02 (s, 3H), 3.90 (broad m, 2H), 3.31 (s, 3H), 2.30 (s, 6H), 0.98 (m, 2H), 0.90 (m, 2H). MS m/z 487.2 (M+H).

The above procedure was used to make the following compounds:

30b: N-(3-(4-(4-cyano-1-methyl-1H-imidazo[4,5-c]pyridin-6-yl)-2-(trifluoromethyl)phenoxy)propyl)-1-(dimethylamino)-N-methylcyclopropanecarboxamide

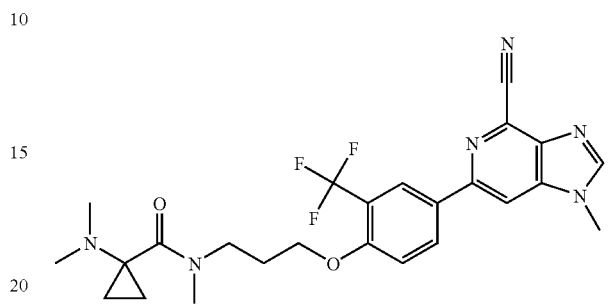

$^1$H NMR (MeOD) δ: 8.45 (s, 1H), 8.40 (m, 3H), 7.31 (d, 1H), 4.22 (t, 2H), 4.03 (s, 3H), 3.70 (broad m, 2H), 3.13 (broad s, 3H), 2.33 (s, 6H), 2.16 (broad m, 2H), 1.00 (m, 2H), 0.88 (m, 2H). MS m/z 501.2 (M+H).

30c: 6-(4-(2-(1-(1-(dimethylamino)cyclobrobanecarbonyl)piperidin-4-yl)ethoxy)-3-(trifluoromethyl)phenyl)-1-methyl-1H-imidazo[4,5-c]pyridine-4-carbonitrile

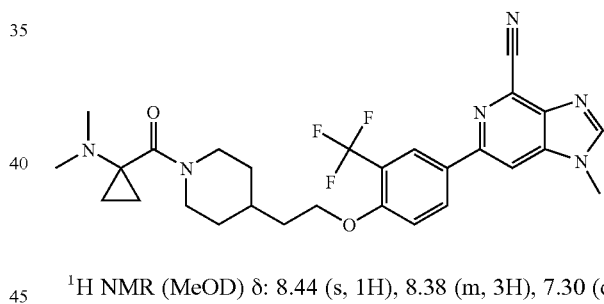

$^1$H NMR (MeOD) δ: 8.44 (s, 1H), 8.38 (m, 3H), 7.30 (d, 1H), 4.50 (d, 2H), 4.26 (m, 2H), 4.02 (s, 3H), 2.90 (m, 2H), 2.32 (s, 6H), 1.84 (m, 5H), 1.20 (m, 2H), 0.95 (m, 2H), 0.84 (m, 2H). MS m/z 541.2 (M+H).

EXAMPLE 31

1-methyl-6-(4-(2-(1-(2-(dimethylamino)acetyl)piperidin-4-yl)ethoxy)-3-(trifluoromethyl)phenyl)-1H-imidazo[4,5-c]pyridine-4-carbonitrile

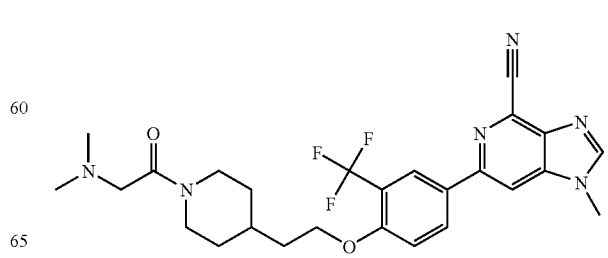

1-Methyl-6-(4-(2-(piperidin-4-yl)ethoxy)-3-(trifluoromethyl)phenyl)-1H-imidazo[4,5-c]pyridine-4-carbonitrile (0.188 g), 2-(dimethylamino)acetic acid (0.090 g) and DIPEA (0.362 ml) were dissolved in NMP (2.5 ml) and HATU (0.250 g) was then added. The reaction was stirred at room temperature for 16 hours. The reaction mixture was diluted with EtOAc (30 mL) and washed with saturated sodium bicarbonate solution. Organics were dried over sodium sulphate to yield crude. Purification by flash chromatography (10 g SiO2 column, DCM to 5% MeOH in DCM gradient) afforded methyl-6-(4-(3-(methylamino)propoxy)-3-(trifluoromethyl)phenyl)-1H-imidazo[4,5-c]pyridine-4-carbonitrile. (59 mg)

$^1$H NMR (DMSO) δ: 8.40 (s, 1H), 8.30 (m, 3H), 7.25 (d, 1H), 8.41 (s, 1H), 4.80 (s, 3H), 4.50 (d, 1H), 4.20 (t, 2H), 4.05 (d, 1H), 3.10 (m, 3H), 2.70 (t, 1H), 2.25 (s, 6H), 1.80 (m, 5H), 1.20 (m, 3H). MS m/z 515.2 (M+H).

EXAMPLE 32

Cathepsin S Assay Procedure

The inhibitory activity of the compounds of the invention was demonstrated in vitro by measuring the inhibition of recombinant human Cathepsin S as follows:
To a 384 well microtitre plate is added 10 μl of a 1000 solution of test compound in assay buffer (100 mM sodium acetate pH5.5, 5 mM EDTA, 5 mM dithiothreitol) with 10% dimethylsulfoxide (DMSO), plus 200 of 2500 solution of the substrate Z-Val-Val-Arg-AMC (7-amido-coumarine derivative of the tripeptide N-benzyloxy-carbonyl-Val-Val-Arg-OH) in assay buffer and 45 μl of assay buffer. 25 μl of a 2 mg/l solution of activated recombinant human cathepsin S, in assay buffer, is then added to the well, yielding a final inhibitor concentration of 10 μM.
Enzyme activity is determined by measuring the fluorescence of the liberated aminomethylcoumarin at 440 nM using 390 nM excitation, at 20 minutes. Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity). Compounds of the invention typically have a $pIC_{50}$ (negative logarithm of the $IC_{50}$ concentration) for inhibition of human cathepsin S of more than 6. Most compounds of the invention have a $pIC_{50}$ of more than 7, such as exemplified by the compounds of examples 1a, 1b, 2a, 7d, 12a, 14a, 14b, 14c, 14d, 14e, 14f, 14g, 14h, 14i, 17, 18.

EXAMPLE 33

Cathepsin K Assay Procedure

The inhibitory activity of the compounds of the invention was demonstrated in vitro by measuring the inhibition of recombinant human Cathepsin K as follows:
To a 384 well microtitre plate is added 5 μl of a 100 μM solution of test compound in assay buffer (100 mM sodium acetate pH5.5, 5 mM EDTA, 5 mM dithiothreitol) with 10% dimethylsulfoxide (DMSO), plus 10 μl of 100 μM solution of the substrate Z-Phe-Arg-AMC (7-amido-coumarine derivative of the dipeptide N-benzyloxycarbonyl-Phe-Arg-OH) in assay buffer and 25 μl of assay buffer. 10 μl of a 1 mg/l solution of activated recombinant human cathepsin K, in assay buffer, is then added to the well, yielding a final inhibitor concentration of 10 μM.
Enzyme activity is determined by measuring the fluorescence of the liberated aminomethylcoumarin at 440 nM using 390 nM excitation, at 10 minutes. Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity). Compounds of the invention have a $pIC_{50}$ (negative logarithm of the $IC_{50}$ concentration) for inhibition of human cathepsin K of less than 7.

EXAMPLE 34

Cathepsin S Assay

During normal antigen presentation, Lip10 is proteolytically degraded to enable loading of a peptide fragment and subsequent MHC-II presentation on the surface of antigen presenting cells. The cleavage process is mediated by Cathepsin S. Thus, the Lip10 assay is an in vitro measure of a compound's ability to block cathepsin S and by extension antigen presentation. A compound that causes the accumulation of Lip10 at low concentration would be expected to block presentation of antigens.
Cell Based Lip10 Assay Procedure Human B lymphoblastoid cells (Jiyoye) were cultured in RPMI 1640 medium at a density of 500 000 cells/ml in 24-well plates. Cells were treated with a concentration range of compounds (0.001-10 μM) and vehicle alone (DMSO, 0.1% v/v). In order to generate positive control treatments separate wells were treated with 10 μM E64d & 0.1 μM LHVS. The cells were incubated at 37° C. in a humidified incubator containing 5% $CO_2$. After 24 hours the plates were centrifuged at 150×g for five minutes and the media removed. Cells were lysed by adding 65 μl of ice-cold phosphate buffered saline (PBS) containing 1% (v/v) Triton X-100 and protease inhibitors and incubated on ice for 20 minutes. The samples were centrifuged at 18 000×g for 15 minutes at 4° C. and the resulting supernatants collected and stored at −80° C. until required. After measurement of protein concentration using a micro-BCA protein assay all samples were diluted to 10 μg protein/ml and 50 μl of each sample were coated overnight at 4° C. onto wells of high protein-binding 96-well plates. The wells were washed once with PBS (200 μl/well) and then incubated at room temperature for 2 hours with 10 μg/ml mouse anti-CD74 Pin.1 monoclonal antibody (50 μl/well) in PBS containing 0.05% (v/v) Tween-20 (PBS-T) and 2% (w/v) BSA (PBS-T/BSA). Unbound antibody was then removed by washing three times with PBS-T and followed by the addition of rabbit anti-mouse IgG antibody conjugated to horseradish peroxidase. After washing five times with PBS-T 100 μl of tetramethylbenzidine substrate was added to each well and incubated for 10 minutes on a plate shaker. The reaction was stopped by the addition of 100 μl of 1M hydrochloric acid. Antibody binding was quantified by measuring the optical density (OD, 450 nm) using a Molecular Devices Spectramax Plus. The OD of vehicle-only treated cells was removed from all values and the data was expressed as a percentage of the OD generated from the mean E64d/LHVS-treated cells. The potency of compounds ($EC_{50}$) was measured by calculating the concentration of inhibitor required to generate 50% inhibition relative to E64d/LHVS-treated cells. Compounds of the invention have a $pEC_{50}$ (negative logarithm of the $EC_{50}$ concentration) value greater than 10 μM. Many compounds have pEC$_{50}$ greater than 7, such as exemplified by the compounds of examples 12a, 12b, 12c, 14a, 14b, 14c, 14d.

EXAMPLE 35 hERG (Human Ether-a-Go-Go) Channel Activity

For assay protocol see: Diaz, J Pharm Tox Methods, 50(3), 187-199, 2004 and Optimization in Drug Discovery, Chapter "In vitro Methods", Page 353-368 by K Finlayson and J Sharkey, Ed. Z. Yan and G. W. Caldwell, 2004; Humana Press.

The invention claimed is:
1. A 6-phenyl-1H-imidazo[4,5-c]pyridine-4-carbonitrile derivative having the general Formula I

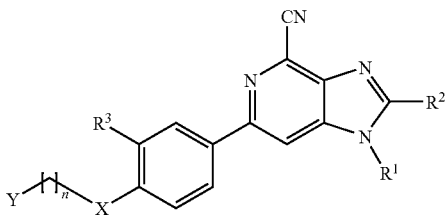

Formula I wherein
$R_1$ is H or (C$_{1-3}$)alkyl;
$R_2$ is H or (C$_{1-3}$)alkyl;
$R_3$ is halogen or (C$_{1-4}$)alkyl, optionally substituted with one or more halogens;
X is CH$_2$, O or S;
n is 1-3;
Y is selected from
NR$_4$COR$_5$,
NR$_4$SO$_2$R$_5$,

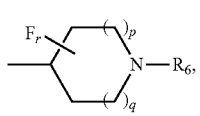

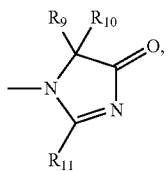
and $R_4$ is H, (C$_{1-3}$)alkyl or (C$_{3-5}$)cycloalkyl;
$R_5$ is H, (C$_{1-6}$)alkyl, (C$_{3-5}$)cycloalkyl, NR$_{12}$R$_{13}$, CR$_{16}$R$_{17}$NR$_{12}$R$_{13}$, Het or a saturated 4-6-membered NR$_{11}$ containing ring;
$R_6$ is (C$_{3-5}$)cycloalkyl, halo(C$_{1-6}$)alkyl,(C$_{1-3}$)alkyloxy (C$_{1-3}$)alkyl, (CH$_2$)$_m$CONR$_{12}$R$_{13}$, CO(C$_{1-6}$)alkyl, COCR$_{16}$R$_{17}$NR$_{12}$R$_{13}$, SO$_2$(C$_{1-6}$)alkyl, Het, COHet or CH$_2$Het;
r=0-3; p=0-2; q=0-2;
$X_1$ and $X_2$ are independently CH or N;

one of $R_7$ and $R_8$ is selected from halogen, (C$_{1-3}$)alkyloxy, NR$_{14}$R$_{15}$, CONR$_{14}$R$_{15}$, NR$_{14}$COR$_{15}$, COO(C$_{1-3}$)alkyl and phenyl; the other is H or halogen;
$R_9$ and $R_{10}$ are (C$_{1-3}$)alkyl; or
$R_9$ an $R_{10}$ form together with the carbon to which they are bonded a 3-5 membered saturated ring;
$R_{11}$ is H or (C$_{1-3}$)alkyl;
m is 0 or 1;
Het is a 5- or 6 membered heteroaryl ring comprising 1-3 heteroatoms selected from O, S and N, optionally substituted with (C$_{1-3}$)alkyl;
$R_{12}$ and $R_{13}$ are independently H, (C$_{1-6}$)alkyl, or (C$_{1-3}$) alkyloxy(C$_{1-3}$)alkyl; or
$R_{12}$ and $R_{13}$ form together with the N to which they are bonded a 5-10 membered saturated heterocyclic ring, optionally comprising a further heteroatom selected form O and S;
$R_{14}$ and $R_{15}$ are independently H or (C$_{1-6}$)alkyl; or
$R_{14}$ and $R_{15}$ form together with the N to which they are bonded a 5-7 membered saturated heterocyclic ring;
$R_{16}$ and $R_{17}$ are independently H or (C$_{1-3}$)alkyl; or
$R_{16}$ and $R_{17}$ form together with the carbon atom to which they are bonded a cyclopropyl ring;
with the proviso that when r is 0, $R_6$ is not H or (C$_{1-4}$)alkyl, or a pharmaceutically acceptable salt thereof.
2. The 6-phenyl-1H-imidazo[4,5-c]pyridine-4-carbonitrile derivative of claim 1 wherein $R_1$ is methyl.
3. The 6-phenyl-1H-imidazo[4,5-c]pyridine-4-carbonitrile derivative of claim 2, wherein $R_3$ is CF$_3$.
4. The 6-phenyl-1H-imidazo[4,5-c]pyridine-4-carbonitrile derivative of claim 3, wherein X is O and n is 1 or 2or 3.
5. The 6-phenyl-1H-imidazo[4,5-c]pyridine-4-carbonitrile derivative of claim 4, wherein Y is NR$_4$COR$_5$.
6. The 6-phenyl-1H-imidazo[4,5-c]pyridine-4-carbonitrile derivative of claim 1 which is selected from
N-(3-(4-(4-cyano-1-methyl-1H-imidazo[4,5-c]pyridin-6-yl)-2-(trifluoromethyl)phenoxy)propyl)methane-sulfonamide;
6-[4-(3-acetylaminopropoxy)-3-(trifluoromethyl)-phenyl]-1-methyl-1H-imidazo[4,5-c]pyridine-4-carbonitrile;
6-{4-[3-(N-acetyl-N-methylamino)propoxy]-3-(trifluoromethyl)-phenyl}-1-methyl-1H-imidazo[4,5-c]pyridine-4-carbonitrile;
1-methyl-6-(4-(2-(N-acetyl-N-methylamino)ethoxy)-3-(trifluoromethyl)phenyl)-1H-imidazo[4,5-c]pyridine-4-carbonitrile;
1-methyl-6-{4-[(2-(N-ethyl-N-methylamino)-pyridin-4-yl)-methoxy]-3-(trifluoromethyl)-phenyl}-1H-imidazo [4,5-c]pyridine-4-carbonitrile hydrochloride;
1-methyl-6-(4-(2-(1-(oxazol-2-ylmethyl)piperidin-4-yl) ethoxy)-3-(trifluoromethyl)phenyl)-1H-imidazo[4,5-c] pyridine-4-carbonitrile hydrochloride;
1-methyl-6-(4-(2-(1-((5-methylisoxazol-3-yl)methyl)piperidin-4-yl)ethoxy)-3-(trifluoromethyl)phenyl)-1H-imidazo[4,5-c]pyridine-4-carbonitrile;
6-(4-(2-(1-((3,5-dimethylisoxazol-4-yl)methyl)piperidin-4-yl)ethoxy)-3-(trifluoromethyl)phenyl)-1-methyl-1H-imidazo[4,5-c]pyridine-4-carbonitrile;
6-(4-(2-(1-(2-dimethylamino-2-oxo-ethyl)piperidin-4-yl) ethoxy)-3-(trifluoromethyl)phenyl)-1-methyl-1H-imidazo[4,5-c]pyridine-4-carbonitrile;
6-(4-(2-(1-(2-fluoroethyl)piperidin-4-yl)ethoxy)-3-(trifluoromethyl)phenyl)-1-methyl-1H-imidazo[4,5-c]pyridine-4-carbonitrile;

6-(4-(2-(1-(2-methoxyethyl)piperidin-4-yl)ethoxy)-3-(trifluoromethyl)phenyl)-1-methyl-1H-imidazo[4,5-c]pyridine-4-carbonitrile;

1-methyl-6-(4-(2-(1-(thiazol-2-ylmethyl)piperidin-4-yl)ethoxy)-3-(trifluoromethyl)phenyl)-1H-imidazo[4,5-c]pyridine-4-carbonitrile;

1-methyl-6-(4-(2-(1-((5-methyl-1,2,4-oxadiazol-3-yl)methyl)piperidin-4-yl)ethoxy)-3-(trifluoromethyl)phenyl)-1H-imidazo[4,5-c]pyridine-4-carbonitrile;

1-methyl-6-(4-(2-(1-((3-methyl-1,2,4-oxadiazol-5-yl)methyl)piperidin-4-yl)ethoxy)-3-(trifluoromethyl)phenyl)-1H-imidazo[4,5-c]pyridine-4-carbonitrile;

1-methyl-6-(4-(2-(1-((5-methyl-1,3,4-oxadiazol-2-yl)methyl)piperidin-4-yl)ethoxy)-3-(trifluoromethyl)phenyl)-1H-imidazo[4,5-c]pyridine-4-carbonitrile;

1-methyl-6-(4-(2-(1-((3-methylisoxazol-5-yl)methyl)piperidin-4-yl)ethoxy)-3-(trifluoromethyl)phenyl)-1H-imidazo[4,5-c]pyridine-4-carbonitrile;

6-(4-(3-acetylaminobenzoxy)-3-(trifluoromethyl)phenyl)-1H-imidazo[4,5-c]pyridine-4-carbonitrile;

6-(4-(2-(1-(2,2-dimethylamino-2-oxoethyl)-4-fluoropiperidin-4-yl)ethoxy)-3-(trifluoromethyl)phenyl)-1-methyl-1H-imidazo[4,5-c]pyridine-4-carbonitrile;

6-(4-(2-(4-fluoro-1-(2-methoxyethyl)piperidin-4-yl)ethoxy)-3-(trifluoromethyl)phenyl)-1-methyl-1H-imidazo[4,5-c]pyridine-4-carbonitrile;

6-(4-(2-(1-ethyl-4-fluoro-piperidin-4-yl)ethoxy)-3-(trifluoromethyl)phenyl)-1-methyl-1H-imidazo[4,5-c]pyridine-4-carbonitrile;

6-(4-(2-(4-fluoro-1-(2-fluoroethyl)piperidin-4-yl)ethoxy)-3-(trifluoromethyl)phenyl)-1-methyl-1H-imidazo[4,5-c]pyridine-4-carbonitrile; and 6-(4-(2-(4-fluoro-1-methyl-piperidin-4-yl)ethoxy)-3-(trifluoromethyl)phenyl)-1-methyl-1H-imidazo[4,5-c]pyridine-4-carbonitrile;

1-methyl-6-(4-(2-(1-(pyridin-2-yl)piperidin-4-yl)ethoxy)-3-(trifluoromethyl)phenyl)-1H-imidazo[4,5-c]pyridine-4-carbonitrile;

1-methyl-6-(4-(2-(1-(6-methyl-pyridin-2-yl)piperidin-4-yl)ethoxy)-3-(trifluoromethyl)phenyl)-1H-imidazo[4,5-c]pyridine-4-carbonitrile;

N-(2-(4-(4-cyano-1-methyl-1H-imidazo[4,5-c]pyridin-6-yl)-2-(trifluoromethyl)phenoxy)ethyl)-2-(dimethylamino)-N-methylacetamide;

N-(2-(4-(4-cyano-1-methyl-1H-imidazo[4,5-c]pyridin-6-yl)-2-(trifluoromethyl)phenoxy)ethyl)-N-methyl-2-(pyrrolidin-1-yl)acetamide;

(S)—N-(2-(4-(4-cyano-1-methyl-1H-imidazo[4,5-c]pyridin-6-yl)-2-(trifluoromethyl)phenoxy)ethyl)-N,1-dimethylpyrrolidine-2-carboxamide;

2-((1S,4R)-2-azabicyclo[2.2.1]heptan-2-yl)-N-(2-(4-(4-cyano-1-methyl-1H-imidazo[4,5-c]pyridin-6-yl)-2-(trifluoromethyl)phenoxy)ethyl)-N-methylacetamide;

1-methyl-6-(4-(2-(1-(2-(pyrrolidin-1-yl)acetyl)piperidin-4-yl)ethoxy)-3-(trifluoromethyl)phenyl)-1H-imidazo[4,5-c]pyridine-4-carbonitrile; and 1-methyl-6-(4-(2-(1-(2-(dimethylamino)acetyl)piperidin-4-yl)ethoxy)-3-(trifluoromethyl)phenyl)-1H-imidazo[4,5-c]pyridine-4-carbonitrile;

or a pharmaceutically acceptable salt thereof.

7. A pharmaceutical composition comprising a 6-phenyl-1H-imidazo[4,5-c]pyridine-4-carbonitrile derivative of claim 1 or a pharmaceutically acceptable salt thereof, in admixture with one or more pharmaceutically acceptable auxilliaries.

8. A pharmaceutical composition comprising a 6-phenyl-1H-imidazo[4,5-c]pyridine-4-carbonitrile derivative selected from N-(3-(4-(4-cyano-1-methyl-1H-imidazo[4,5-c]pyridin-6-yl)-2-(trifluoromethyl)phenoxy)propyl)methanesulfonamide;

6-[4-(3-acetylaminopropoxy)-3-(trifluoromethyl)-phenyl]-1-methyl-1H-imidazo[4,5-c]pyridine-4-carbonitrile;

6-{4-[3-(N-acetyl-N-methylamino)propoxy]-3-(trifluoromethyl)-phenyl}-1-methyl-1H-imidazo[4,5-c]pyridine-4-carbonitrile;

1-methyl-6-(4-(2-(N-acetyl-N-methylamino)ethoxy)-3-(trifluoromethyl)phenyl)-1H-imidazo[4,5-c]pyridine-4-carbonitrile;

1-methyl-6-{4-[(2-(N-ethyl-N-methylamino)-pyridin-4-yl)-methoxy]-3-(trifluoromethyl)-phenyl}-1H-imidazo[4,5-c]pyridine-4-carbonitrile hydrochloride;

1-methyl-6-(4-(2-(1-(oxazol-2-ylmethyl)piperidin-4-yl)ethoxy)-3-(trifluoromethyl)phenyl)-1H-imidazo[4,5-c]pyridine-4-carbonitrile hydrochloride;

1-methyl-6-(4-(2-(1-((5-methylisoxazol-3-yl)methyl)piperidin-4-yl)ethoxy)-3-(trifluoromethyl)phenyl)-1H-imidazo[4,5-c]pyridine-4-carbonitrile;

6-(4-(2-(1-((3,5-dimethylisoxazol-4-yl)methyl)piperidin-4-yl)ethoxy)-3-(trifluoromethyl)phenyl)-1-methyl-1H-imidazo[4,5-c]pyridine-4-carbonitrile;

6-(4-(2-(1-(2-dimethylamino-2-oxo-ethyl)piperidin-4-yl)ethoxy)-3-(trifluoromethyl)phenyl)-1-methyl-1H-imidazo[4,5-c]pyridine-4-carbonitrile;

6-(4-(2-(1-(2-fluoroethyl)piperidin-4-yl)ethoxy)-3-(trifluoromethyl)phenyl)-1-methyl-1H-imidazo[4,5-c]pyridine-4-carbonitrile;

6-(4-(2-(1-(2-methoxyethyl)piperidin-4-yl)ethoxy)-3-(trifluoromethyl)phenyl)-1-methyl-1H-imidazo[4,5-c]pyridine-4-carbonitrile;

1-methyl-6-(4-(2-(1-(thiazol-2-ylmethyl)piperidin-4-yl)ethoxy)-3-(trifluoromethyl)phenyl)-1H-imidazo[4,5-c]pyridine-4-carbonitrile;

1-methyl-6-(4-(2-(1-((5-methyl-1,2,4-oxadiazol-3-yl)methyl)piperidin-4-yl)ethoxy)-3-(trifluoromethyl)phenyl)-1H-imidazo[4,5-c]pyridine-4-carbonitrile;

1-methyl-6-(4-(2-(1-((3-methyl-1,2,4-oxadiazol-5-yl)methyl)piperidin-4-yl)ethoxy)-3-(trifluoromethyl)phenyl)-1H-imidazo[4,5-c]pyridine-4-carbonitrile;

1-methyl-6-(4-(2-(1-((5-methyl-1,3,4-oxadiazol-2-yl)methyl)piperidin-4-yl)ethoxy)-3-(trifluoromethyl)phenyl)-1H-imidazo[4,5-c]pyridine-4-carbonitrile;

1-methyl-6-(4-(2-(1-((3-methylisoxazol-5-yl)methyl)piperidin-4-yl)ethoxy)-3-(trifluoromethyl)phenyl)-1H-imidazo[4,5-c]pyridine-4-carbonitrile;

6-(4-(3-acetylaminobenzoxy)-3-(trifluoromethyl)phenyl)-1H-imidazo[4,5-c]pyridine-4-carbonitrile;

6-(4-(2-(1-(2,2-dimethylamino-2-oxoethyl)-4-fluoropiperidin-4-yl)ethoxy)-3-(trifluoromethyl)phenyl)-1-methyl-1H-imidazo[4,5-c]pyridine-4-carbonitrile;

6-(4-(2-(4-fluoro-1-(2-methoxyethyl)piperidin-4-yl)ethoxy)-3-(trifluoromethyl)phenyl)-1-methyl-1H-imidazo[4,5-c]pyridine-4-carbonitrile;

6-(4-(2-(1-ethyl-4-fluoro-piperidin-4-yl)ethoxy)-3-(trifluoromethyl)phenyl)-1-methyl-1H-imidazo[4,5-c]pyridine-4-carbonitrile;

6-(4-(2-(4-fluoro-1-(2-fluoroethyl)piperidin-4-yl)ethoxy)-3-(trifluoromethyl)phenyl)-1-methyl-1H-imidazo[4,5-c]pyridine-4-carbonitrile;

6-(4-(2-(4-fluoro-1-methyl-piperidin-4-yl)ethoxy)-3-(trifluoromethyl)phenyl)-1-methyl-1H-imidazo[4,5-c]pyridine-4-carbonitrile;

1-methyl-6-(4-(2-(1-(pyridin-2-yl)piperidin-4-yl)ethoxy)-3-(trifluoromethyl)phenyl)-1H-imidazo[4,5-c]pyridine-4-carbonitrile;

1-methyl-6-(4-(2-(1-(6-methyl-pyridin-2-yl)piperidin-4-yl)ethoxy)-3-(trifluoromethyl)phenyl)-1H-imidazo[4,5-c]pyridine-4-carbonitrile;

N-(2-(4-(4-cyano-1-methyl-1H-imidazo[4,5-c]pyridin-6-yl)-2-(trifluoromethyl)phenoxy)ethyl)-2-(dimethylamino)-N-methylacetamide;

N-(2-(4-(4-cyano-1-methyl-1H-imidazo[4,5-c]pyridin-6-yl)-2-(trifluoromethyl)phenoxy)ethyl)-N-methyl-2-(pyrrolidin-1-yl)acetamide;

(S)—N-(2-(4-(4-cyano-1-methyl-1H-imidazo[4,5-c]pyridin-6-yl)-2-(trifluoromethyl)phenoxy)ethyl)-N,1-dimethylpyrrolidine-2-carboxamide;

2-((1S,4R)-2-azabicyclo[2.2.1]heptan-2-yl)-N-(2-(4-(4-cyano-1-methyl-1H-imidazo[4,5-c]pyridin-6-yl)-2-(trifluoromethyl)phenoxy)ethyl)-N-methylacetamide;

1-methyl-6-(4-(2-(1-(2-(pyrrolidin-1-yl)acetyl)piperidin-4-yl)ethoxy)-3-(trifluoromethyl)phenyl)-1H-imidazo[4,5-c]pyridine-4-carbonitrile; and 1-methyl-6-(4-(2-(1-(2-(dimethylamino)acetyl)piperidin-4-yl)ethoxy)-3-(trifluoromethyl)phenyl)-1H-imidazo[4,5-c]pyridine-4-carbonitrile; or a pharmaceutically acceptable salt thereof, in admixture with one or more pharmaceutically acceptable auxilliaries.

\* \* \* \* \*